(12) United States Patent
Malecha et al.

(10) Patent No.: US 7,381,749 B2
(45) Date of Patent: *Jun. 3, 2008

(54) SULFONAMIDES AS INHIBITORS OF HISTONE DEACETYLASE FOR THE TREATMENT OF DISEASE

(75) Inventors: James William Malecha, San Diego, CA (US); Stewart Alwyn Noble, San Diego, CA (US); Christian Andreus Hassig, Mira Mesa, CA (US); Paul L. Wash, San Diego, CA (US); Brandon M. Wiley, Philadelphia, PA (US); Charles Maxwell Lawrence, San Diego, CA (US); Timothy Z. Hoffman, San Diego, CA (US)

(73) Assignee: Kalypsys, Inc., San Diego, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 11/150,783

(22) Filed: Jun. 9, 2005

(65) Prior Publication Data

US 2006/0030554 A1 Feb. 9, 2006

Related U.S. Application Data

(60) Provisional application No. 60/635,019, filed on Dec. 9, 2004.

(51) Int. Cl.
*A61K 31/18* (2006.01)
*C07C 303/00* (2006.01)

(52) U.S. Cl. .......... 514/601; 514/513; 514/602; 564/84

(58) Field of Classification Search .......... 564/84; 514/601, 513, 602
See application file for complete search history.

(56) References Cited

U.S. PATENT DOCUMENTS 4,129,656 A 12/1978 Lang
4,226,775 A * 10/1980 McEvoy et al. .......... 548/533
4,866,091 A 9/1989 Matsuo et al.
5,034,417 A 7/1991 Matsuo et al.
2003/0229126 A1 12/2003 Satoh et al.
2006/0030543 A1 2/2006 Malecha

FOREIGN PATENT DOCUMENTS

WO 06063294 A2 6/2006
WO 07016354 A1 2/2007
WO 07067994 A1 6/2007

OTHER PUBLICATIONS

Joseph W. Payne; Inhibitors of Histone Deacetylase for the Treatment of Disease; U.S. Appl. No. 11/608,736, filed Dec. 8, 2006 (not yet published); Kalypsys, Inc.

* cited by examiner

*Primary Examiner*—Rei-Tsang Shiao
(74) *Attorney, Agent, or Firm*—Dennis A. Bennett

(57) ABSTRACT

Disclosed herein are carbonyl compounds of having the structural formula:

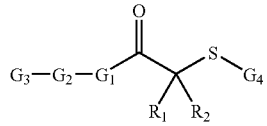

or a pharmaceutically acceptable salt, amide, ester, or prodrug thereof,

Methods and compositions are disclosed for treating disease states including, but not limited to cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis play a role in pathogenesis, using the compounds of the invention. In addition, methods of modulating the activity of histone deacetylase (HDAC) are also disclosed.

30 Claims, No Drawings

US 7,381,749 B2

SULFONAMIDES AS INHIBITORS OF HISTONE DEACETYLASE FOR THE TREATMENT OF DISEASE

RELATED DOCUMENTS

The present application claims priority to the following applications: U.S. patent application Ser. No.: 60/635,019 filed Dec. 9, 2004; U.S. patent application Ser. No.: 10/865,743 filed Jun. 10, 2004; which are incorporated herein by reference in their entirety.

FIELD OF THE INVENTION

The present invention is directed to carbonyl compounds as inhibitors of histone deacetylase (HDAC). These compounds are useful in treating disease states including cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis plays a role in pathogenesis.

BACKGROUND OF THE INVENTION

Histone proteins organize DNA into nucleosomes, which are regular repeating structures of chromatin. The acetylation status of histones alters chromatin structure, which, in turn, is involved in gene expression. Two classes of enzymes can affect the acetylation of histones—histone acetyltransferases (HATs) and histone deacetylases (HDACs). A number of HDAC inhibitors have been characterized. However, to date no effective candidate for cancer therapy has been identified. Therefore, there is a need in the art to discover HDAC inhibitors that have effective anti-tumor activity.

SUMMARY OF THE INVENTION

Disclosed herein are carbonyl compounds having structural formula (I) or related formulate as described herein:

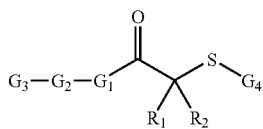
(I)

related formulae as described herein, including their pharmaceutically acceptable salts, esters, and prodrugs thereof, wherein $G_1$ is an optionally substituted phenyl or optionally substituted 5 or 6 membered heteroaryl, $G_2$ is an N-sulfonamide moiety having structure (II) or an S-sulfonamide moiety having structure (III):

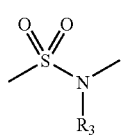
(II)

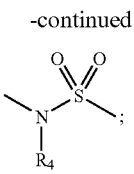
(III)

$G_3$ is optionally substituted phenyl or optionally substituted 5 or 6 membered heteroaryl, or optionally substituted alkyl, wherein $R_1$ and $R_2$ are each independently selected from the group consisting of hydrogen, lower alkyl, halogen and perhaloalkyl, or $R_1$ and $R_2$ taken together form optionally substituted cycloalkyl, wherein $R_3$ and $R_4$ are each independently selected from the group consisting of hydrogen, optionally substituted lower alkyl, optionally substituted aryl, and optionally substituted alkaryl; or a structural element known to confer aqueous solubility, e.g. N-piperazinylethyl, N-morpholinylethyl, 1,3-dihydroxy-2N-propanoyl etc., $G_4$ is chosen from the group consisting of optionally substituted acyl, wherein $G_4$ taken in combination with sulfur forms a thioester, optionally substituted thiol, wherein $G_4$ taken in combination with sulfur forms a disulfide, and $—P(O)(OR_5)_2$ or $—P(O)(OH)_2$, wherein $G_4$ taken in combination with sulfur, forms a phosphorothioate diester or phosphorothioate; and each $R_5$ is independently selected from the group consisting of hydrogen, alkyl, aryl, and arylalkyl.

The invention provides pharmaceutical compositions comprising a compound having structural formula (I) or a related formula, which are capable of inhibiting the catalytic activity of histone deacetylase (HDAC).

The invention also provides methods and compositions for treating diseases in mammals using compounds of the invention, including but not limited to, treating cancers, autoimmune diseases, tissue damage, central nervous system disorders, neurodegenerative disorders, fibrosis, bone disorders, polyglutamine-repeat disorders, anemias, thalassemias, inflammatory conditions, cardiovascular conditions, and disorders in which angiogenesis plays a role in pathogenesis.

The invention further provides methods of inhibiting the catalytic activity and cellular function of histone deacetylase (HDAC).

DETAILED DESCRIPTION OF THE PREFERRED EMBODIMENT

Definition of Terms

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclorhexylamine, N-methyl-D-glucamine, tris(hydroxymethyl)methylamine, and salts with amino acids such as arginine, lysine, and the like.

The terms "physiologically acceptable" and "physiologically compatible" refers to excipients, products, or hydrolysis products of disclosed molecular embodiments of the invention. By way of example, protected thiol prodrug embodiments may release acids upon hydrolysis of the protected thiol. Physiologically acceptable excipients and acids are those that do not abrogate the biological activity or properties of the compound, and are nontoxic. "Physiologically acceptable" and "pharmaceutically acceptable" may be coextensive terms.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1. Any amine, hydroxy, or carboxyl side chain on the compounds of the present invention can be esterified. The procedures and specific groups to be used to achieve makes such esters are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety.

An "amide" is a chemical moiety with formula —$(R)_n$—C(O)NHR' or —$(R)_n$— NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end is known to those of skill in the art and can readily be found in reference sources such as Greene and Wuts, *Protective Groups in Organic Synthesis,* $_3$rd Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Yet another example of a prodrug are protected thiol compounds. Thiols bearing hydrolyzable protecting groups can unmask protected SH groups prior to or simultaneous to use. As shown below, the moiety —C(O)—$R_E$ of a thioester may be hydrolyzed to yield a thiol and a pharmaceutically acceptable acid HO—C(O)—$R_E$.

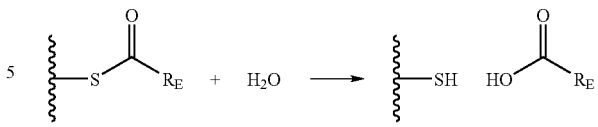

The term "thiol protecting group" refers to thiols bearing hydrolyzable protecting groups that can unmask protected SH groups prior to or simultaneous to use. Preferred thiol protecting groups include but are not limited to thiol esters which release pharmaceutically acceptable acids along with an active thiol moiety. Such pharmaceutically acceptable acids are generally nontoxic and do not abbrogate the biological activity of the active thiol moiety. Examples of pharmaceutically acceptable acids include, but are not limited to: N,N-diethylglycine; 4-ethylpiperazinoacetic acid; ethyl 2-methoxy-2-phenylacetic acid; N,N-dimethylglycine; (nitrophenoxysulfonyl)benzoic acid; acetic acid; maleic acid; fumaric acid; benzoic acid; tartraric acid; natural amino acids (like glutamate, aspartate, cyclic amino acids such proline); D-amino acids; butyric acid; fatty acids like palmitic acid, stearic acid, oleate; pipecolic acid; phosphonic acid; phosphoric acid; pivalate(trimethylacetic acid); succinic acid; cinnamic acid; anthranilic acid; salicylic acid; lactic acid; and pyruvic acids.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 4 carbon atoms. The alkyl group of the compounds of the invention may be designated as "$C_1$-$C_5$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, any group(s) besides hydrogen can be the substitutent group(s). When substituted, the substituent group(s) is(are) one or more group(s) individually and independently selected from the following non-limiting illustrative list: alkyl, cycloalkyl, aryl, heteroaryl, heterocycloalkyl, hydroxy, alkoxy, aryloxy, O, S, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Each substituent group may be further substituted.

Unless otherwise indicated, when a group is described as "optionally substituted," it is meant that the group may be substituted with one or more substituents selected from the following non-limiting illustrative list: hydroxy, alkyl, alkoxy, aryloxy, cycloalkyl, aryl, carbocyclic cycloalkyl, carbocyclic aryl, heteroaryl, heterocycloalkyl, O, S, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and protected derivatives thereof. Protecting groups that may form the protective derivatives of the substituents recited above are known to those of skill in the art and may be found in references such as Greene and Wuts, above. Each optional substituent may be further optionally substituted. Optionally substituted groups may be unsubstituted.

The term "halo" or, alternatively, "halogen" means fluoro, chloro, bromo or iodo. Preferred halo groups are fluoro, chloro and bromo. The terms "haloalkyl," "haloalkenyl," "haloalkynyl" and "haloalkoxy" include alkyl, alkenyl, alkynyl and alkoxy structures, that are substituted with one or more halo groups or with combinations thereof The terms "fluoroalkyl" and "fluoroalkoxy" include haloalkyl and haloalkoxy groups, respectively, in which the halo is fluorine.

The term "hetero" in such terms as "heteroalkyl," "heteroalkenyl," "heteroalkynyl," "heterocycloalkyl," and "heteroaryl" refers to groups in which one or more of the backbone atoms is selected from an atom other than carbon, e.g., oxygen, nitrogen, sulfur, phosphorus or combinations thereof.

Cyclic alkyl moeities contain one or more covalently closed ring structures. Cyclic alkyl moeities can have a single ring (monocyclic) or two or more rings (polycyclic or multicyclic). Polycyclic groups include fused polycyclic groups wherein rings share adjacent pairs of backbone atoms, and linked cyclic groups wherein the rings are separate but linked. In fused polycyclic groups, rings may share adjacent carbon atoms, or may share non-carbon atoms such as N. Linked polycyclic groups may be connected by a bond or a linker. Polycyclic groups can be linked by an optionally substituted alkyl moiety including but not limited to saturated alkyl linkers, or unsaturated alkyl linkers such as alkylene (e.g., methylene, ethylene, or propylene) or alkynylene linkers.

The term "carbocyclic" refers to a compound which contains one or more covalently closed ring structures, wherein the atoms forming the backbone of the ring are all carbon atoms.

The term "heterocyclic" refers to a compound with contains one or more covalently closed ring structures, wherein at least one ring backbone contains at least one atom which is different from carbon. Generally, heterocyclic groups can contain one to four herteroatoms, each selected from O, S and N, wherein each ring has from 4 to 10 atoms in the ring. Generally, heterocyclic rings do not contain two adjacent O or S atoms. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl.

The term "cycloalkyl" refers to an aliphatic cyclic alkyl moeity wherein the ring is either completely saturated, partially unsaturated, or fully unsaturated, wherein if there is unsaturation, the conjugation of the pi-electrons in the ring do not give rise to aromaticity. The term "cycloalkyl" may refer to a monocyclic or polycyclic group. Cycloalkyl groups may be fused or linked to other cyclic alkyl moeities. A cycloalkyl group may be optionally substituted. Preferred cycloalkyl groups include groups having from three to twelve ring atoms, more preferably from 5 to 10 ring atoms. The term "carbocyclic cycloalkyl" refers to a monocyclic or polycyclic cycloalkyl group which contains only carbon and hydrogen. The term "heterocycloalkyl" refers to a monocyclic or polycyclic cycloalkyl group wherein at least one ring backbone contains at least one atom which is different from carbon. Illustrative examples of carbocyclic cycloalkyl groups include the following moieties:

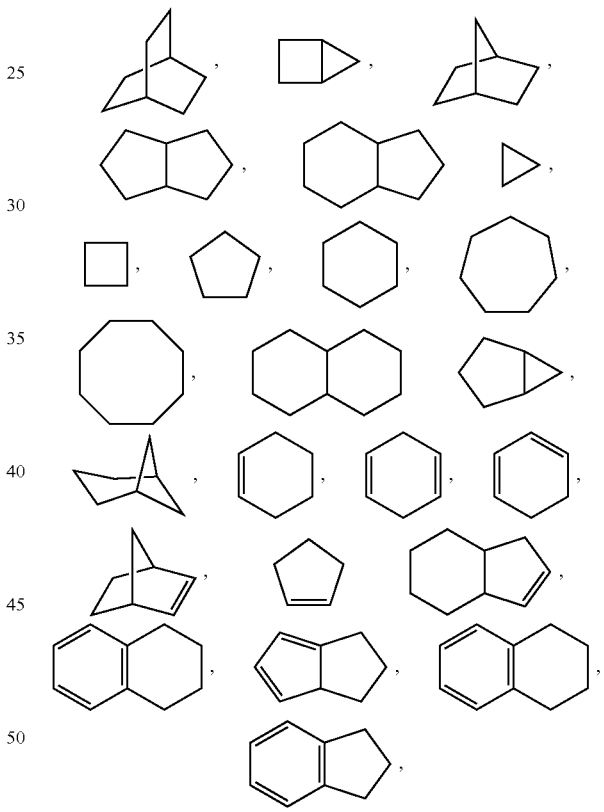

and the like.

A heterocycloalkyl group refers to a cycloalkyl group that includes at least one heteroatom selected from nitrogen, oxygen and sulfur. Heterocycloalkyl groups may be fused with one or more aryl, heteroaryl, cycloalkyl, or heterocycloalkyl groups. Heterocycloalkyl groups may be linked with one or more aryl, heteroaryl, cycloalkyl, or heterocycloalkyl groups. Examples of heterocycloalkyl (non-aromatic heterocyclic groups) are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups include:

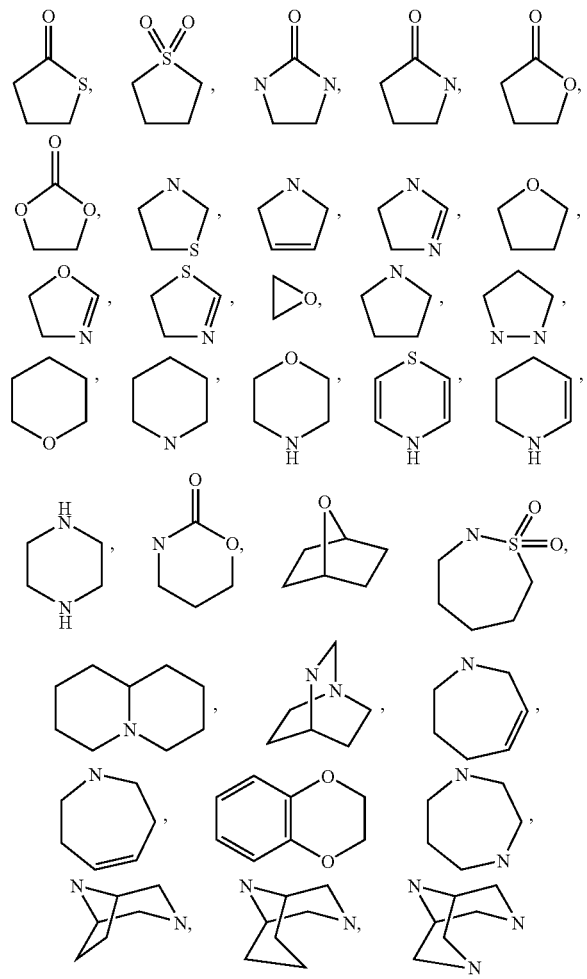

and the like.

The terms "aryl" or "aromatic" refer to a group which has at least one ring having a conjugated pi electron system. Aryl groups can be carbocyclic aryl groups or heteroaryl groups. The term "carbocyclic aryl" refers to a group (e.g., phenyl) in which all ring backbone atoms are carbon. The terms "heteroaryl" or "heteroaromatic" refer to an aryl (aromatic) group that includes one or more ring heteroatoms selected from nitrogen, oxygen and sulfur. Aryl groups may be optionally substituted. Aryl groups may be monocyclic or polycyclic. Polycyclic aryl groups may be fused or linked. Polycyclic aryl groups can be fused or linked to aryl groups or cycloalkyl groups.

Examples of heteroaryl groups include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Polycyclic heteroaryl groups may be attached through carbon ring backbone atoms, or may be attached through ring backbone heteroatoms, especially N, depending on structure of the group. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). Polycyclic heteroaryl groups include benzo-fused ring systems and ring systems substituted with one or two oxo (=O) moieties such as pyrrolidin-2-one.

Illustrative examples of heteroaryl groups include the following moieties:

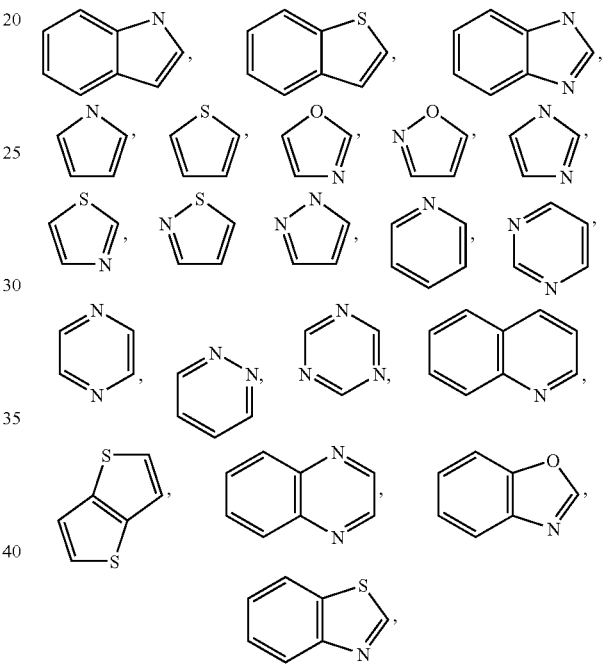

and the like.

The substituent "R" appearing by itself and without a number designation refers to a substituent selected from the group consisting of optionally substituted alkyl, including optionally substituted alkenyl or alkynyl, optionally substituted cycloalkyl, optionally substituted aryl, optionally substituted heteroaryl (bonded through a ring carbon) and optionally substituted hetercycloalkyl (bonded through a ring carbon).

An "O-carboxy" group refers to a RC(=O)O— group, where R is as defined herein.

A "C-carboxy" group refers to a —C(=O)OR groups where R is as defined herein.

An "acyl" group refers to a —C(=O)R group.

An "acetyl" group refers to a —C(=O)CH$_3$, group.

A "trihalomethanesulfonyl" group refers to a X$_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a X$_3$CS(=O)$_2$NR— group with X and R as defined herein.

An "O-carbamyl" group refers to a —OC(=O)—NR, group-with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NH— group, with R as defined herein.

The term partially halogenated alkyl refers to an alkyl group having both hydrogen and halogen substituents.

The term "perhaloalkyl" refers to an alkyl group where all of the hydrogen atoms are replaced by halogen atoms.

The term "lower perfluoroalkoxy" refers to a radical —O—(CX$_2$)$_n$CX$_3$ where X is any halogen, preferable F or Cl, and n is 1-5.

When two substituents taken together along with the two ring carbons to which they are attached form a ring, it is meant that the following structure:

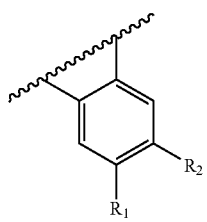

is, for example, representative of a structure such as the following:

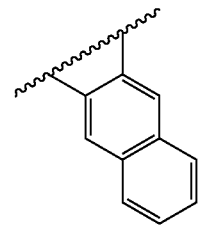

In the above example, R$_1$ and R$_2$, taken together along with the two ring carbons to which they are attached, form a six-membered aromatic ring.

Solubility is a thermodynamic parameter and plays an important role in the determination of a drug's bioavailability. Since a drug must be soluble in the gastrointestinal fluid to be orally active, the rate and extent of dissolution depend critically upon intrinsic water solubility (neutral species solubility) (Dressman, J.; Amindo, G. L.,; Reppas, C.; Shah. V. P. *Pharm. Res.*, 1998, 15, 11.) Experimental and computational approaches to estimate solubility and permeability in drug discovery and development setting have been described (Lipinski C. A. et al. 1997 *Adv. Drug Deliv. Rev.* 23, 3-25) *Adv. Drug Deliv. Rev.* 23, 3-25). Traditional analytical methods define solubility as the concentration of material in solution at equilibrium with its solid form. In this method a compound is extensively shaken in the buffer of choice, filtered through a micropore membrane, and the concentration of dissolved compound in the filtrate determined. This approach results in a thermodynamic solubility assessment. For discovery, it is beneficial to measure kinetic solubility in which a compound DMSO solution is added to aqueous buffer. Several high throughput approaches for solubility have been described, e.g. turbidimetric method (Bevan, C. and Lloyd, R. S. *Anal. Chem.* 2000 72, 1781-1787), nephelometric method (Avdeef, A. (2001) High throughput measurements of solubility profiles. In *Pharmacokinetic Optimization in Drug Research; Biological, Physicochemical, And Computational Strategies* (Testa, B. et al., eds), pp. 305-326, Verlag Helvitica Chimica Actaand). Measurement of solubility at multiple pH levels (pH 1-8), is more useful that a single pH, since many drug candidates contain ionizable groups. A solubility-pH profile provides the pH gradient of the gastrointestinal tract.

Accurate understanding of a compound's solubility is also necessary to not only prepare and dispense formulations, but also to evaluate new chemical series and provide feedback to drive synthetic optimization. Structural series of compounds are synthesized with the aim of improving solubility by the addition of various chemical moieties. Structural elements known to confer aqueous solubility on otherwise insoluble molecular entities include but are not limited to N-piperazinylethyl, N-morpholinylethyl, 1,3-dihydroxy-2N-propanoyl moieties. Common solubilizing groups often incorporated in synthetic approaches to improve solubility of molecules include amine functionality, such as dimethylamino, diethylamino, piperazinyl, N-methyl-N-isopropylamino, morpholino, pyrrolidino moieties, or groups bearing aliphatic alcohol functionality, such as that found in ethanolamine or glycerol.

In certain embodiments of the invention, a structural element known to confer aqueous solubility is incorporated in a compound of the invention. Such structural elements are preferably attached to synthetically accessible regions of the compound. In certain embodiments, such structural elements are attached to or incorporate synthetically available N atoms in amine or amide or sulfonamide moieties of the compound. In certain embodiments a solubilizing group is attached to or incorporates a N atom and is chosen from the group consisting of dimethyl amino, diethylamino, piperazinyl, N-methyl-N-isopropyl amino, morpholino, pyrrolidino moieties, or groups bearing aliphatic alcohol functionality, such as that found in ethanolamine or glycerol.

Compounds of the Invention

The invention provides compounds having structural formula (I),

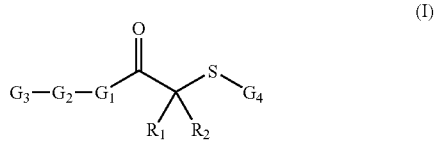

or a pharmaceutically acceptable salt, amide, ester, or prodrug thereof, wherein G$_1$ is optionally substituted phenyl or optionally substituted 5 or 6 membered heteroaryl, or G₁ and R₃ taken together form an optionally substituted heterocycloalkyl, G₂ is an N-sulfonamide moiety having structure (II), an S-sulfonamide moiety having structure (III), or an amide of the form —NR₃C(O)— or —C(O)NR₃—:

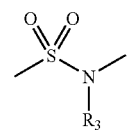
(II)

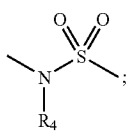
(III)

G₃ is optionally substituted phenyl or optionally substituted 5 or 6 membered heteroaryl, or optionally substituted alkyl, R₁ and R₂ are each independently selected from the group consisting of hydrogen, lower alkyl, halogen and perhaloalkyl, or R₁ and R₂ taken together form optionally substituted cycloalkyl, R₃ and R₄ are each independently selected from the group consisting of hydrogen, optionally substituted lower alkyl, optionally substituted aryl, and optionally substituted alkaryl, or a structural element known to confer aqueous solubility, including but not limited to N-piperazinylethyl, N-morpholinylethyl, or 1,3-dihydroxy-2N-propanoyl, or R3 and R4 taken together form an optionally substituted heterocycloalkyl, and G₄ is chosen from the group consisting of optionally substituted acyl, wherein G₄ taken in combination with sulfur forms a thioester, optionally substituted thiol, wherein G₄ taken in combination with sulfur forms a disulfide, and structure (IV)

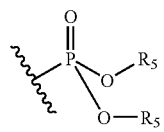
IV wherein G₄, taken in combination with sulfur, forms a phosphorothioate diester or phosphorothioate.

In certain embodiments of compounds having Structure (I) as described above, GI is an optionally substituted phenyl having structure (IV) or (V):

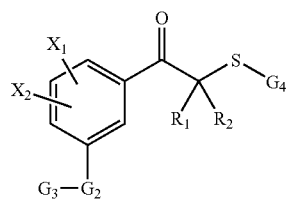
(IV)

-continued

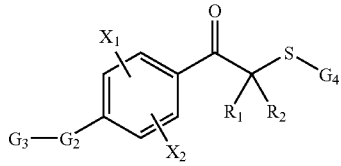
(V)

wherein X₁ and X₂ are each independently selected from the group consisting of hydrogen, halogen, hydroxyl, optionally substituted lower alkyl, optionally substituted lower alkoxy.

In certain embodiments, compounds have the structure of Formula (1), wherein G₁ is an optionally substituted phenyl having structure (IV) or (V) and G2 is N-sulfonamide moiety having structure (VI) or (VII);

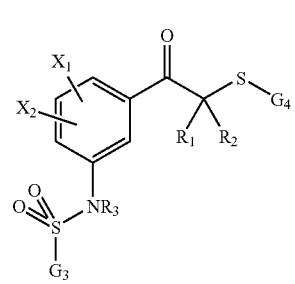
(VI)

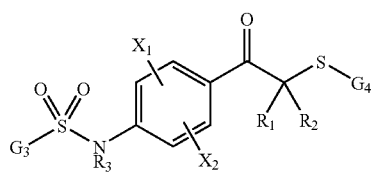
(VII)

In certain embodiments, compounds have the structure of Formula (1), wherein G₁ is an optionally substituted phenyl having structure (IV) or (V) and G2 is N-sulfonamide moiety having structure (VI) or (VII), and G3 comprises is an optionally substituted phenyl of structure (VIII) or (IX)

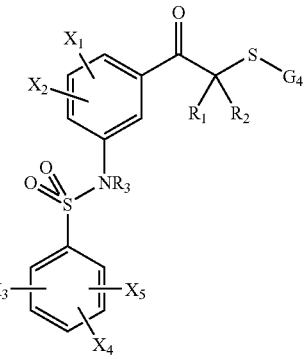
(VIII)

-continued (IX)

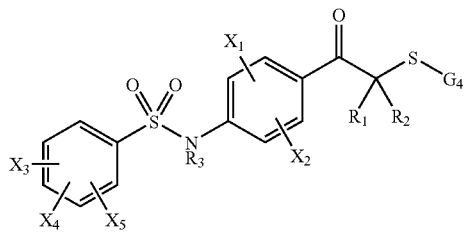

wherein X3, X4 and X5 are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl.

In certain embodiments, compounds have the structure of Formula (1), wherein $G_1$ is an optionally substituted phenyl having structure (IV) or (V), G2 is N-sulfonamide moiety having structure (VI) or (VII), G3 comprises is an optionally substituted phenyl of structure (VIII) or (IX), and G4 is an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(OR$_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_3$ can be hydrogen, optionally substituted lower alkyl, or a structural element known to confer aqueous solubility. Particular embodiments include:

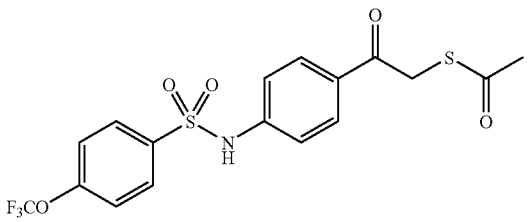

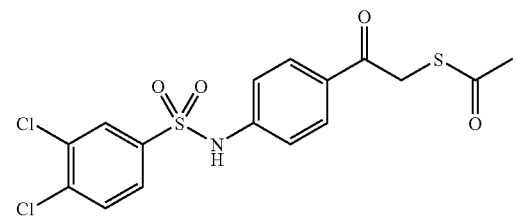

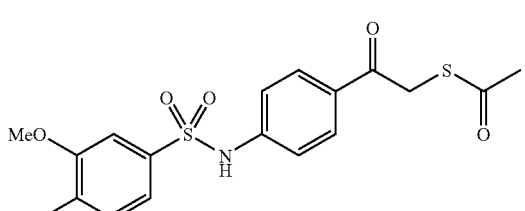

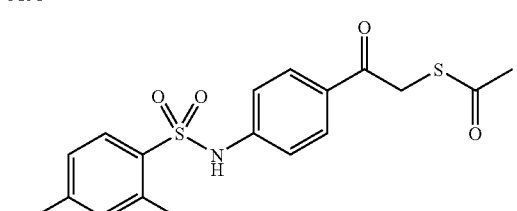

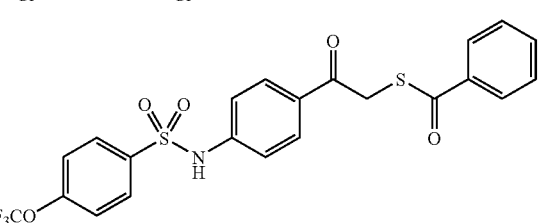

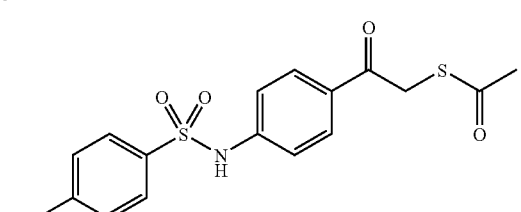

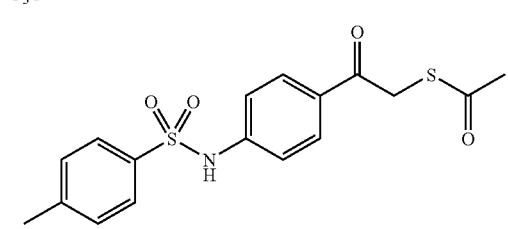

-continued
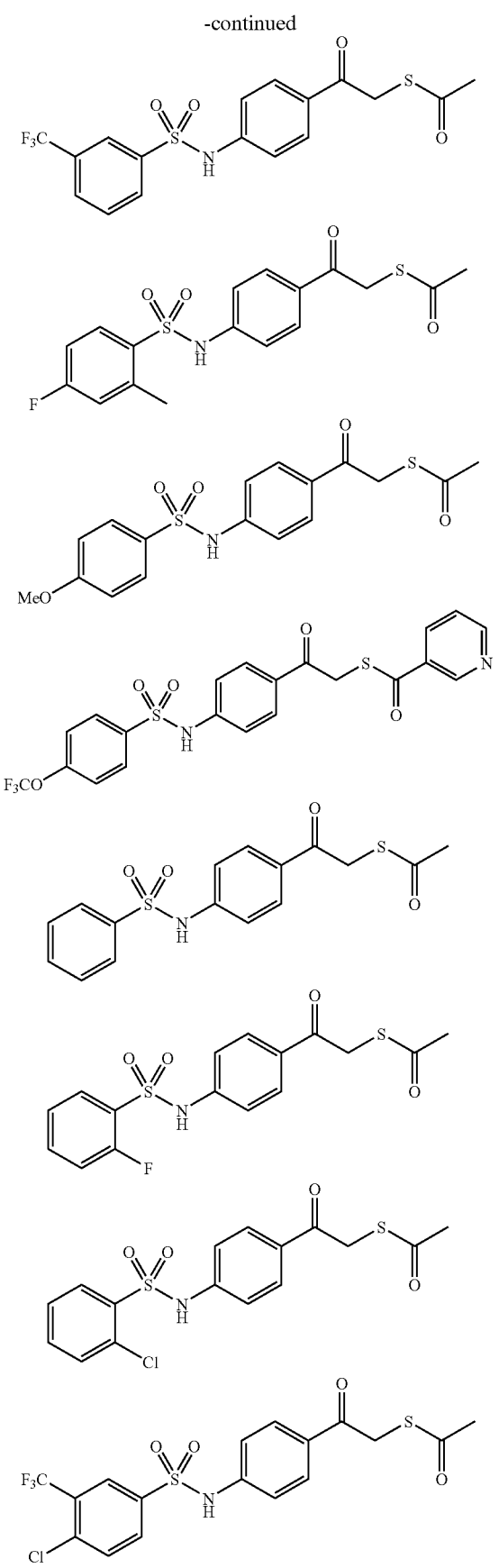
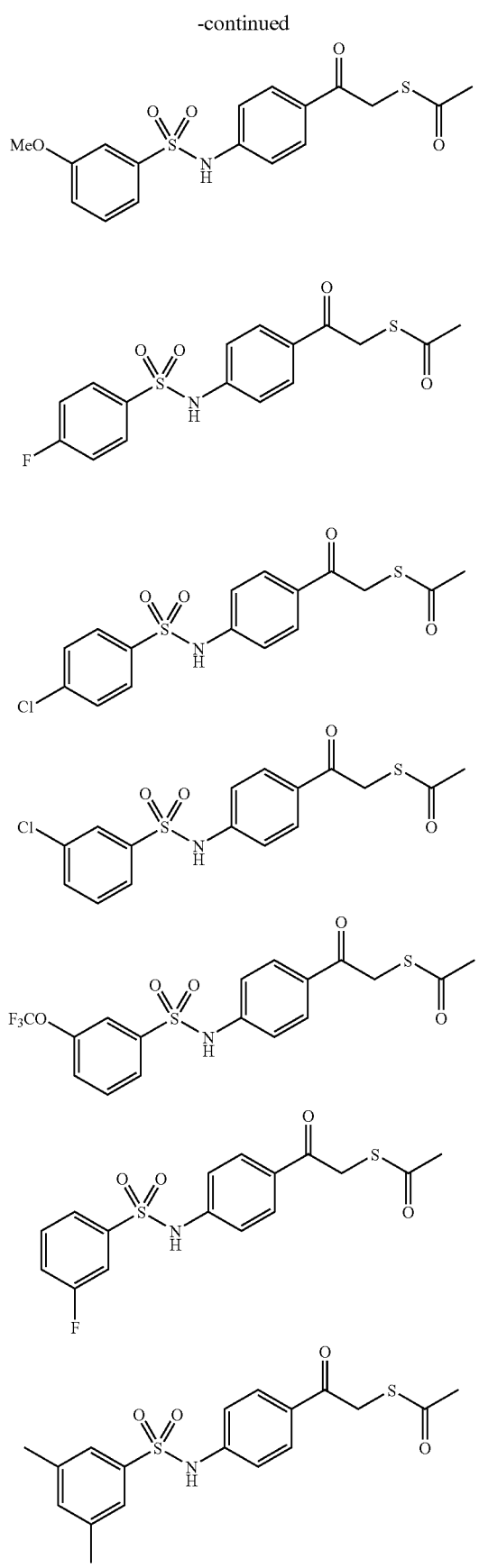

-continued

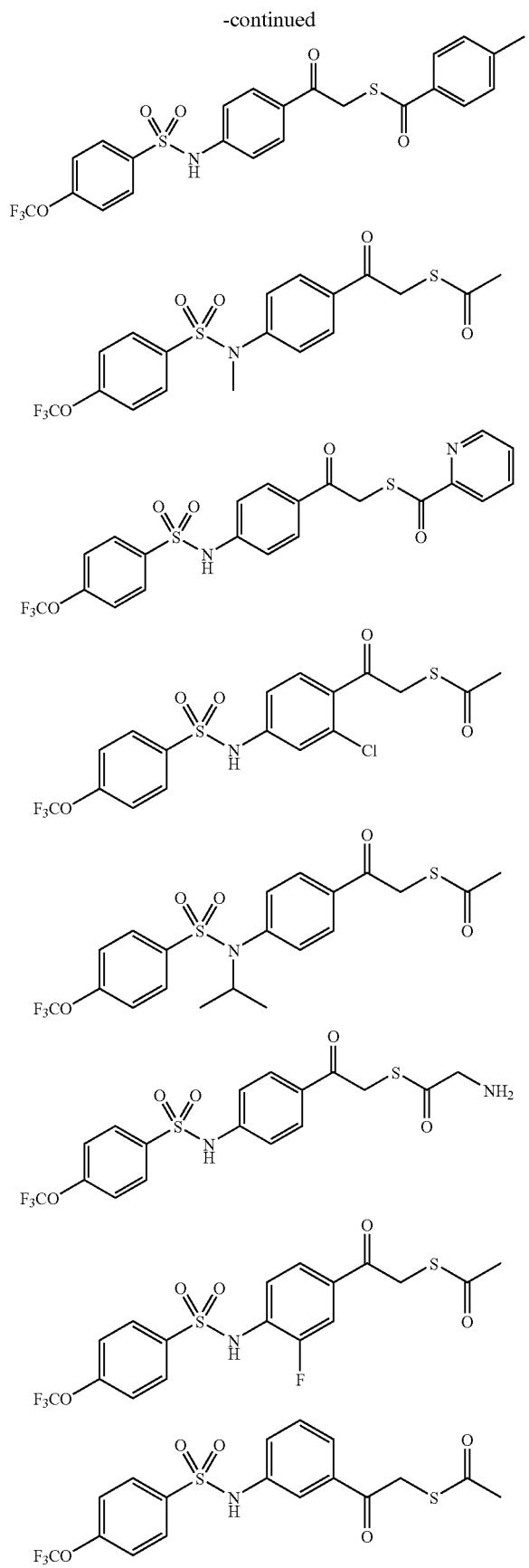

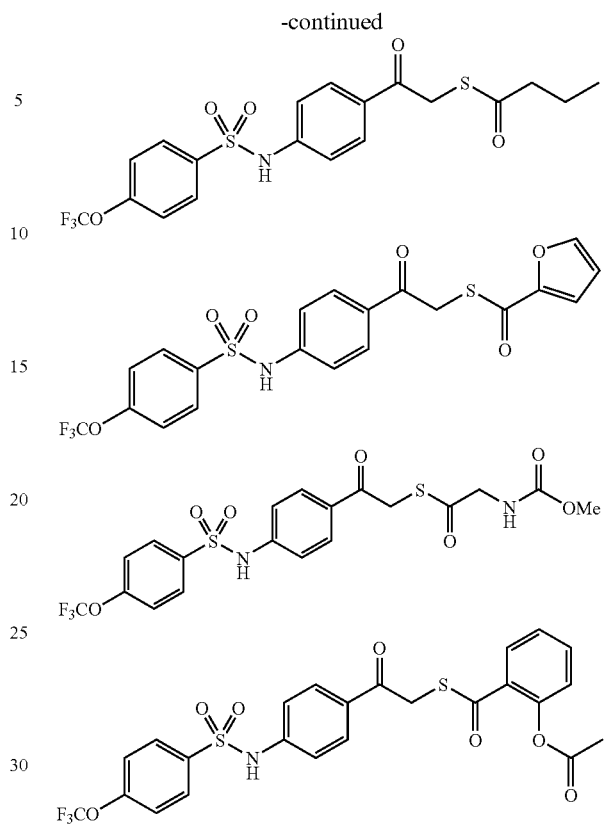

In certain embodiments, compounds have the structure of Formula (1), wherein $G_1$ is an optionally substituted phenyl having structure (IV) or (V), G2 is N-sulfonamide moiety having structure (VI) or (VII), and $G_3$ comprises an 5 or 6 membered heteroaromatic optionally substituted by $X_3$, $X_4$, $X_5$, wherein $X_3$, $X_4$ and $X_5$ are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, arylamidocarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, or aminothiocarbonylaminoalkyl. In particular embodiments, $G_3$ is selected can be any of the following:

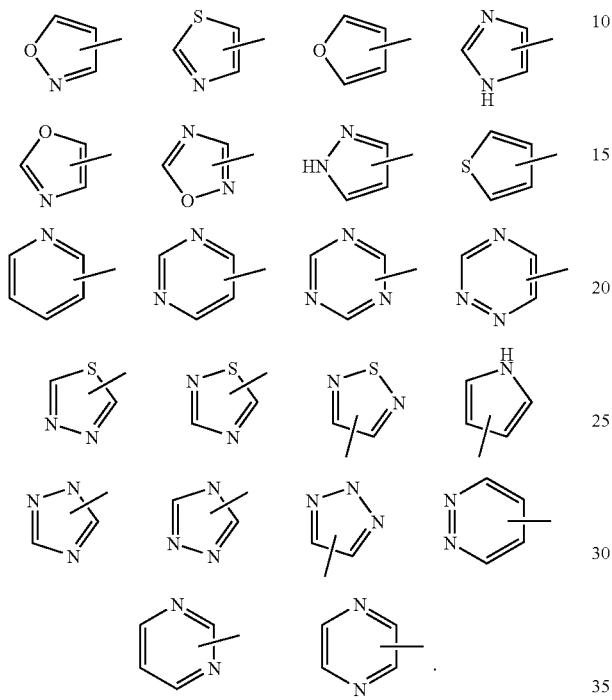

In further embodiments, $G_4$ is an optionally substituted acyl of the formula —C(O)$R_E$, wherein $R_E$ is any pharmaceutically acceptable acid; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_3$ can be hydrogen, optionally substituted lower alkyl, or a structural element known to confer aqueous solubility. Particular embodiments include:

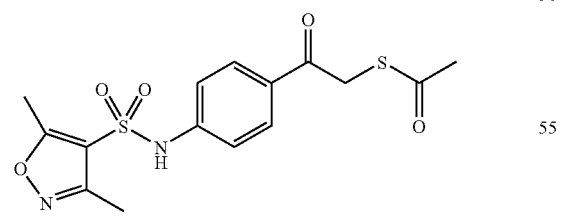

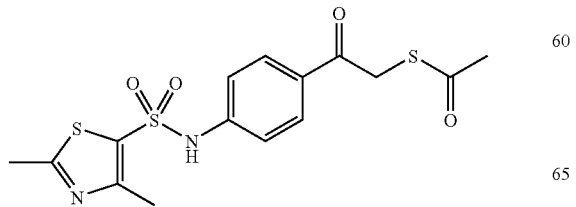

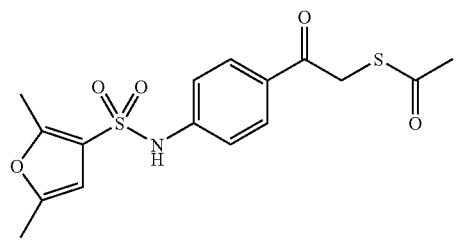

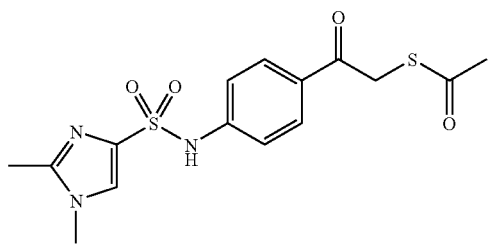

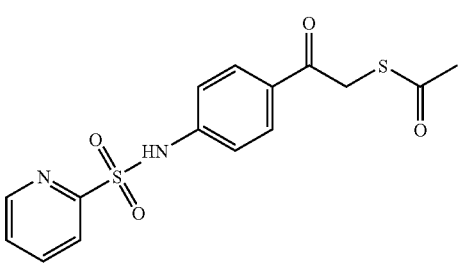

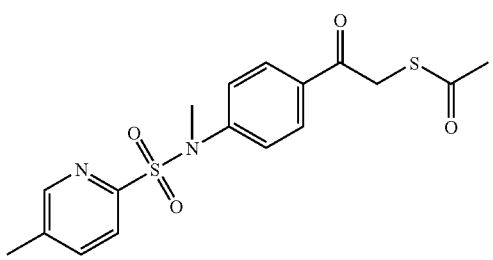

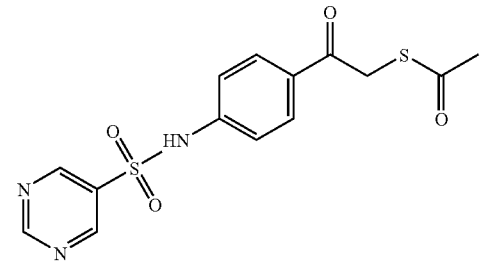

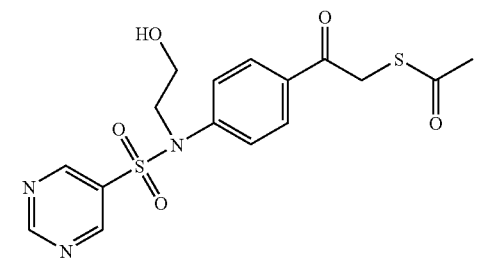

-continued

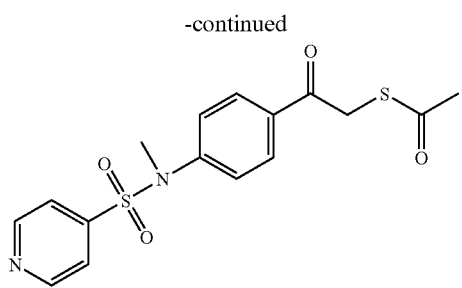

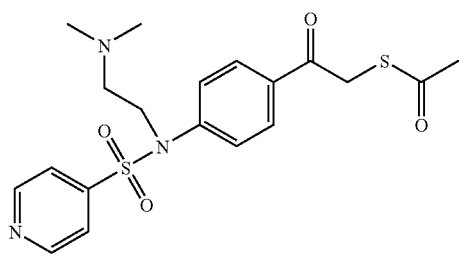

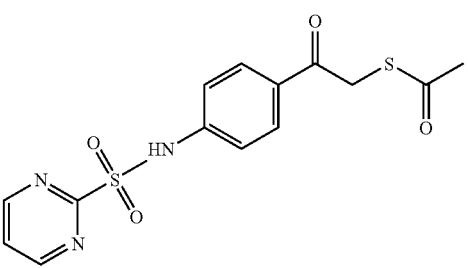

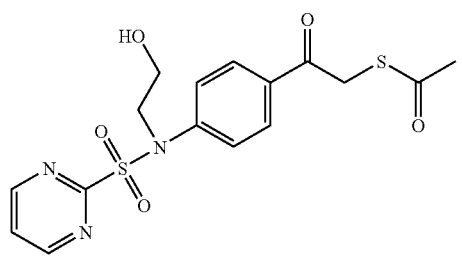

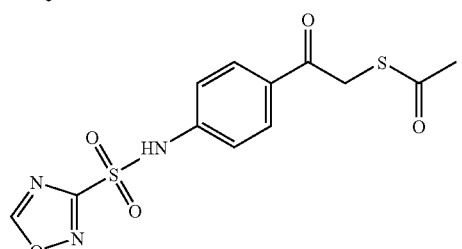

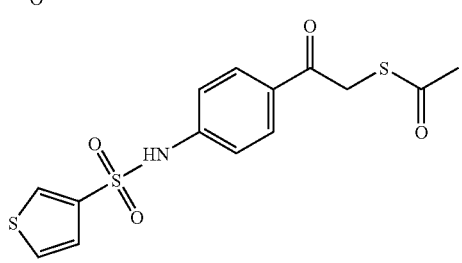

-continued

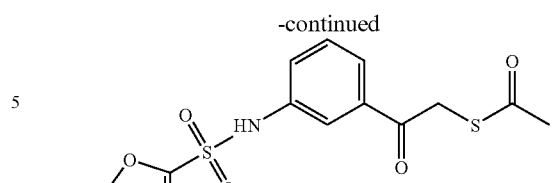

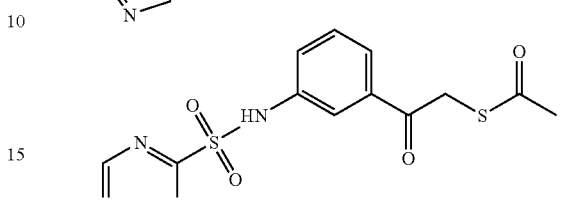

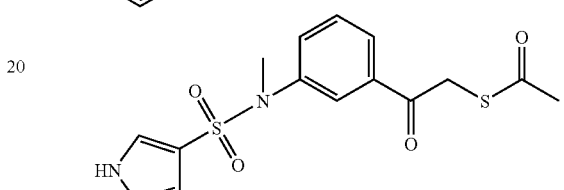

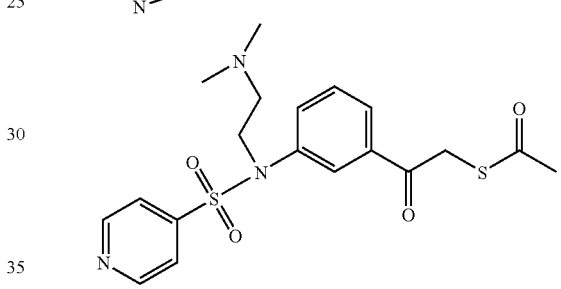

In certain embodiments, compounds have the structure of Formula (1), wherein $G_1$ is an optionally substituted phenyl having structure (IV) or (V), G2 is N-sulfonamide moiety having structure (VI) or (VII), and $G_3$ is an optionally substituted alkyl. In further embodiments, $G_4$ is an optionally substituted acyl of the formula —C(O)$R_E$, wherein $R_E$ is any pharmaceutically acceptable acid; R1 and R2 are each independently hydrogen, lower alkyl or R1 and R2 taken together form optionally substituted cycloalkyl; and X1 and X2 are each independently selected from hydrogen, halogen, hydroxyl, lower alkyl, lower perhaloalkyl, lower alkoxy and lower perhaloalkoxy. R3 can be hydrogen, optionally substituted lower alkyl, or a structural element known to confer aqueous solubility. Particular embodiments include:

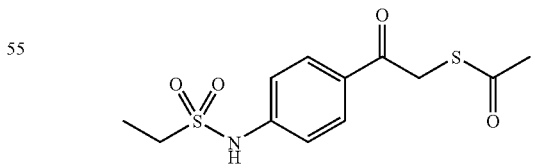

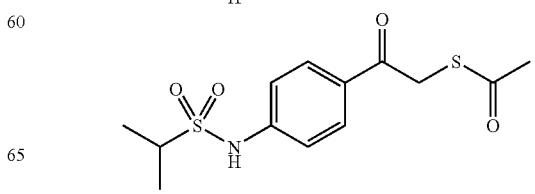

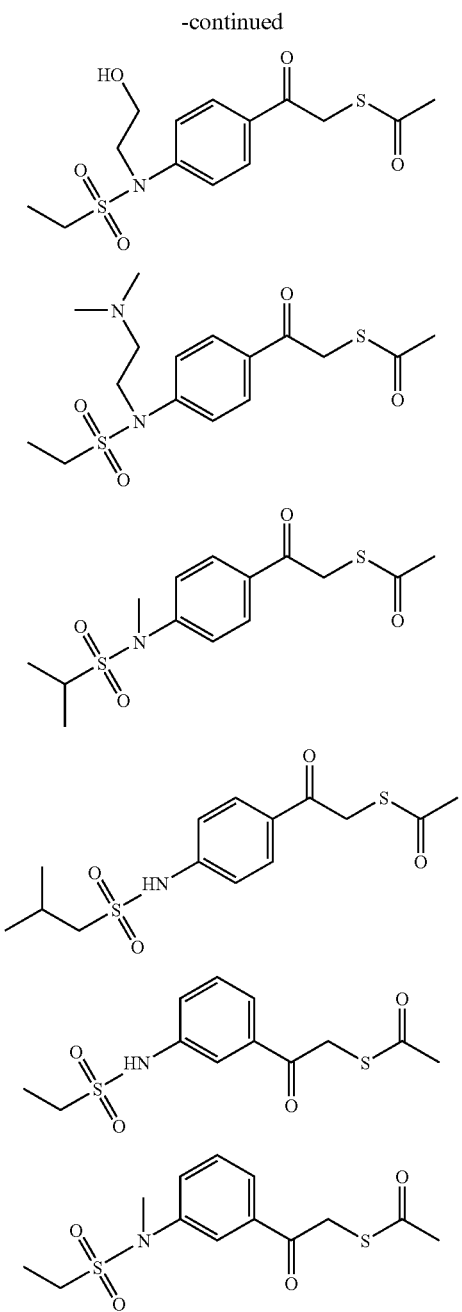

In certain embodiments, compounds have Structure (I) as described above, $G_1$ is an optionally substituted phenyl having structure (IV) or (V), and G2 is S-sulfonamide moiety having structure (X) or (XI) as shown below.

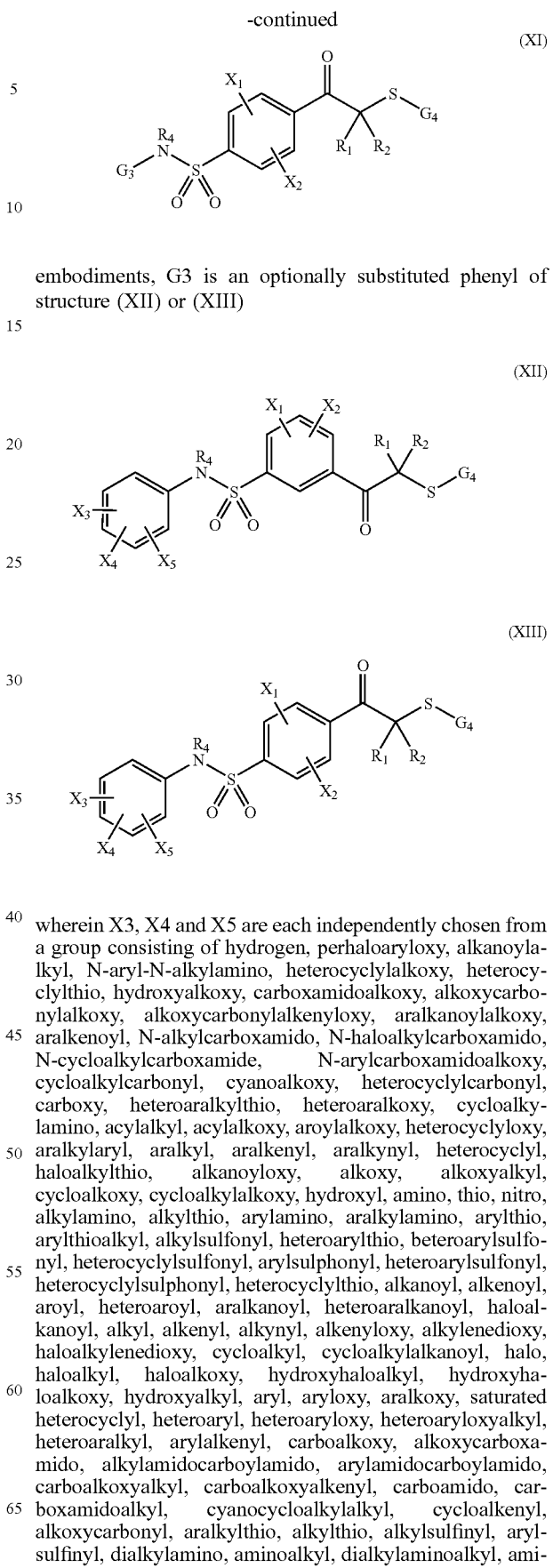

embodiments, G3 is an optionally substituted phenyl of structure (XII) or (XIII)

wherein X3, X4 and X5 are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, beteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carbalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl. In further embodiments, G4 is an optionally substituted acyl of the formula —C(O)R$_E$, wherein R$_E$ is any pharmaceutically acceptable acid; R1 and R2 are each independently hydrogen, lower alkyl or R1 and R2 taken together form optionally substituted cycloalkyl; and X1 and X2 are each independently selected from hydrogen, halogen, hydroxyl, lower alkyl, lower perhaloalkyl, lower alkoxy and lower perhaloalkoxy. R4 can be hydrogen, optionally substituted lower alkyl, or a structural element known to confer aqueous solubility. Particular embodiments include:

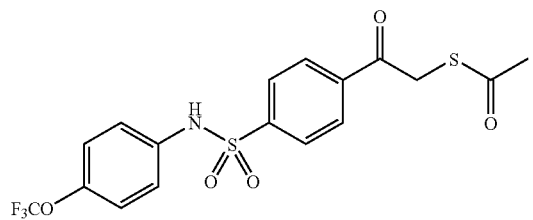

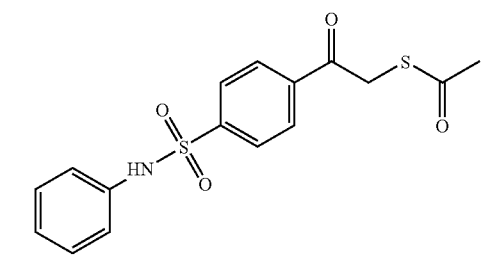

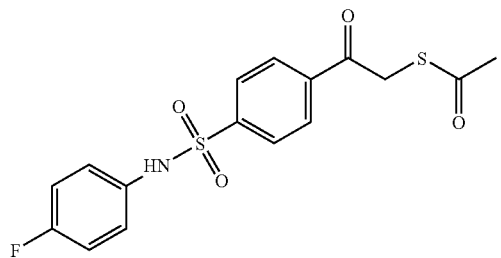

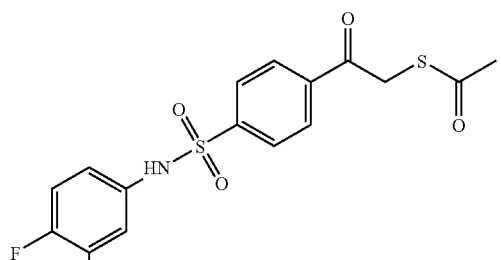

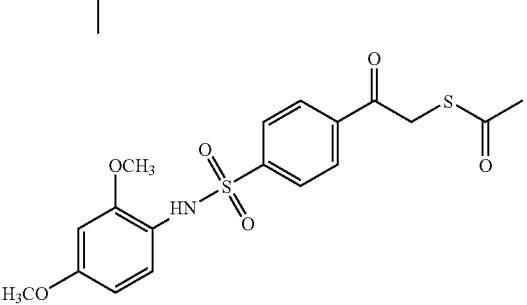

-continued

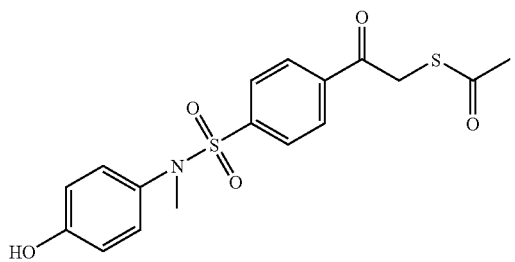

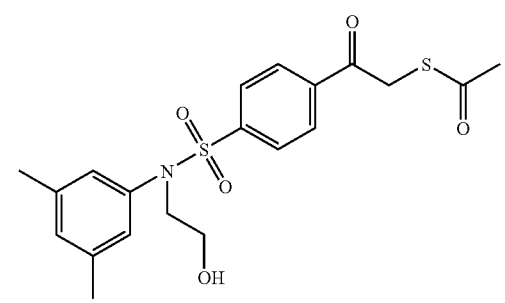

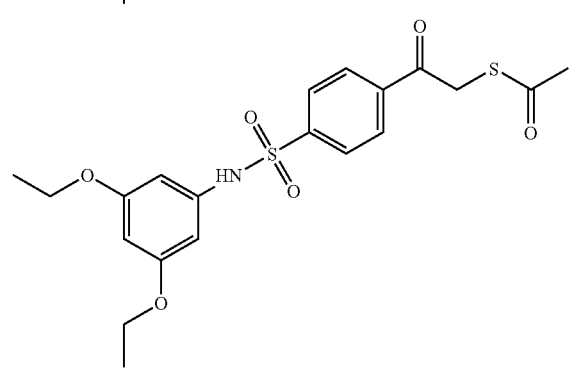

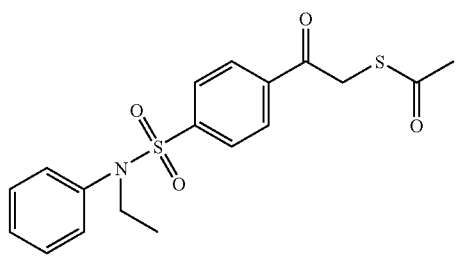

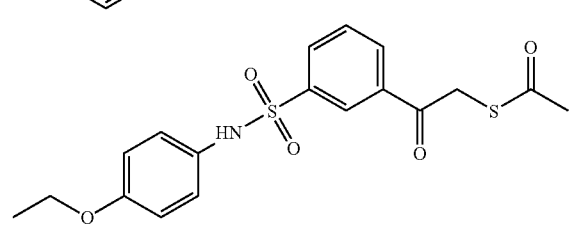

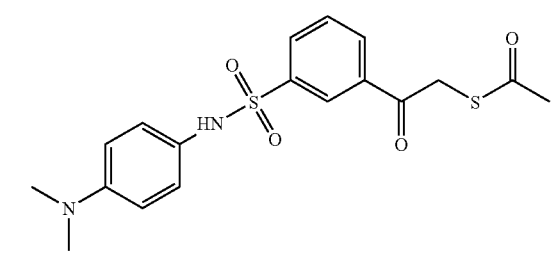

-continued
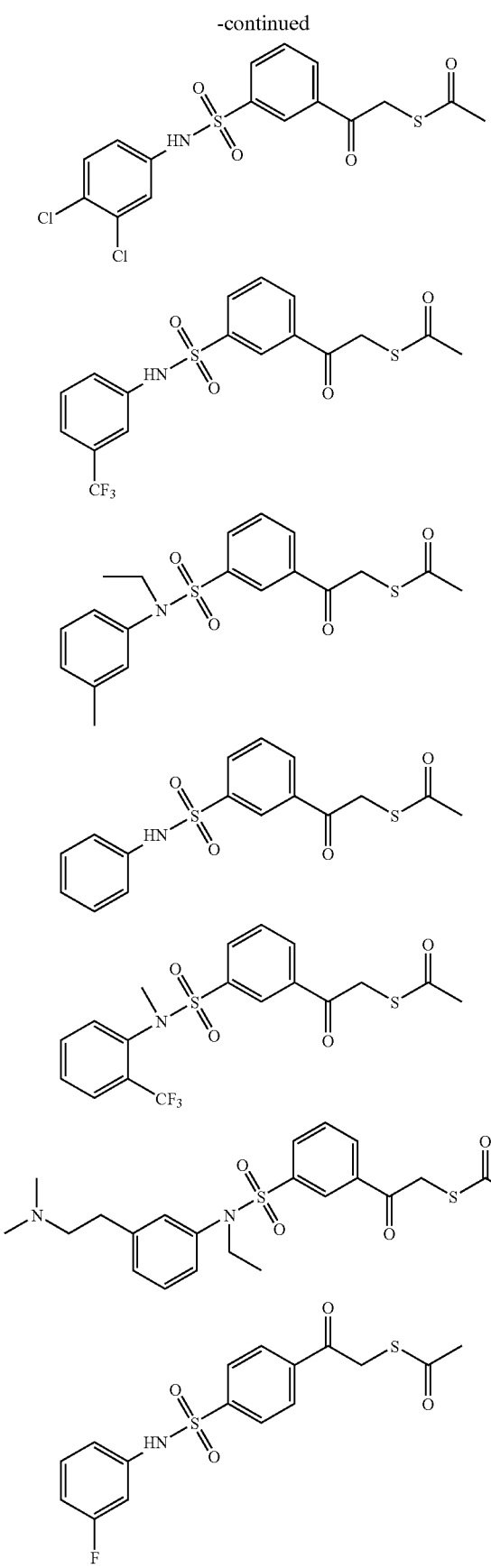
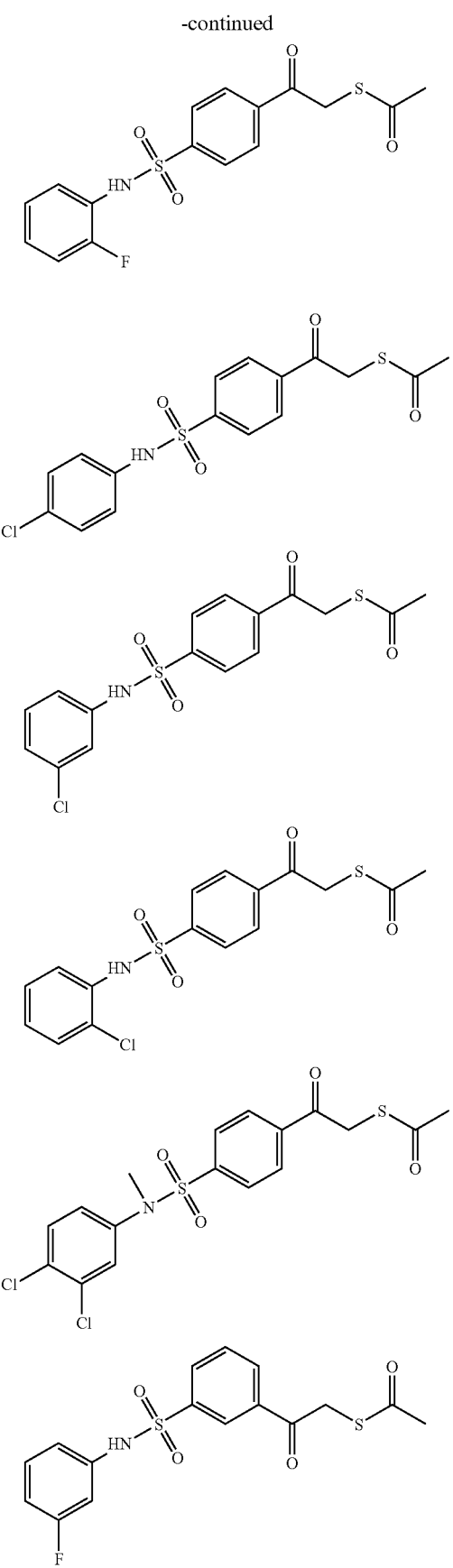

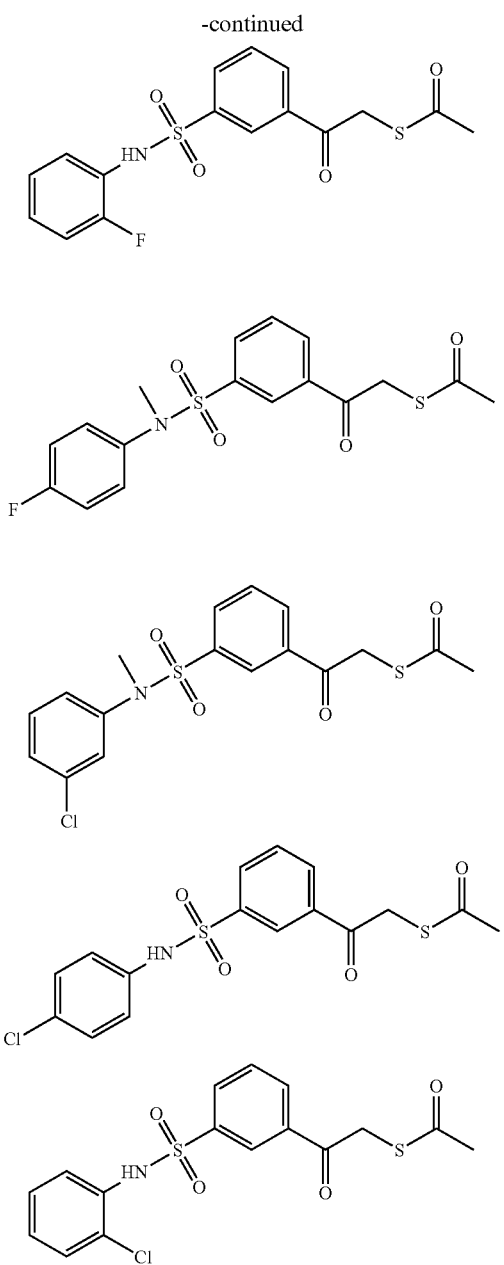

In certain embodiments wherein compounds have Structure (I) as described above, $G_1$ is an optionally substituted phenyl having structure (IV) or (V), and G2 is S-sulfonamide moiety having structure (X) or (XI), $G_3$ can be a 5 or 6 membered heteroaromatic optionally substituted by $X_3$, $X_4$, $X_5$ as shown below:

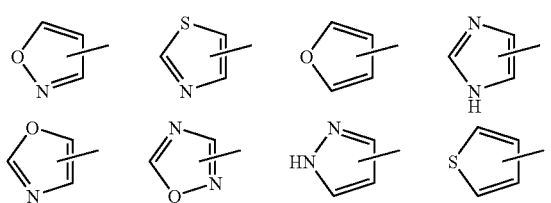

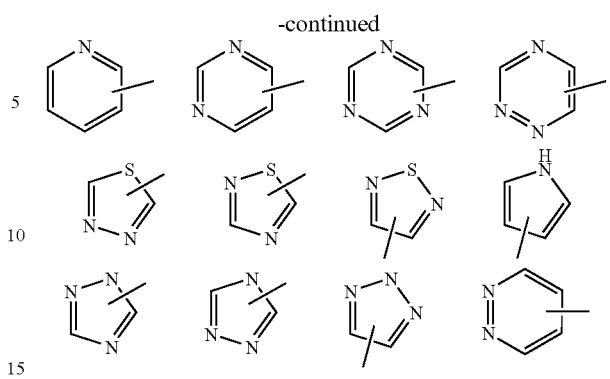

wherein X3, X4 and X5 are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl.

In certain embodiments of the compounds described in the preceding paragraph, wherein compounds have Structure (I) as described above, $G_1$ is an optionally substituted phenyl having structure (IV) or (V), and G2 is S-sulfonamide moiety having structure (X) or (XI), $G_3$ can be a 5 or 6 membered heteroaromatic optionally substituted by $X_3$, $X_4$, $X_5$ as described in the preceding paragraph, G4 is an optionally substituted acyl of the formula —C(O)$R_E$, wherein $R_E$ is any pharmaceutically acceptable acid; R1 and R2 are each independently hydrogen, lower alkyl or R1 and R2 taken together form optionally substituted cycloalkyl; and X1 and X2 are each independently selected from hydrogen, halogen, hydroxyl, lower alkyl, lower perhaloalkyl, lower alkoxy and lower perhaloalkoxy. R4 can be hydrogen, optionally substituted lower alkyl, or a structural element known to confer aqueous solubility. Particular embodiments include:
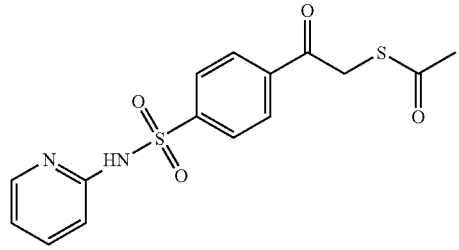
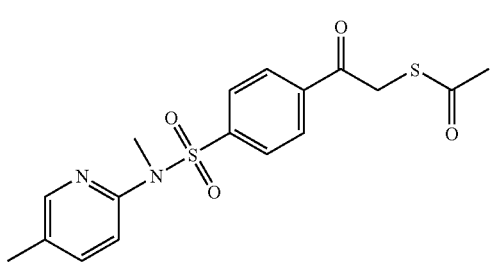
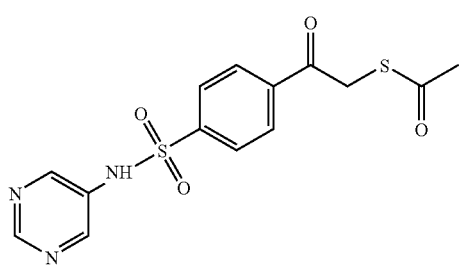
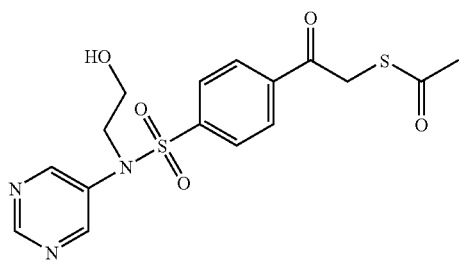
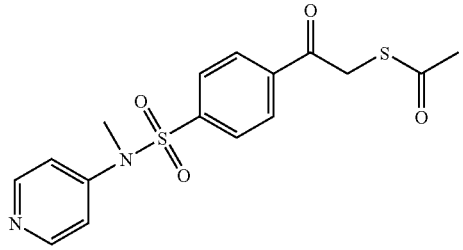
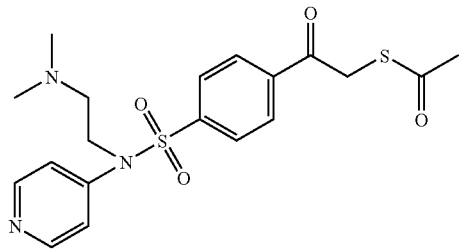
-continued
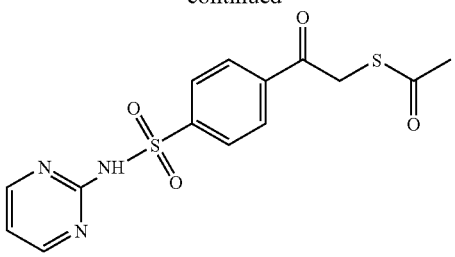
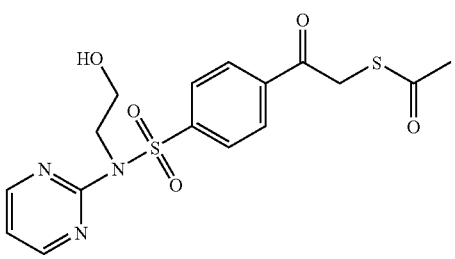
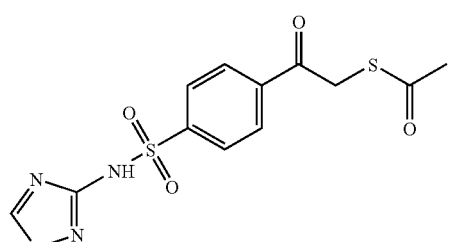
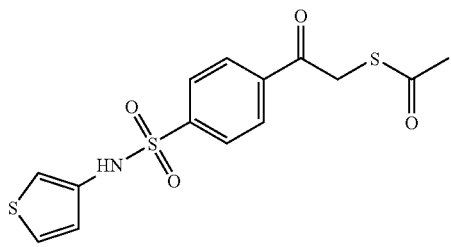
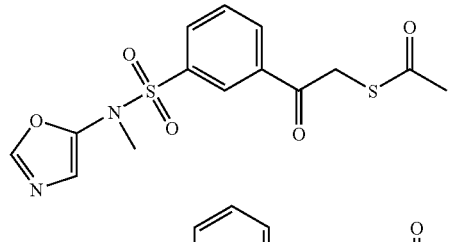
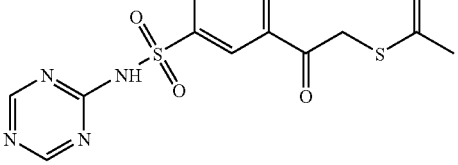
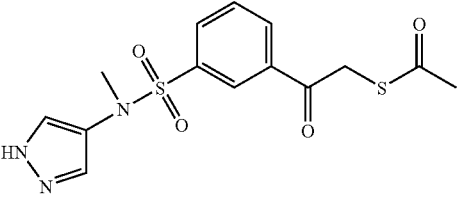

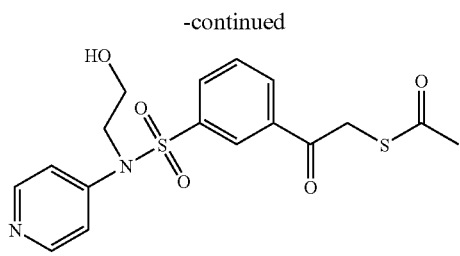

In certain embodiments wherein compounds have Structure (I) as described above, $G_1$ is an optionally substituted phenyl having structure (IV) or (V), and $G_2$ is S-sulfonamide moiety having structure (X) or (XI), $G_3$ can be an optionally substituted alkyl. In further embodiments, $G_4$ can be an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(O$R_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_4$ can be hydrogen, optionally substituted lower alkyl, or a structural element known to confer aqueous solubility. Particular embodiments include:

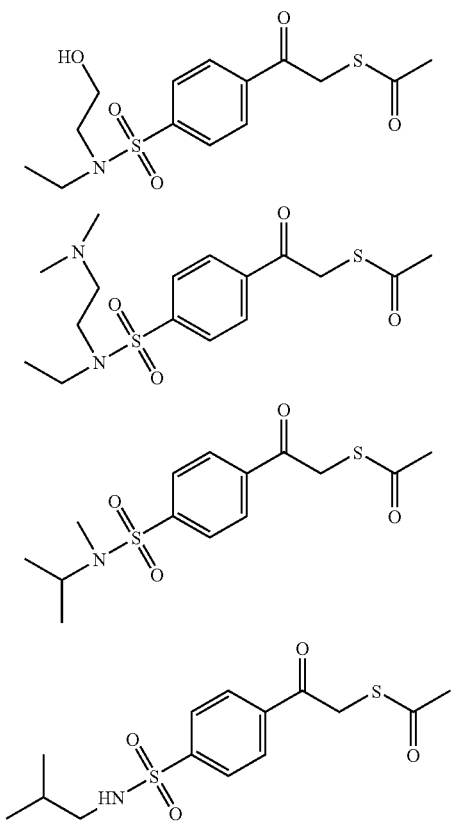

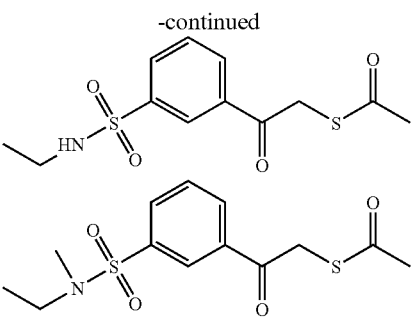

In certain embodiments of compounds having Structure (I) as described above, $G_1$ is a 5 or 6 membered heteroaromatic optionally substituted by $X_1$, $X_2$ of structure (XIV);

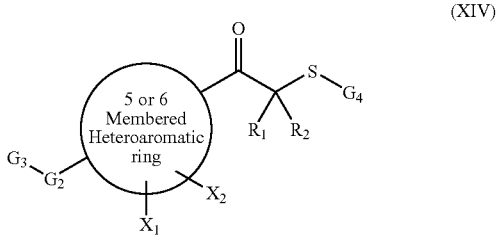

(XIV)

wherein $X_1$ and $X_2$ are each independently selected from the group consisting of hydrogen, halogen, hydroxyl, optionally substituted lower alkyl, optionally substituted lower alkoxy.

In certain embodiments, compounds have the structure of Formula (1) above, $G_1$ is a 5 or 6 membered heteroaromatic optionally substituted by $X_1$, $X_2$ of structure (XIV), and $G_2$ is a sulfonamide having an N-sulfonamide moiety of structure (XV) or an S-sulfonamide moeity of structure (XVI)

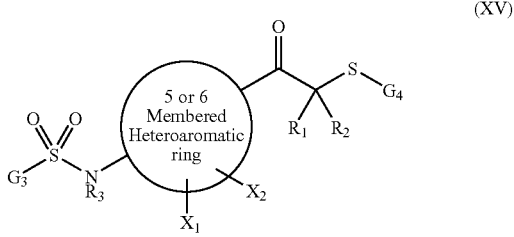

(XV)

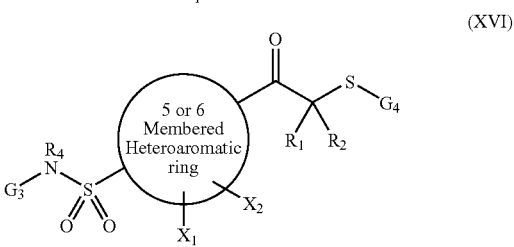

(XVI)

In certain embodiments, compounds have the structure of Formula (1) above, $G_1$ is a 5 or 6 membered heteroaromatic optionally substituted by $X_1$, $X_2$ of structure (XIV), $G_2$ is an N-sulfonamide moiety having structure (XV) or S-sulfonamide (XVI), and G3 is an optionally substituted phenyl of structure (XVII):

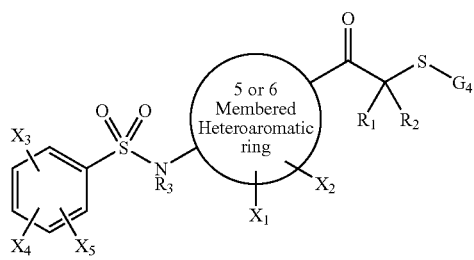

(XVII)

wherein X₃, X₄ and X₅ are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, or aminothiocarbonylaminoalkyl.

In certain embodiments, compounds have the structure of Formula (1) above, G₁ is a 5 or 6 membered heteroaromatic optionally substituted by X₁, X₂ of structure (XIV), G₂ is an N-sulfonamide moiety having structure (XV) or S-sulfonamide (XVI), and G₃ is an optionally substituted phenyl of structure (XVII), and X₃, X₄ and X₅ are selected as described in the preceding paragraph, G₄ can be an optionally substituted acyl of the formula —C(O)R_E, wherein R_E is any pharmaceutically acceptable acid, an optionally substituted alkylthiol, wherein G₄ taken in combination with sulfur, forms a disulfide, and —P(O)(OR₅)₂ or —P(O)(OH)₂, wherein G₄ taken in combination with sulfur, forms a phosphorothioate diester or phosphorothioate; R₁ and R₂ are each independently hydrogen, lower alkyl or R₁ and R₂ taken together form optionally substituted cycloalkyl; and X₁ and X₂ are each independently selected from hydrogen, halogen, hydroxyl, lower alkyl, lower perhaloalkyl, lower alkoxy and lower perhaloalkoxy. R₃ can be hydrogen, optionally substituted lower alkyl, or a structural element known to confer aqueous solubility. In these embodiments, G₁ can be any of:

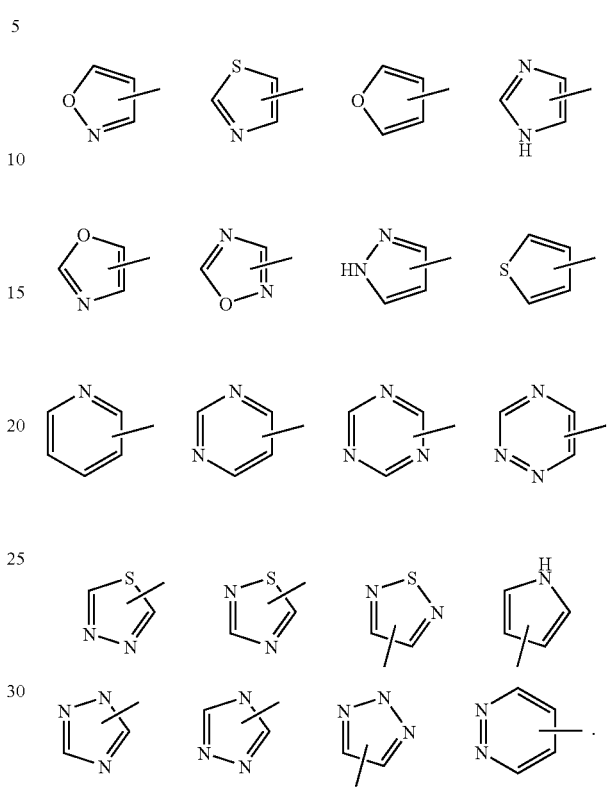

Particular embodiments include:

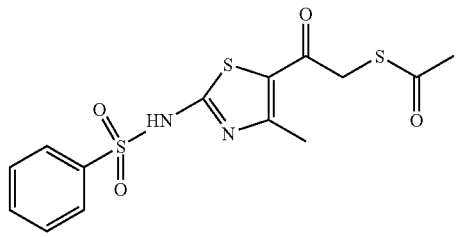

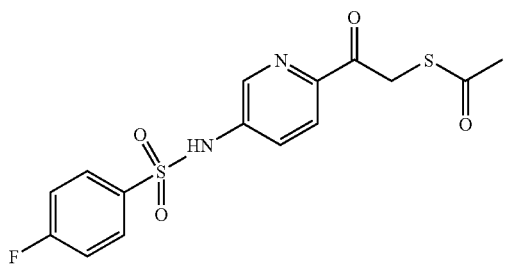

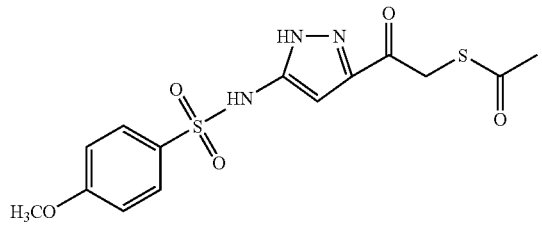

-continued

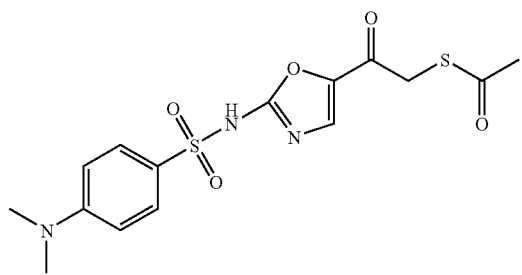

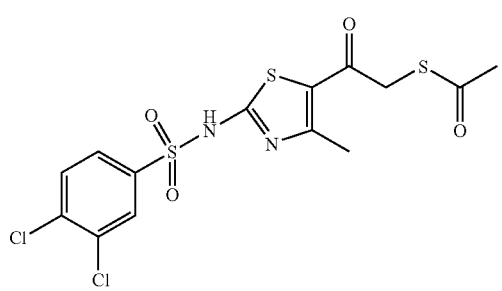

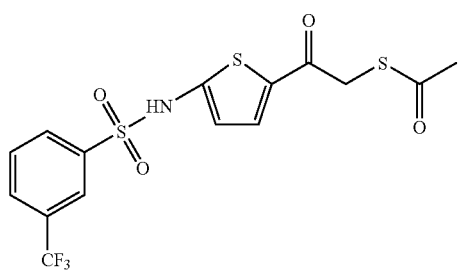

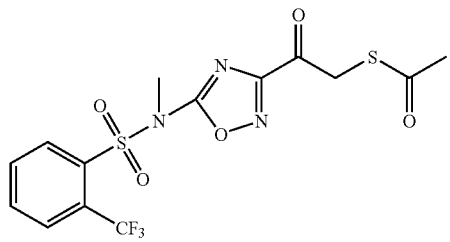

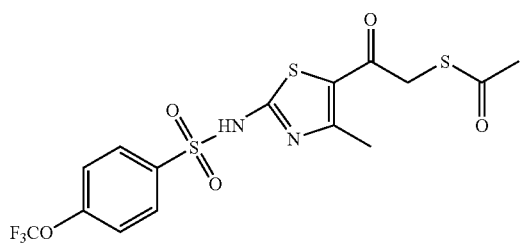

In certain embodiments, compounds have the structure of Formula (1) above, $G_1$ is a 5 or 6 membered heteroaromatic optionally substituted by $X_1$, $X_2$ of structure (XIV), $G_2$ is an N-sulfonamide moiety having structure (XV) or S-sulfonamide (XVI), and G3 can be a 5 or 6 membered heteroaromatic optionally substituted by $X_3$, $X_4$, $X_5$ of structure (XVIII)

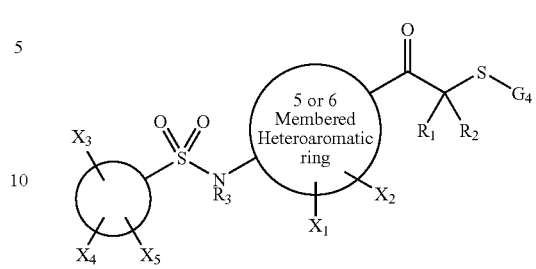

wherein X3, X4 and X5 are each independently chosen from a group consisting of hydrogen, perhaloaryloxy, alkanoylalkyl, N-aryl-N-alkyl amino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, or aminothiocarbonylaminoalkyl.

In certain embodiments, compounds have the structure of Formula (1) above, $G_1$ is a 5 or 6 membered heteroaromatic optionally substituted by $X_1$, $X_2$ of structure (XIV), $G_2$ is an N-sulfonamide moiety having structure (XV) or S-sulfonamide (XVI), and $G_3$ is can be a 5 or 6 membered heteroaromatic optionally substituted by $X_3$, $X_4$, $X_5$ of structure (XVIII), with $X_3$, $X_4$ and $X_5$ selected as described in the preceding paragraph, $G_4$ can be an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(OR$_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_3$ can be hydrogen, optionally substituted lower alkyl, or a structural element known to confer aqueous solubility. In these embodiments, $G_3$ can be:

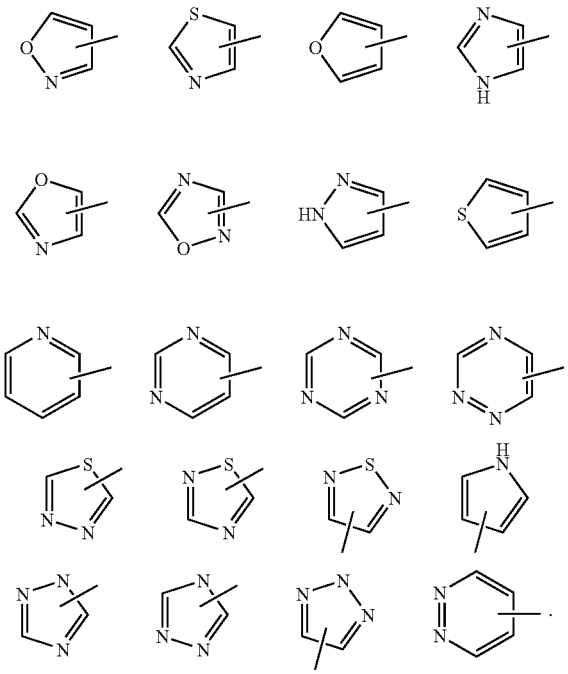

Particular embodiments include:

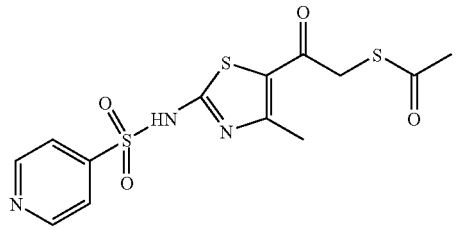

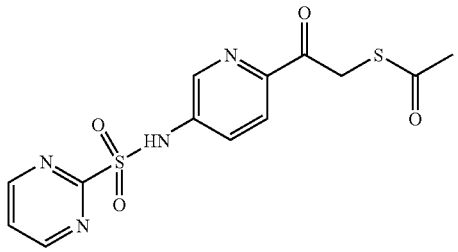

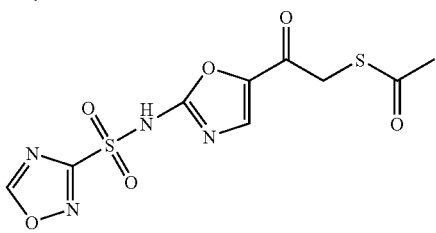

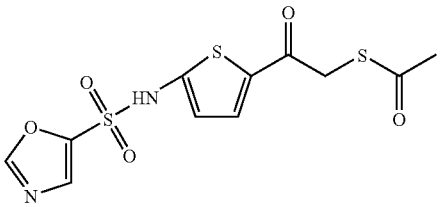

In certain embodiments, compounds have the structure of Formula (1) above, $G_1$ is a 5 or 6 membered heteroaromatic optionally substituted by $X_1$, $X_2$ of structure (XIV), and $G_2$ is an N-sulfonamide moiety having structure (XV), wherein $G_3$ comprises an optionally substituted alkyl.

(XV)

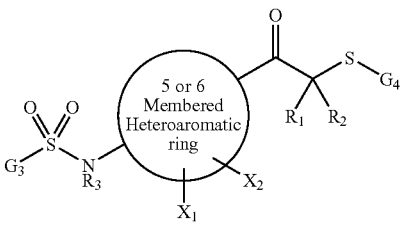

In certain embodiments, compounds have the structure of Formula (1) above, $G_1$ is a 5 or 6 membered heteroaromatic optionally substituted by $X_1$, $X_2$ of structure (XIV), $G_2$ is an N-sulfonamide moiety having structure (XV), G3 comprises an optionally substituted alkyl, and $G_4$ is an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(OR$_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_3$ can be hydrogen, optionally substituted lower alkyl, or a structural element known to confer aqueous solubility. In certain embodiments, $G_1$ can be:

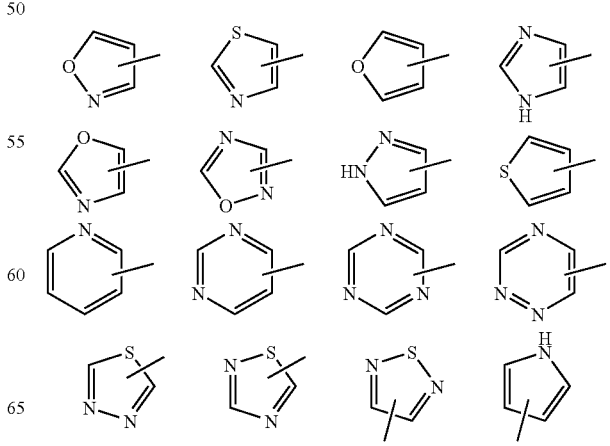

-continued

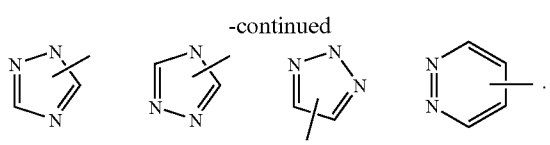

Particular embodiments include:

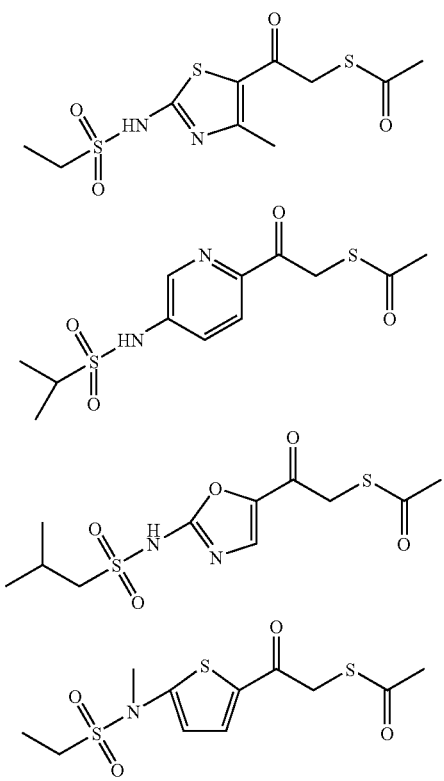

In certain embodiments, compounds have the structure of Formula (1) above, $G_1$ is a 5 or 6 membered heteroaromatic optionally substituted by $X_1$, $X_2$ of structure (XIV), $G_2$ is an N-sulfonamide moiety having structure (XV) or S-sulfonamide (XVI), and G3 is an optionally substituted phenyl of structure (XIX):

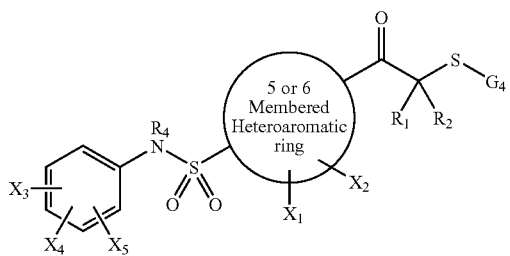

wherein $X_3$, $X_4$ and $X_5$ are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbo- nylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, aminothiocarbonylaminoalkyl.

In certain embodiments, compounds have the structure of Formula (1) above, $G_1$ is a 5 or 6 membered heteroaromatic optionally substituted by $X_1$, $X_2$ of structure (XIV), G2 is an N-sulfonamide moiety having structure (XV) or S-sulfonamide (XVI), $G_3$ is an optionally substituted phenyl of structure (XIX) as described in the preceding paragraph, and $G_4$ is an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(OR$_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_4$ can be hydrogen, optionally substituted lower alkyl, or a structural element known to confer aqueous solubility. In further embodiments, $G_1$ can be:

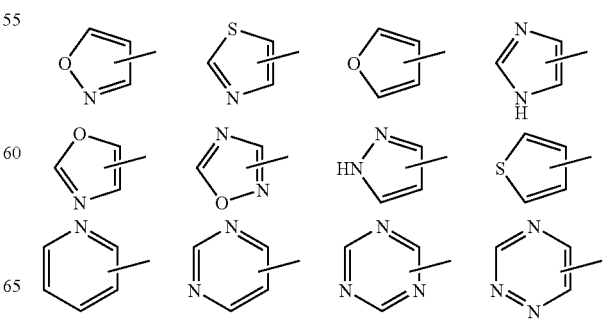

-continued

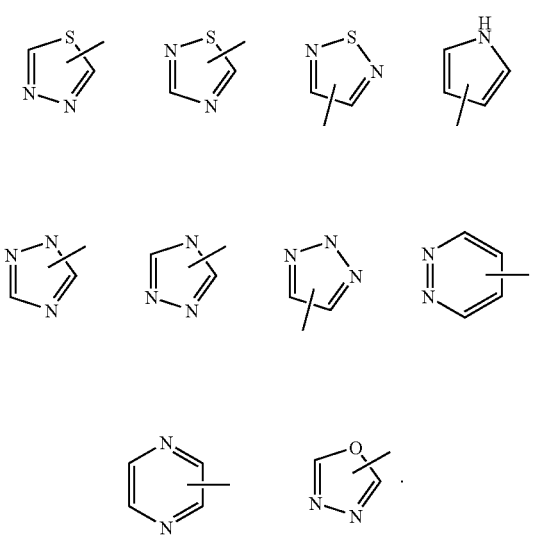

Particular embodiments include:

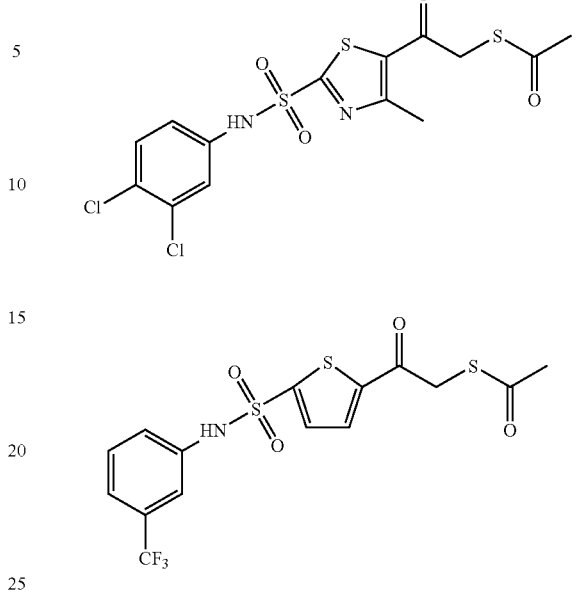

-continued

In certain embodiments, compounds have the structure of Formula (1) above, $G_1$ is a 5 or 6 membered heteroaromatic optionally substituted by $X_1$, $X_2$ of structure (XIV), $G_2$ is a S-sulfonamide (XVI), and G3 is a 5 or 6 membered optionally substituted heteroaromatic of structure (XVIII), $G_3$ can be a 5 or 6 membered heteroaromatic optionally substituted by $X_3$, $X_4$, $X_5$ of structure (XX)

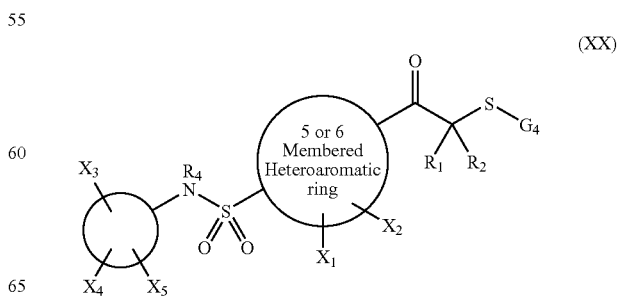

(XX)

wherein X3, X4 and X5 are each independently chosen from a group consisting of hydrogen, perhaloaryloxy, alkanoylalkyl, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, heterocyclylcarbonyl, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, heteroarylthio, heteroarylsulfonyl, heterocyclylsulfonyl, arylsulphonyl, heteroarylsulfonyl, heterocyclylsulphonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, saturated heterocyclyl, heteroaryl, heteroaryloxy, heteroaryloxyalkyl, heteroaralkyl, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, or aminothiocarbonylaminoalkyl.

In certain embodiments, compounds have the structure of Formula (1) above, $G_1$ is a 5 or 6 membered heteroaromatic optionally substituted by $X_1$, $X_2$ of structure (XIV), $G_2$ is a S-sulfonamide (XVI), and G3 is a 5 or 6 membered optionally substituted heteroaromatic of structure (XVIII), $G_3$ can be a 5 or 6 membered heteroaromatic optionally substituted by $X_3$, $X_4$, $X_5$ of structure (XX), and G4 is an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(OR$_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_4$ can be hydrogen, optionally substituted lower alkyl, or a structural element known to confer aqueous solubility. In further embodiments, $G_1$ and $G_3$ can each be independently selected from:

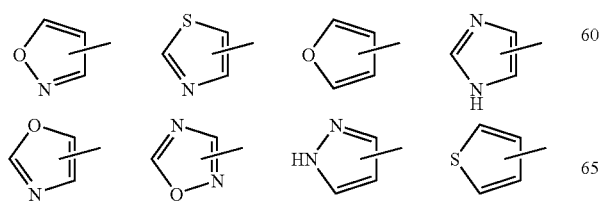

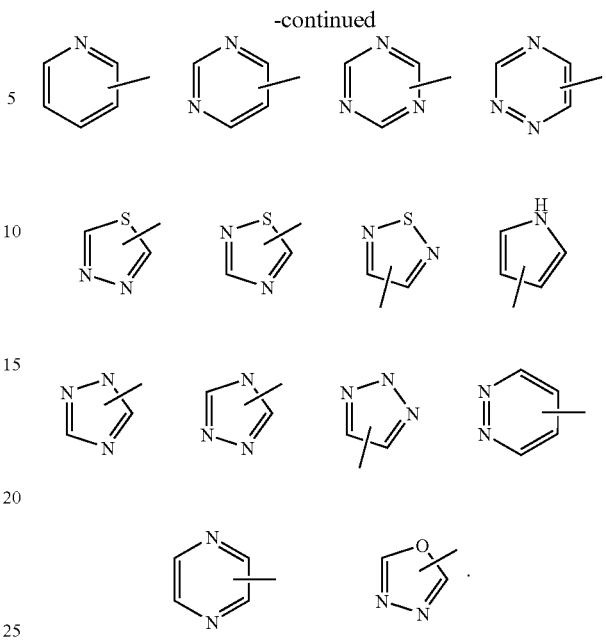

Particular embodiments include:

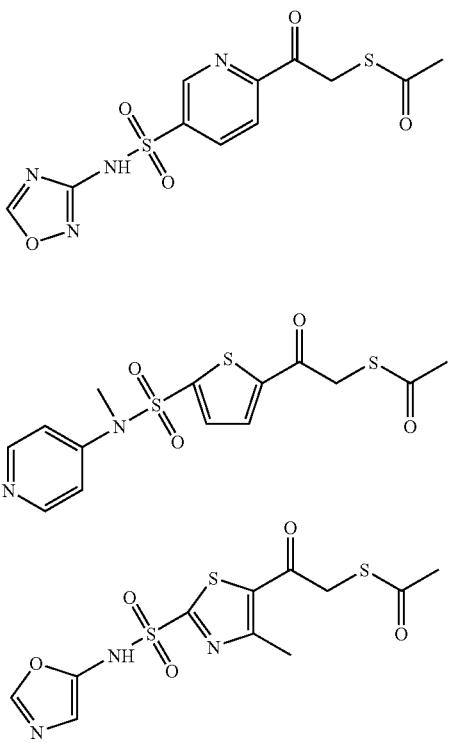

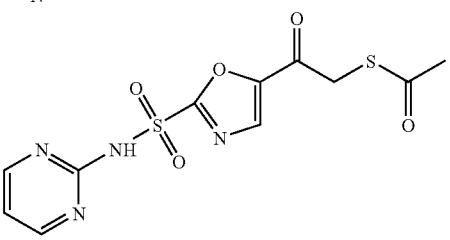

In certain embodiments, compounds have the structure of Formula (1) above, $G_1$ is a 5 or 6 membered heteroaromatic optionally substituted by $X_1$, $X_2$ of structure (XIV), $G_2$ is an S-sulfonamide (XVI), and G3 is an optionally substituted alkyl.

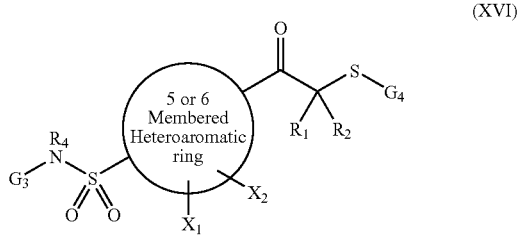

In certain embodiments, compounds have the structure of Formula (1) above, $G_1$ is a 5 or 6 membered heteroaromatic optionally substituted by $X_1$, $X_2$ of structure (XIV), $G_2$ is an S-sulfonamide (XVI), G3 is an optionally substituted alkyl, and G4 is an optionally substituted acyl of the formula —C(O)$R_E$, wherein $R_E$ is any pharmaceutically acceptable acid, an optionally substituted alkylthiol, wherein $G_4$ taken in combination with sulfur, forms a disulfide, and —P(O)(O$R_5$)$_2$ or —P(O)(OH)$_2$, wherein $G_4$ taken in combination with sulfur, forms a phosphorothioate diester or phosphorothioate; $R_1$ and $R_2$ are each independently hydrogen, lower alkyl or $R_1$ and $R_2$ taken together form optionally substituted cycloalkyl; and $X_1$ and $X_2$ are each independently selected from hydrogen, halogen, hydroxyl, lower alkyl, lower perhaloalkyl, lower alkoxy and lower perhaloalkoxy. $R_4$ can be hydrogen, optionally substituted lower alkyl, or a structural element known to confer aqueous solubility. In further embodiments, $G_1$ can be:

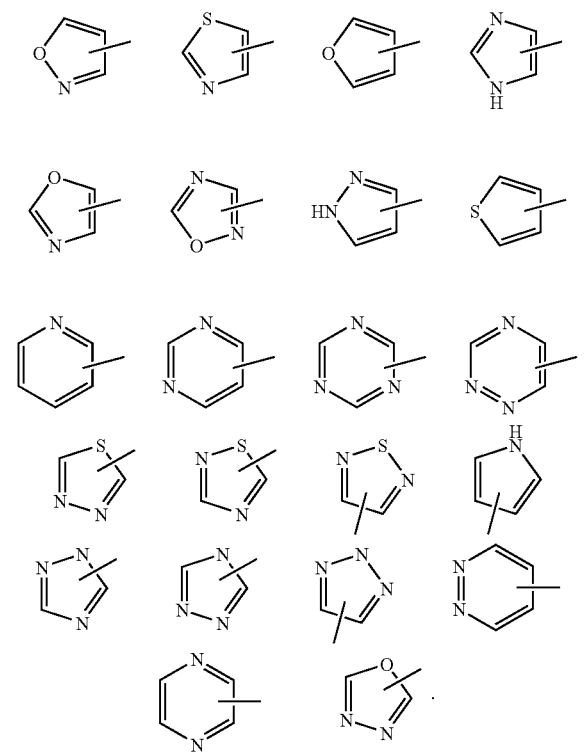

Particular embodiments include:

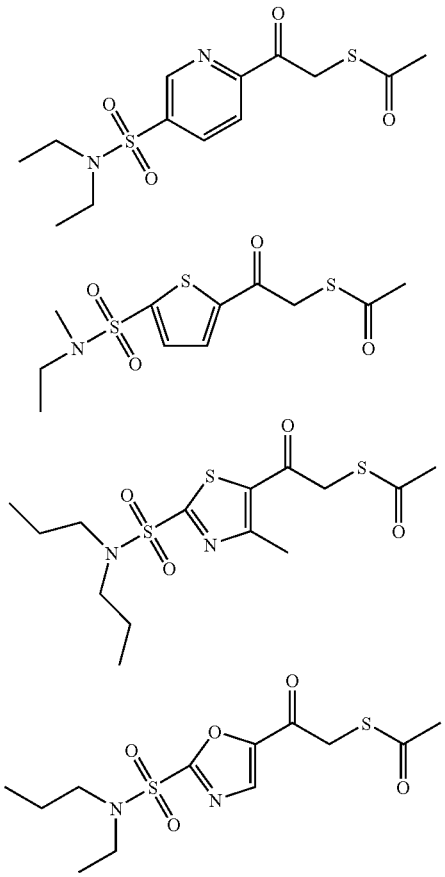

In one embodiment, a compound having the structure of Formula (1), has the structure consisting of:

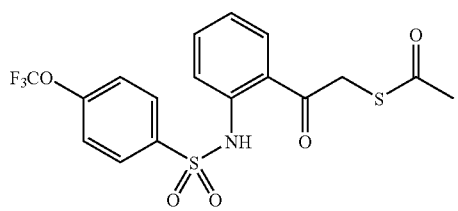

In another aspect, the invention relates to a compound selected from the goup consisting of the compounds set forth in the examples, or a pharmaceutically acceptable salt, ester, amide, or prodrug thereof:

Exemplary compounds and pharmaceutically acceptable esters or prodrugs thereof the invention include, but are not limited to, disulfide dimers, mercaptans, and thioesters of compounds of Formula (I).

Uses of Compounds of the Invention

In accordance with one aspect, the present invention provides compounds of Formula (I), where each compound is capable of inhibiting the catalytic activity of histone deacetylase (HDAC). In another aspect, the present invention provides pharmaceutical compositions comprising compounds of Formula (I), capable of inhibiting the catalytic activity of histone deacetylase (HDAC).

In accordance with another aspect, the present invention provides compounds of Formula (1), capable of inhibiting the cellular function of HDAC. In another aspect, the present invention provides pharmaceutical compositions comprising compounds of Formula (I), capable of inhibiting the cellular function of histone deacetylase (HDAC).

In accordance with yet another aspect of the invention, the present invention provides methods and compositions for treating certain diseases or disease states. Methods and compositions are provided for using compounds of the invention for treating diseases or disease states including, but not limited to, cancers, autoimmune diseases, tissue damage, central nervous system disorders, neurodegenerative disorders, fibrosis, bone disorders, and disorders in which angiogenesis play a role in pathogenesis.

In accordance with one aspect, methods and compositions of the invention are used for treating cancer. In some embodiments, but without limitation, the term cancer refers to and is selected from disorders such as colon cancer, breast cancer, ovarian cancer, lung cancer and prostrate cancer, tumor invasion, tumor growth, tumor metastasis, and cancers of the oral cavity and pharynx (lip, tongue, mouth, pharynx), esophagus, stomach, small intestine, large intestine, rectum, liver and biliary passages, pancreas, larynx, bone, connective tissue, skin, cervix uteri, corpus endometrium, testis, bladder, kidney and other urinary tissues, eye, brain and central nervous system, thyroid and endocrine gland. The term "cancer" also encompasses Hodgkin's disease, non-Hodgkin's lymphomas, multiple myeloma and hematopoietic malignancies including leukemias (Chronic Lymphocytic Leukemia) and lymphomas including lymphocytic, granulocytic and monocytic. Additional types of cancers which may be treated using the compounds and methods of the invention include, but are not limited to, adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, cancer of the larynx, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

In accordance with another aspect, methods and compositions of the invention are used for preventing neoplasias including, but not limited to, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. The neoplasia can be selected from gastrointestinal cancer, liver cancer, bladder cancer, pancreas cancer, ovary cancer, prostate cancer, cervical cancer, lung cancer, breast cancer and skin cancer, such as squamous cell and basal cell cancers.

In accordance with another aspect, methods and compositions of the invention are used for treating autoimmune diseases including, but not limited to: autoimmune disease that targets the nervous system, e.g., multiple sclerosis, myasthenia gravis, autoimmune neuropathies such as Guillain-Barre syndrome, autoimmune uveitis; autoimmune disease that targets the gastrointestinal system, e.g., Crohn's disease, ulcerative colitis, primary biliary cirrhosis; autoimmune hepatitis; autoimmune disease that targets the blood, e.g., autoimmune hemolytic anemia, pernicious anemia, autoimmune thrombocytopenia; autoimmune disease that targets endocrine glands, e.g., Type 1 or immune-mediated diabetes mellitus, Grave's disease, Hashimoto's thyroiditis, autoimmune oophoritis and orchitis, autoimmune disease of the adrenal gland; autoimmune disease that targets blood vessels, e.g., temporal arteritis, anti-phospholipid syndrome, vasculitides such as Wegener's granulomatosis, Behcet's disease; autoimmune disease that targets multiple organs including the musculoskeletal system, e.g., rheumatoid arthritis, scleroderma, polymyositis, dermatomyositis, spondyloarthropathies such as ankylosing spondylitis, Sjogren's syndrome; autoimmune disease that targets skin, e.g., psoriasis, dermatitis herpetiformis, pemphigus vulgaris, or vitiligo.

In accordance with another aspect, methods and compositions of the invention are used for treating disease states characterized by tissue damage, where the disease states include, but are not limited to, vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like.

In accordance with another aspect, methods and compositions of the invention are used for treating the fibrosis which occurs with radiation therapy.

In accordance with another aspect, methods and compositions of the invention are used for treating subjects having adenomatous polyps, including those with familial adenomatous polyposis (FAP). Additionally, the present compounds and methods can be used to prevent polyps from forming in patients at risk of FAP.

In accordance with another aspect, methods and compositions of the invention are used for treating anemias or thalassemias including, without limitation, sickle cell anemia.

In accordance with another aspect, methods and compositions of the invention are used for treating a cardiovascular condition, e.g., cardiac hypertrophy and heart failure.

In accordance with another aspect, methods and compositions of the invention are used for treating diseases related to an inflammatory condition including, but not limited to, rheumatoid arthritis (RA), inflammatory bowel disease (IBD), ulcerative colitis and psoriasis.

In accordance with another aspect, methods and compositions of the invention are used for treating certain central nervous system disorders including, but not limited to, Parkinson's disease, Alzheimer's disease, Alzheimer's dementia, and central nervous system damage resulting from stroke, ischemia and trauma.

In accordance with another aspect, methods and compositions of the invention are used for treating a neurological or polyglutamine-repeat disorder including, but not limited to, Huntington's disease, Spinocerebellar ataxia 1 (SCA 1), Machado-Joseph disease (MJD)/Spinocerebella ataxia 3 (SCA 3), Kennedy disease/Spinal and bulbar muscular atrophy (SBMA) and Dentatorubral pallidolusyian atrophy (DRPLA).

In accordance with another aspect, methods and compositions of the invention are used for treating neurodegenerative disorders in which HDAC inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Amyotrophic Lateral Sclerosis, Korsakoffs disease, imbecility relating to a cerebral vessel disorder, sleeping disorders, schizophrenia, depression, depression or other symptoms associated with Premenstrual Syndrome (PMS), anxiety and septic shock.

In accordance with another aspect, methods and compositions of the invention are used for treating bone diseases, including bone disorders involving osteoclasts and chonrocytes. Without wishing to be limited by this theory, it is noted that HDAC activity regulates the process of osteoclastogenesis and chondrocyte differentiation, such that inhibitors of HDAC are also useful in the treatment of all bone disorders involving osteoclasts and chondrocytes.

In accordance with another aspect, methods and compositions of the invention are used for treating ophthalmic diseases and other diseases in which angiogenesis plays a role in pathogeneis, such as glaucoma, retinal ganglion degeneration, occular ischemia, retinitis, retinopathies, uveitis, ocular photophobia, and of inflammation and pain associated with acute injury to the eye tissue.

Methods and compositions of the invention are used for treating human and non-human subjects. Methods and compositions of the invention are suitable for veterinary uses in treating companion animals, exotic animals and farm animals, including mammals, rodents, and the like. In particular embodiments, methods and compositions of the invention are used for treating horses, dogs,and cats.

The terms "treat" or "treating" or "therapy" as used herein refer to (1) reducing the rate of progress of a disease, or, in case of cancer reducing the size of the tumor; (2) inhibiting to some extent further progress of the disease, which in case of cancer may mean slowing to some extent, or preferably stopping, tumor metastasis or tumor growth; and/or, (3) relieving to some extent (or, preferably, eliminating) one or more symptoms associated with the disease. Thus, the term "therapeutically effective amount" as used herein refers to that amount of the compound being administered which will provide therapy or affect treatment.

In accordance with certain aspects of the invention, the compounds of the present invention act as anti-tumor compounds and/or inhibit the growth of a tumor, i.e., they are tumor-growth-inhibiting compounds. The terms "anti-tumor" and "tumor-growth-inhibiting," when modifying the term "compound," and the terms "inhibiting" and "reducing", when modifying the terms "compound" and/or "tumor," mean that the presence of the subject compound is correlated with at least the slowing of the rate of growth of the tumor. More preferably, the terms "anti-tumor," "tumor-growth-inhibiting," "inhibiting," and "reducing" refer to a correlation between the presence of the subject compound and at least the temporary cessation of tumor growth. The terms "anti-tumor," "tumor-growth-inhibiting," "inhibiting," and "reducing" also refer to, a correlation between the presence of the compound(s) of the invention and at least the temporary reduction in the mass of the tumor. It is understood that the effectiveness of compounds of the invention as anti-tumor, or tumor-inhibiting, agents may be contribute to their effectiveness in treating cancer, but that the compound of the invention may also act through other mechanisms to exert measured effects on cancer.

The term "cellular function" refers to the function of HDAC in the cell. The term "HDAC function" is generally understood to refer to interaction of HDAC with a natural binding partner, and is particularly understood to refer to catalytic activity. The "cellular function" of HDAC is understood to refer not only to the catalyic activity of HDAC in a cell, but also to the cellular effects of HDAC catalytic activity on the function of the cell. The term "catalytic activity", in the context of the invention, defines the rate at which HDAC deacetylates a substrate. Catalytic activity can be measured, for example, by determining the amount of a substrate converted to a product as a function of time. Deacetylation of a substrate occurs at the active-site of HDAC. The active-site is normally a cavity in which the substrate binds to HDAC and is deacetylated.

The term "substrate" as used herein refers to a molecule deacetylated by HDAC. The substrate is preferably a peptide and more preferably a protein. In some embodiments, the protein is a histone, whereas in other embodiments, the protein is not a histone.

The term "inhibit" refers to decreasing the cellular function of HDAC. It is understood that compounds of the present invention may inhibit the cellular function of HDAC by various direct or indirect mechanisms, in particular by direct or indirect inhibition of the catalytic activity of HDAC. The term "activates" refers to increasing the cellular function of HDAC.

The term "modulates" refers to altering the function of HDAC by increasing or decreasing the probability that a complex forms between HDAC and a natural binding partner. A modulator may increase the probability that such a complex forms between HDAC and the natural binding partner, or may increase or decrease the probability that a complex forms between HDAC and the natural binding partner depending on the concentration of the compound exposed to HDAC, or may decrease the probability that a complex forms between HDAC and the natural binding partner. A modulator may activate the catalytic activity of HDAC, or may activate or inhibit the catalytic activity of HDAC depending on the concentration of the compound exposed to HDAC, or may inhibit the catalytic activity of HDAC.

The term "complex" refers to an assembly of at least two molecules bound to one another. The term "natural binding partner" refers to polypeptides that bind to HDAC in cells. A change in the interaction between HDAC and a natural binding partner can manifest itself as an increased or decreased probability that the interaction forms, or an increased or decreased concentration of HDAC/natural binding partner complex.

The term "contacting" as used herein refers to mixing a solution comprising a compound of the invention with a liquid medium bathing the cells of the methods. The solution comprising the compound may also comprise another component, such as dimethylsulfoxide (DMSO), which facilitates the uptake of the compound or compounds into the cells of the methods. The solution comprising the compound of the invention may be added to the medium bathing the cells by utilizing a delivery apparatus, such as a pipet-based device or syringe-based device.

The term "monitoring" refers to observing the effect of adding the compound to the cells of the method. The effect can be manifested in a change in cell phenotype, cell proliferation, HDAC catalytic activity, substrate protein acetylation levels, gene expression changes, or in the interaction between HDAC and a natural binding partner.

The term "effect" describes a change or an absence of a change in cell phenotype of cell proliferation. "Effect" can also describe a change or an absence of a change in the catalytic activity of HDAC. "Effect" can also describe a change or an absence of a change in an interaction between HDAC and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Changes or the absence of changes in cell phenotype are readily measured by techniques known in the art.

The present compounds are useful for identifying a carbonyl compounds that modulates the cellular function of HDAC, comprising the steps of:
a) contacting cells expressing HDAC with the disclosed compounds of and
b) measuring an effect of the compound or composition.
Optionally the effect is inhibition of the catalytic activity of HDAC. Further the methods of comprises measuring histone hyperacetylation. Additionally the effect is a change in cell phenotype and/or the effect is a change in cell proliferation.
Further the disclosed compounds can be used for the manufacture of a medicament for use in the treatment of a condition mediated by HDAC activity.

A. Pharmaceutical Compositions

The present invention also relates to a pharmaceutical composition comprising a compound of the invention, or a pharmaceutically acceptable salt, solvate, amide, ester, or prodrug thereof, as described herein. and a pharmaceutically acceptable carrier, diluent, or excipient, or a combination thereof.

The term "pharmaceutical composition" refers to a mixture of a compound of the invention with other chemical components, such as carriers, diluents or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" refers to relatively nontoxic chemical compounds or agents. Such carriers may facilitate the incorporation of a compound into cells or tissues. For example, human serum albumin (HSA) is a commonly utilized carrier as it facilitates the uptake of many organic compounds into the cells or tissues of an organism.

The term "diluent" refers to chemical compounds that are used to dilute the compound of interest prior to delivery. Diluents can also be used to stabilize compounds because they can provide a more stable environment. Salts dissolved in buffered solutions (providing pH control) are utilized as diluents in the art. One commonly used buffered solution is phosphate buffered saline. It is a buffer found naturally in the blood system. Since buffer salts can control the pH of a solution at low concentrations, a buffered diluent rarely modifies the biological activity of a compound.

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," 20th ed. Edited by Alfonso Gennaro, 2000.

1) Routes of Administration

Suitable routes of administration include local or systemic routes of administration including, but not limited to, topical, transdermal, oral, rectal, transmucosal, pulmonary, ophthalmic, intestinal, parenteral, intramuscular, subcutaneous, intravenous, intramedullary, intrathecal, direct intraventricular, intraperitoneal, intranasal, or intraocular delivery. In certain embodiments, compounds of the invention are administered topically, e,g in an ointment, patch, nasal spray, or eye drops/ointment. In certain embodiments, compounds of the invention are delivered by intestinal, parenteral, intramuscular, subcutaneous, intravenous, intramedullary, intrathecal, direct intraventricular, intraperitoneal, intranasal, or intraocular injections.

Alternately, one may administer the compound in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ.

2) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or compression processes.

Pharmaceutical compositions for use in accordance with the present invention thus may be formulated in conventional manner using one or more pharmaceutically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For intravenous injections, the agents of the invention may be formulated in aqueous solutions, preferably in pharmaceutically compatible buffers such as Hanks's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with pharmaceutically compatible buffers or excipients. Such excipients are generally known in the art.

For oral administration, the compounds can be formulated readily by combining the active compounds with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Dragee cores are provided with suitable coatings. For this purpose, concentrated agar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG-40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG-40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

GENERAL SYNTHETIC METHODS FOR PREPARING COMPOUNDS

Molecular embodiments of the present invention can be synthesized using standard synthetic techniques known to those of skill in the art. Compounds of the present invention can be synthesized using the general synthetic procedures set forth in Schemes I-III.

General procedure for sulfonamide (a): Scheme I

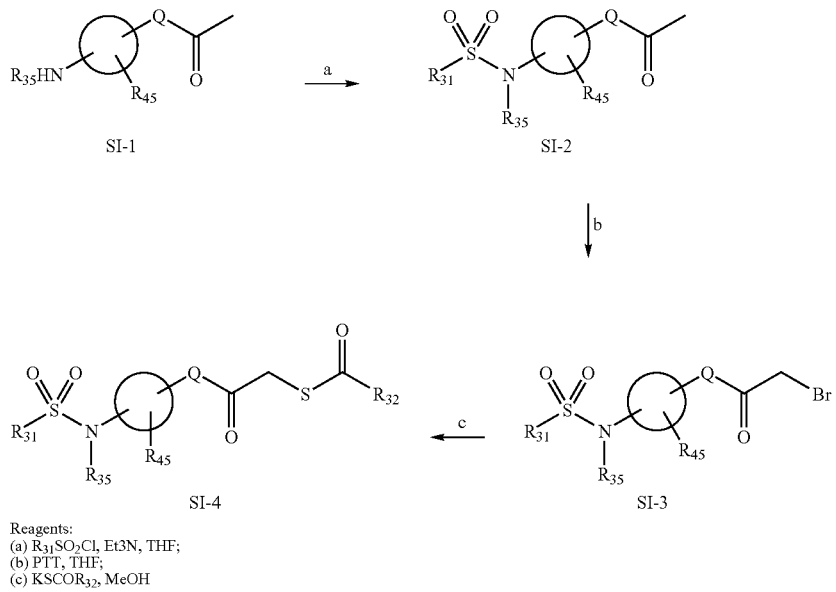

Reagents:
(a) $R_{31}SO_2Cl$, Et3N, THF;
(b) PTT, THF;
(c) $KSCOR_{32}$, MeOH

General procedure for sulfonamide (b): Scheme II

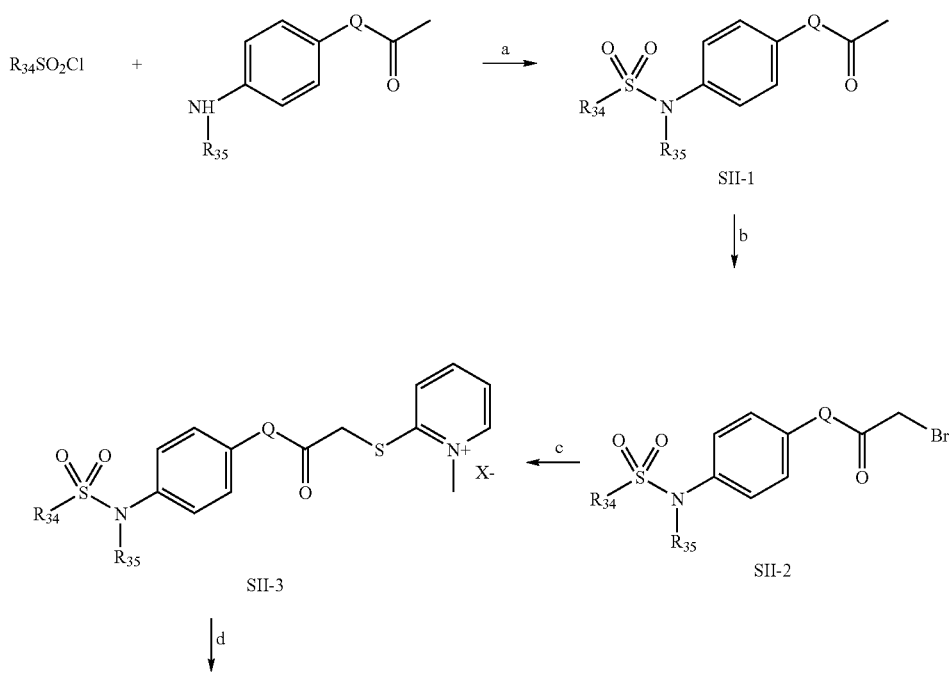

-continued
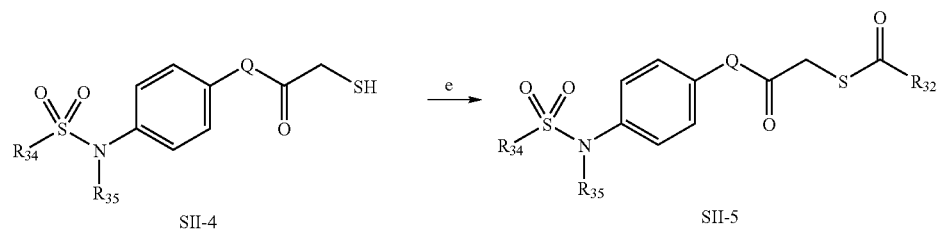
Reagents:
(a) pyridine, THF;
(b) PTT, THF;
(c) N-methyl 2-thiopyridone, EtOH;
(d) NaOH, water;
(e) acid chloride, hunig's base, DCM
General Procedure for reverse sulfonamide: Scheme III
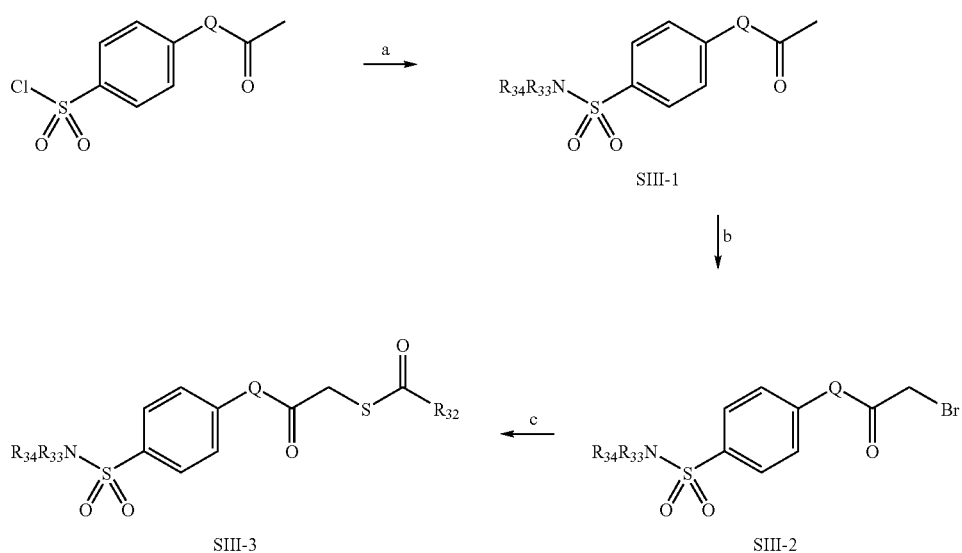
Reagents:
(a) Amine ($R_{34}R_{33}N$), THF, pyr;
(b) THF, PTT;
(c) MeOH, KSC(O)$R_{32}$
General Procedure for Ring-Fused Sulfonamides Scheme IV
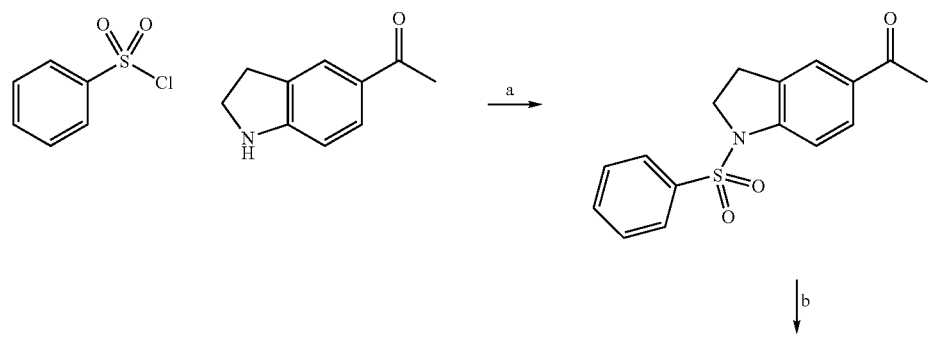

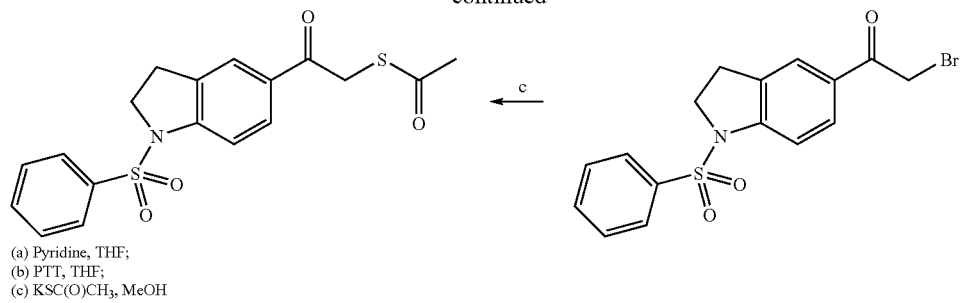

(a) Pyridine, THF;
(b) PTT, THF;
(c) KSC(O)CH₃, MeOH

Scheme V illustrates the general synthesis of disulfide embodiments of the present invention.

Scheme V

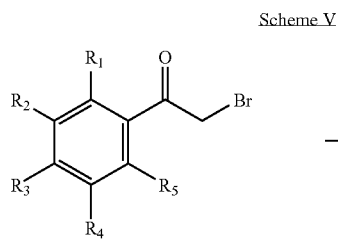

Reagents:
(a) KSC(O)CH₃, MeOH;
(b) NaOH, MeOH

Scheme VI depicts an alternative general scheme for the synthesis of thiol (mercaptan) and disulfide embodiments of the present invention

Scheme VI

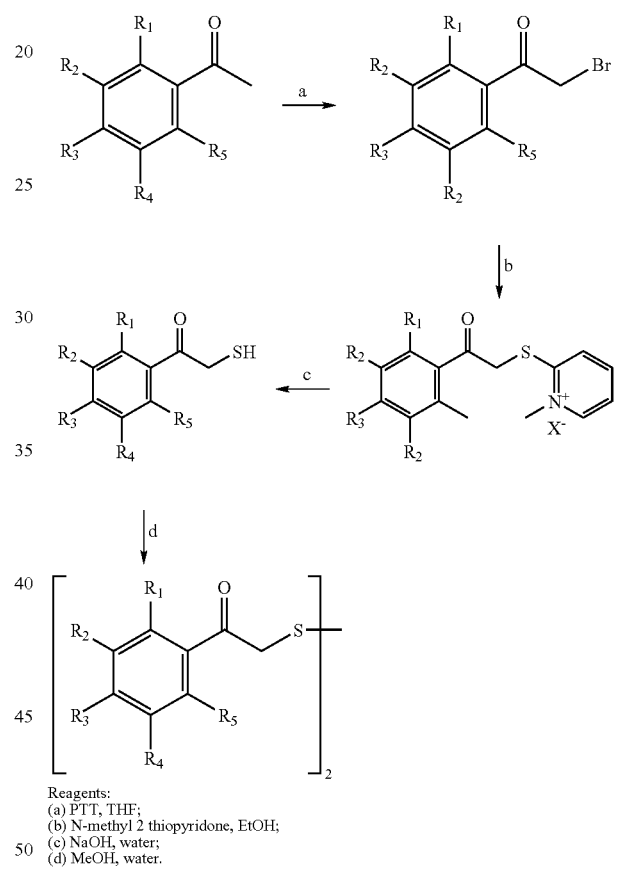

Reagents:
(a) PTT, THF;
(b) N-methyl 2 thiopyridone, EtOH;
(c) NaOH, water;
(d) MeOH, water.

EXAMPLES

The examples below are non-limiting and are merely representative of various aspects of the invention.

Example 1

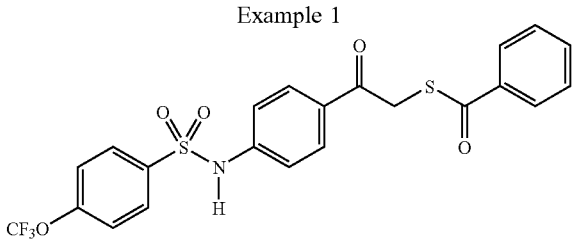

Thiobenzoic acid S-{2-oxo-2-[4-(4-trifluoromethoxy-benzenesulfonylamino)-phenyl]-ethyl}ester The compound thiobenzoic acid S-{2-oxo-2-[4-(4-trifluoromethoxy-benzenesulfonylamino)-phenyl]-ethyl}ester was synthesized according to Scheme I.

Step 1

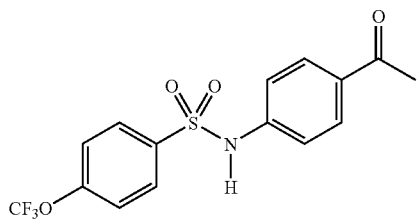

N-(4-Acetyl-phenyl)-4-trifluoromethoxy-benzenesulfonamide (SI-2)

4'-Amino acetophenone (0.375 g, 2.78 mmol) was dissolved in THF (5 ml) before pyridine (0.674 ml, 8.34 mmol) was added, leaving a yellow solution. 4-trifluoromethoxy benzenesulfonylchloride (0.871 g, 3.34 mmol) was then added dropwise with stirring. After stirring for 2 h, THF and pyridine were removed. The desired sulfonamide (0.848 g, 2.36 mmol, 85%) was recrystallized from ethyl acetate and hexanes. $^1$H-NMR: (400 MHz, CDCl$_3$) 7.89 (m, 4H), 7.29 (d, 1H), 7.16 (d, 2H), 6.88 (s, 1H), 2.55 (s, 3H). LC-MS (ES+): 360 [MH]$^+$ m/e.

Step 2

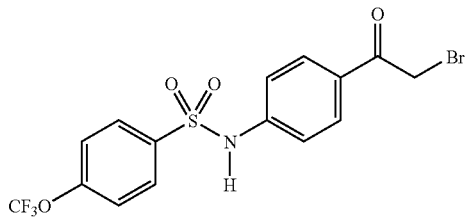

N-[4-(2-Bromo-acetyl)-phenyl]-4-trifluoromethoxybenzenesulfonamide (SI-3)

The ketone from step1 (0.32 g, 0.868 mmol) was dissolved in THF (9 ml), and phenyltrimethylammonium tribromide (PTT) (0.368 g, 0.868 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over Na$_2$SO$_4$ and evaporation leaves a white crystalline solid (90% desired mono-brominated material by LC-MS, 5% starting material, 5% dibrominated) suitable for the next step. LC-MS (ES–): 436, 438 m/e.

Step 3

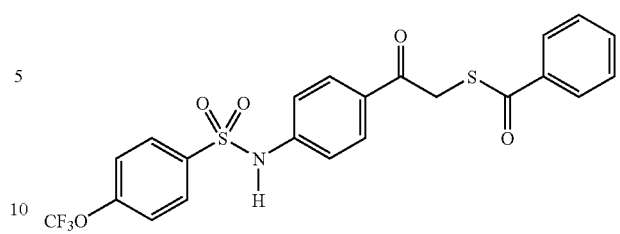

Thiobenzoic acid S-{2-oxo-2-[4-(4-trifluoromethoxy-benzenesulfonylamino)-phenyl]-ethyl}ester α-Bromoketone (SI-3) (0.3 g, 0.68 mmol) was dissolved in anhydrous THF (5 ml), and thiobenzoic acid (104 mg, 0.75 mmol) was added followed immediately by potassium carbonate (104 mg, 0.75 mmol). The reaction was stirred for 2 hours. The THF was evaporated and the residue was taken up in DCM and filtered. After evaporation of the DCM the product was purified by flash chromatography (7:3 EtOAC: hexanes). Removal of the solvent afforded 57 mg product (0.11 mmols, 16%) as a white solid. $^1$H-NMR: (400 MHz, DMSO): 8.00 (t, 3H), 7.98 (d, 2H), 7.61 (t, 2H), 7.50 (t, 2H), 7.32 (d, 2H), 7.22 (d, 2H), 4.52 (s, 2H); LC-MS (ES+): 496 [MH]$^+$ m/e.

Example 2

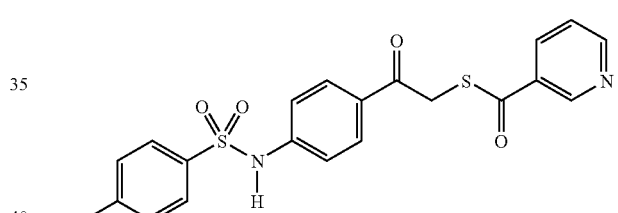

Thionicotinic acid S-{2-oxo-2-[4-(4-trifluorometlioxy-benzenesulfonylamino)-phenyl]-ethyl}ester Example 2 was synthesized according to the procedure outlined in Example 1. $^1$H-NMR: (400 MHz, CDCl$_3$): 9.11 (s, 1H), 8.86 (d, 1H), 8.30 (d, 1H), 8.00 (d, 2H), 7.98 (d, 2H), 7.44 (t, 1H), 7.33 (d, 2H), 7.28 (d, 2H), 4.60 (s, 2H); LC-MS (ES+): 498 m/e.

Example 3

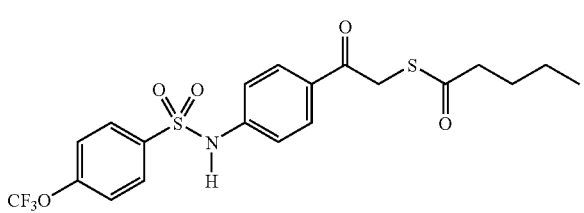

Pentanethioic acid S-{2-oxo-2-[4-(4-trifluoromethoxy-benzenesulfonylamino)-phenyl]-ethyl}ester Thioacetic acid S-{2-oxo-2-[4-(4-trifluoromethoxy-benzenesulfonylamino)-phenyl]-ethyl}ester (SI-4) (0.5 g, 1.15 mmol) was dissolved in anhydrous DMF (5 ml). Lithium hydroxide (28 mg, 1.15 mmol) was added and the solution was sonicated until homogeneous and heated to 90° C. for 4 hours. The solution was allowed to cool to room temperature and valeryl chloride (150 mg, 1.27 mmol) was added and the mixture stirred for 16 hours. The solution was partioned between 20 ml each water and EtOAc. The organic layer was washed with water, then brine and dried over $Na_2SO_4$. The solution was then filtered, stripped of solvent and the product purified by flash chromatography (100% DCM). The solvent was evaporated to afford 107 mg (0.22 mmol, 19%) product as a clear oil. $^1$H-NMR: (400 MHz, DMSO): 8.07 (d, 2H), 7.60 (d, 2H), 7.40 (d, 2H), 7.25 (d, 2H), 2.40 (s, 2H), 2.10 (t, 2H), 1.42 (t, 2H) 1.11 (t,2H), 0.09 (t, 3H); LC-MS (ES+): 476 [M]$^+$ m/e.

Example 4

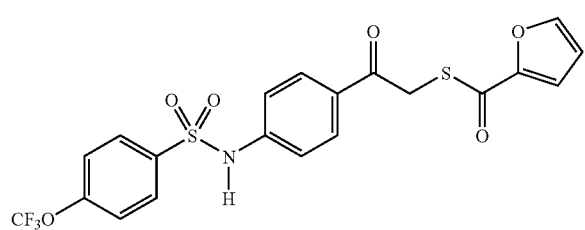

Furan-2-carbothioic acid S-{2-oxo-2-[4-(4-trifluoromethoxy-benzenesulfonylamino)-phenyl]-ethyl}ester The compound furan-2-carbothioic acid S-{2-oxo-2-[4-(4-trifluoromethoxy-benzenesulfonylamino)-phenyl]-ethyl}ester was synthesized according to Scheme II.

Step 1

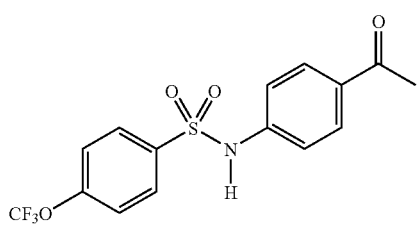

N-(4-Acetyl-phenyl)-4-trifluoromethoxy-benzenesulfonamide (SII-1)

4'-Amino acetophenone (0.375 g, 2.78 mmol) was dissolved in THF (5 ml) before pyridine (0.674 ml, 8.34 mmol) was added, leaving a yellow solution. 4-trifluoromethoxy benzenesulfonylchloride (0.871 g, 3.34 mmol) was then added dropwise with stirring. After removal of THF and pyridine, the desired sulfonamide (0.848 g, 2.36 mmol, 85%) was recrystallized from ethyl acetate and hexanes. $^1$H-NMR: (400 MHz, CDCl$_3$) 7.89 (m, 4H), 7.29 (d, 1H), 7.16 (d, 2H), 6.88 (s, 1H), 2.55 (s, 3H). LC-MS (ES+): 360 [MH]$^+$ m/e.

Step 2

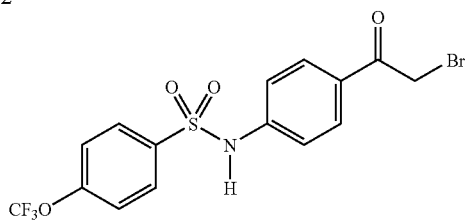

N-[4-(2-Bromo-acetyl)-phenyl]-4-trifluoromethoxy-benzenesulfonamide (SII-2)

The ketone from step 1 (0.32 g, 0.868 mmol) was dissolved in THF (9 ml), and phenyltrimethylammonium tribromide (PTT) (0.368 g, 0.868 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over Na$_2$SO$_4$ and evaporation leaves a white crystalline solid (90% desired mono-brominated material by LC-MS, 5% starting material, 5% dibrominated) suitable for the next step. LC-MS (ES-): 436, 438 m/e.

Step 3

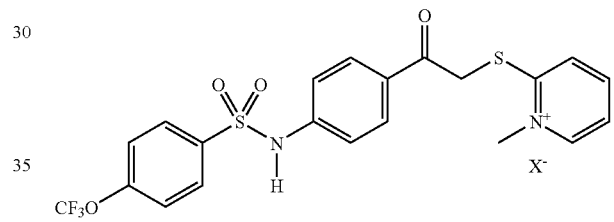

1-Methyl-2-{2-oxo-2-[4-(4-trifluoromethoxybenzene-sulphonylamino)phenyl]ethylsulfanyl}-pyridinium bromide (SII-3)

The bromoketone from step 2 (0.141 g crude material, 0.322 mmol) was dissolved in ethanol (2 ml) before N-methyl thiopyridone (0.040 g, 0.322 mmol) was added as a solid. The resulting yellow solution was then heated to reflux overnight. Evaporation of the volatiles leaves a residue (75% by NMR, 0.116 g, 0.240 mmol) suitable for the next step, however, the product may be recrystallized from ethanol if desired. $^1$H-NMR: (400 MHz, DMSO-d$_6$) 11.21 (s, 1H), 8.90 (d, 1H), 8.18 (t, 1H), 8.03 (m, 5H), 7.90 (t, 1H), 7.80 (d, 2H), 7.15 (d, 2H), 5.33 (s, 2H), 4.24 (s, 3H). LC-MS (ES+): 483 [M]$^+$ m/e.

Step 4

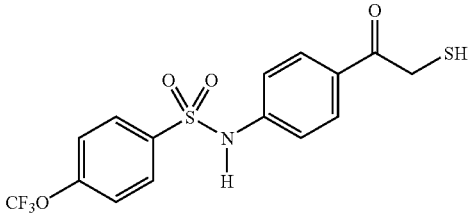

N-[4-(2-Mercapto-acetyl)-phenyl]-4-trifluoromethoxy-benzenesulfonamide (SII-4)

SII-3 (4.35 g, 7.72 mmol) was suspended in water (1.7 l) before 2 M NaOH (7.25 ml) was added. Solid NaOH (1 g) was then added, and the resulting mixture was then heated to reflux overnight, producing a red solution. The solution was then acidified to a pH of 1 and extracted with ethyl acetate. Drying over Na$_2$SO$_4$ and evaporation leaves a red oil. Throughout the work-up, the alpha-mercapto ketone readily oxidizes to the corresponding disulfide, which was purified by preparative HPLC (0.582 g, 0.75 mmol, 10%). $^1$H-NMR: (400 MHz, DMSO-d$_6$) 11.09 (bs, 2H), 7.97 (d, 4H), 7.85 (d, 4H), 7.57 (d, 4H), 7.22 (d, 4H), 4.29 (s, 4H). LC-MS (ES+): 781 [MH]$^+$ m/e.

Step 5

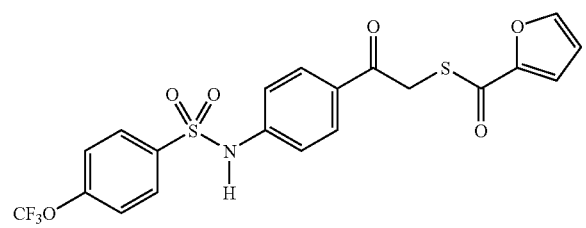

Furan-2-carbothioic acid S-{2-oxo-2-[4-(4-trifluoromethoxy-benzenesulfonylamino)-phenyl]-ethyl}ester To thiol SII-4 (0.5 g, 1.33 mmol) in 5 ml degassed anhydrous DCM (5 ml) was added 2-furoyl chloride (190 mg, 1.46 mmol) followed by DIEA (0.19 g, 1.46 mmol). The reaction was stirred for 4 hours and the solvent was evaporated. The product was first purified by flash chromatography (4:6 EtOAc:hexanes), then recrystallized from EtOAc and finally triturated with DCM to afford 31 mg (0.064 mmol, 5%) product as a white solid. $^1$H-NMR: (400 MHz, CDCl3): 8.00 (d, 2H), 7.94 (d, 2H), 7.64 (d, 1H), 7.35 (d, 2H), 7.29 (d, 1H), 7.22 (d, 2H), 6.60 (t, 1H), 4.50 (s, 2H); LC-MS (ES+): 486 [MH]$^+$ m/e.

Example 5

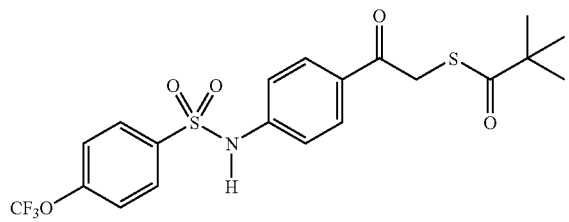

1-(4-Diethylamino-phenyl)-2-mercapto-ethanone was synthesized according to the procedure described in the preparation of Example 4. $^1$H-NMR: (400 MHz, CDCl$_3$): 7.96 (d, 2H), 7.93 (d, 2H), 7.35 (d, 2H), 7.21 (d, 2H), 4.27 (s, 2H); LC-MS (ES+): 476 [MH]$^+$ m/e.

Example 6

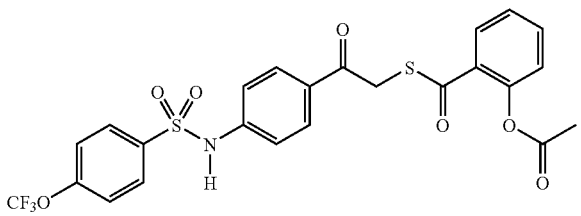

Acetic acid 2-{2-oxo-2-[4-(4-trifluoromethoxy-benzenesulfonylamino)-phenyl]-ethylsulfanylcarbonyl}-phenyl ester was synthesized according to the procedure described in the preparation of Example 4. $^1$H-NMR: (400 MHz, CDCl$_3$): 7.99 (d, 2H), 7.95 (d, 2H), 7.60 (t, 1H), 7.30 (d, 2H), 7.12 (d, 2H), 7.09 (d, 2H), 4.47 (s, 2H), 2.37 (s, 3H); LC-MS (ES+): 555 [MH]$^+$ m/e.

Example 7

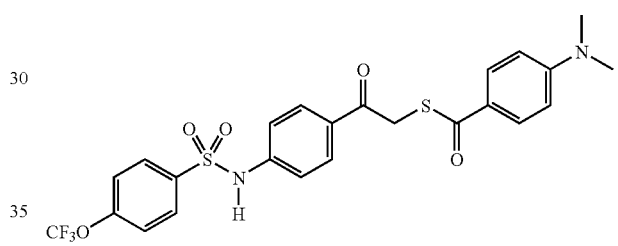

4-Dimethylamino-thiobenzoic acid S-{2-oxo-2-[4-(4-trifluoromethoxy-benzenesulfonylamino)-phenyl]-ethyl ester was synthesized according to the procedure described in the preparation of Example 4. $^1$H-NMR: (400 MHz, DMSO): 11.10 (s, 1H), 8.01 (d, 2H), 7.99 (d, 2H), 7.78 (d, 2H), 7.60 (d, 2H), 7.28 (d, 2H), 6.78 (d, 2H), 4.35 (s, 2H), 3.02 (s, 6H); LC-MS (ES+): 539 [MH]$^+$ m/e.

Example 8

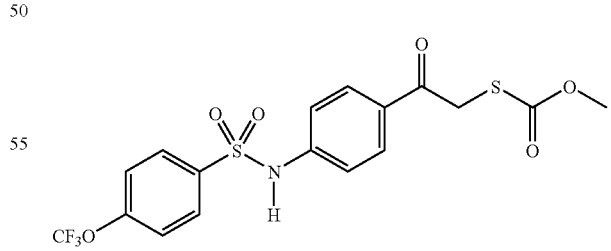

Thiocarbonic acid O-methyl ester S-{2-oxo-2-[4-(4-trifluoromethoxy-benzenesulfonylamino)-phenyl]-ethyl}ester was synthesized according to the procedure described in the preparation of Example 4. $^1$H-NMR: (400 MHz, CDCl$_3$): 7.96 (d, 2H), 7.92 (d, 2H), 7.38 (d, 2H), 7.21 (d, 2H), 4.37 (s, 2H), 3.83 (s, 3H); LC-MS (ES+): 448 [MH]$^+$ m/e.

Example 9

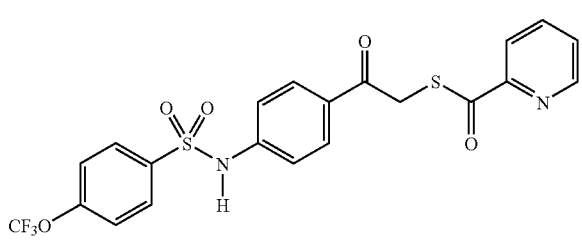

Pyridine-2-carbothioic acid S-{2-oxo-2-[4-(4-trifluoromethoxy-benzenesulfonylamino)-phenyl]-ethyl}ester Picolinic acid (0.25 g, 2.04 mmol) was dissolved in anhydrous, degassed DCM (5 ml), HATU (775 mg, 2.04 mmol) was added followed by DIEA (0.53 g, 4.1 mmol). The mixture was stirred for 20 min and N-[4-(2-Mercapto-acetyl)-phenyl]-4-trifluoromethoxy-benzenesulfonamide SII-4 (0.725 g, 1.85 mmol) was added in 5 ml anhydrous, degassed DCM and the mixture was stirred for 16 hours. The reaction was filtered and the solvent evaporated. The product was purified by flash chromatography (1:1 EtOAc:hexanes) to afford 125 mg (0.25 mmol, 14%) product as a white solid. $^1$H-NMR: (400 MHz, DMSO): 11.12 (s, 1H), 8.89 (d, 1H), 8.03 (t, 1H), 8.01 (d, 2H), 8.00 (d, 2H), 7.90 (d, 1H), 7.78 (t, 1H), 7.60 (d, 2H), 7.14 (d, 2H), 4.60 (s, 2H); LC-MS (ES+): 497 [MH]$^+$ m/e.

Example 10

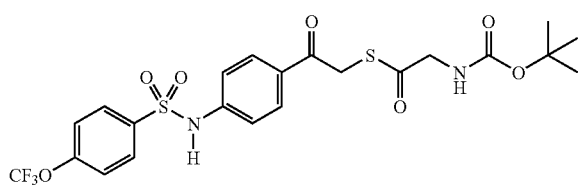

Tert-Butoxycarbonylamino-thioacetic acid S-{2-oxo-2-[4-(4-trifluoromethoxy-benzenesulfonylamino)-phenyl]-ethyl}ester The compound tert-Butoxycarbonylamino-thioacetic acid S-{2-oxo-2-[4-(4-trifluoromethoxy-benzenesulfonylamino)-phenyl]-ethyl }ester was synthesized according to the procedures described in the preparation of Example 9. $^1$H-NMR: (400 MHz, CDCl$_3$): 7.94 (d, 2H), 7.88 (d, 2H), 7.31 (d, 2H), 7.21 (d, 2H), 5.24 (bs, 1b), 4.36 (s, 2H), 4.14 (s, 2H), 1.48 (s, 9H); LC-MS (ES−): 448 [MH]$^-$-Boc m/e (major fragment, no parent ion observed).

Example 11

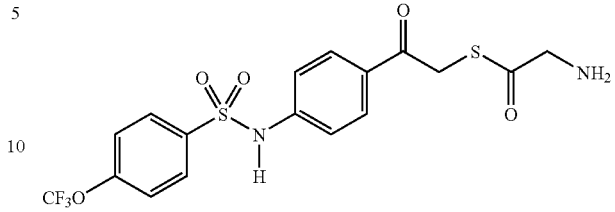

Amino-thioacetic acid S-{2-oxo-2-[4-(4-trifluoromethoxy-benzenesulfonylamino)-phenyl]-ethyl}ester N-Boc thioester from Example 12 (110 mg, 0.2 mmol) was dissolved in anhydrous DCM (1 ml) and TFA (1 ml) was added. The mixture was stirred for 10 minutes and the volatiles removed in vacuo. Recrystallization from EtOAc-hexanes afforded 70 mg product (0.15 mmol, 75%) as an off white solid. $^1$H-NMR: (400 MHz, DMSO): 11.08 (bs, 1H), 8.00 (d, 2H), 7.99 (d, 2H), 7.60 (d, 2H), 7.14 (d, 2H), 4.61 (s, 2H), 4.21 (s, 2H); LC-MS (ES+): 449 [MH]$^+$ m/e.

Example 12

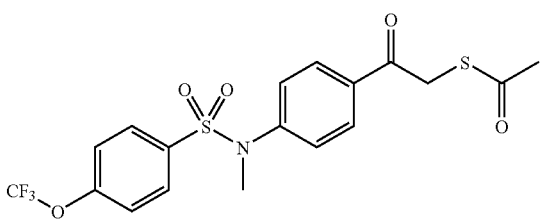

Thioacetic acid S-(2-{4-[methyl-(4-trifluoromethoxy-benzenesulfonyl)-amino]phenyl}-2-oxo-ethyl)ester The compound thioacetic acid S-(2-{4-[methyl-(4-trifluoromethoxy-benzenesulfonyl)-amino]phenyl}-2-oxo-ethyl) ester was synthesized according to the procedures described in the preparation of Example 1. $^1$H NMR: (400 MHz, DMSO-d6) δ 8.00 (d, 2H), 7.63 (d, 2H), 7.60 (d, 2H), 7.38 (d, 2H), 4.50 (s, 2H), 3.10 (s, 3H), 2.40 (s, 3H); LCMS (ES+): 438 [M]$^+$ m/e.

Example 13

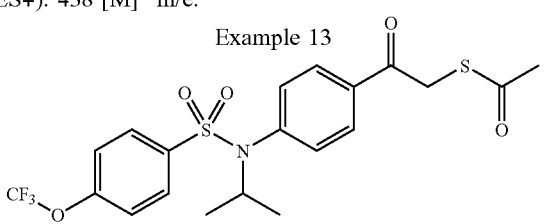

Thioacetic acid S-(2-{4-[isopropyl-(4-trifluoromethoxy-benzenesulfonyl)-amino]-phenyl}-2-oxo-ethyl)ester The compound thioacetic acid S-(2-{4-[isopropyl-(4-trifluoromethoxy-benzenesulfonyl)-amino]-phenyl}-2-oxoethyl) ester was synthesized according to the procedures described in the preparation of Example 1. $^1$H NMR: (400 MHz, DMSO-d6) δ 8.02 (d, 2H), 7.90 (d, 2H), 7.60 (d, 2H), 7.22 (d, 2H), 4.56 (s, 2H), 4.43 (m, 1H), 2.40 (s, 3H), 1.00 (d, 6H); LCMS (ES+): 476 [M]$^+$ m/e.

Example 14

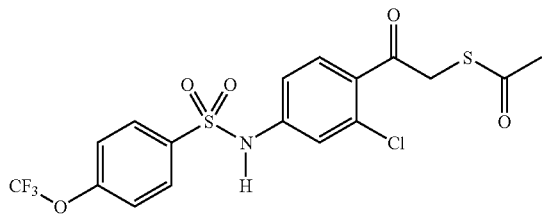

Thioacetic acid S-{2-[2-chloro-4-(4-trifluoromethoxy-benzenesulfonylamino)-phenyl]-2-oxo-ethyl}ester The compound thioacetic acid S-{2-[2-chloro-4-(4-trifluoromethoxy-benzenesulfonylamino)-phenyl]-2-oxo-ethyl}ester was synthesized according to the procedures described in the preparation of Example 1. $^1$H NMR: (400 MHz, DMSO-d6) δ11.10 (s, 1H), 8.00 (d, 2H), 7.99 (d, 1H), 7.60 (s, 1H), 7.10 (d, 1H), 4.35 (s, 2H), 2.36 (s, 3H); LCMS (ES+): 467 [M]$^+$ m/e.

Example 15

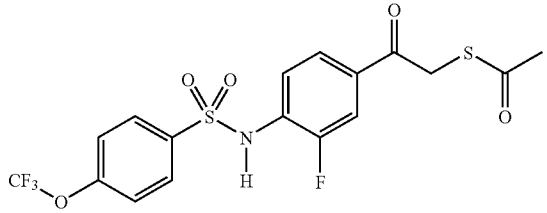

Thioacetic acid S-{2-[3-fluoro-4-(4-trifluoromethoxy-benzenesulfonylamino)-phenyl]-2-oxo-ethyl}ester The compound thioacetic acid S-{2-[3-fluoro-4-(4-trifluoromethoxy-benzenesulfonylamino)-phenyl]-2-oxo-ethyl}ester was synthesized according to the procedures described in the preparation of Example 1. $^1$H NMR: (400 MHz, DMSO-d6) δ 10.94 (s, 1H), 7.98 (d, 2H), 7.81 (d, 2H), 7.60 (d, 2H), 7.49 (t, 1H), 4.42 (s, 2H), 2.39 (s, 3H); LCMS (ES+): 452 [M]$^+$ m/e.

Example 16

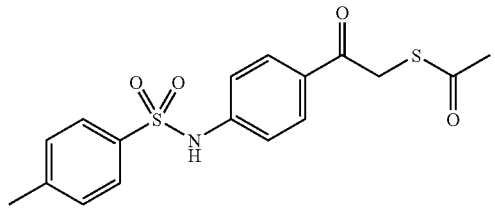

Thioacetic acid S-{12-oxo-2-[4-(toluene-4-sulfonylamino)-phenyl]-ethyl}ester

The compound thioacetic acid S-{2-oxo-2-[4-(toluene-4-sulfonylamino)-phenyl]-ethyl}ester was synthesized according to the procedures described in the preparation of Example 1. $^1$H-NMR (DMSO): 10.95 (s, 1H), 7.90 (d, 2H), 7.74 (d, 2H), 7.40 (d, 2H), 7.22 (d, 2H), 4.42 (s, 2H), 2.47 (s, 3H), 2.37 (s, 3H); LC-MS (ES+): 364 [MH]$^+$ m/e.

Example 17

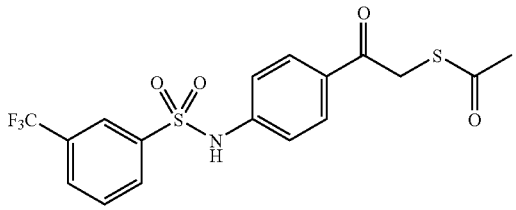

Thioacetic acid S-{2-oxo-2-[4-(3-trifluoromethyl-benzenesulfonylamino)-phenyl]-ethyl}ester The compound thioacetic acid S-{2-oxo-2-[4-(3-trifluoromethyl-benzenesulfonylamino)-phenyl]-ethyl}ester was synthesized according to the procedures described in the preparation of Example 1. $^1$H-NMR (DMSO): 11.12 (s, 1H), 8.10 (m, 3H), 7.88 (m, 3H), 7.26 (d, 2H), 4.43 (s, 2H), 2.37 (s, 3H); LC-MS (ES+): 418 [MH]$^+$ m/e.

Example 18

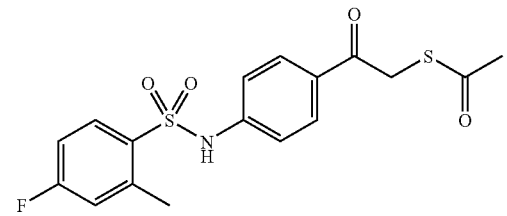

Thioacetic acid S-{2-[4-(4-fluoro-2-methyl-benzenesulfonylamino)-phenyl]-2-oxo-ethyl}ester The compound thioacetic acid S-{2-[4-(4-fluoro-2-methyl-enzenesulfonylamino)-phenyl]-2-oxo-ethyl}ester was synthesized according to the procedures described in the preparation of Example 1. $^1$H-NMR (DMSO): 11.16 (s, 1H), 8.08 (t, 1H), 7.90 (d, 2H), 7.31 (m, 2H), 7.19 (d, 2H), 4.42 (s, 2H), 2.62 (s, 3H), 2.37 (s, 3H); LC-MS (ES+): 382 [MH]$^+$ m/e.

Example 19

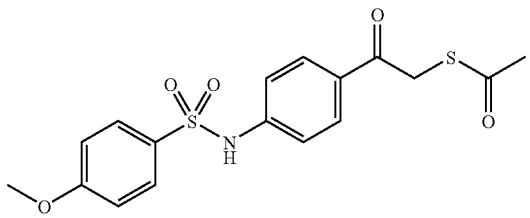

Thioacetic acid S-{2-[4-(4-methoxy-benzenesulfonylamino)-phenyl]-2-oxo-ethyl}ester The compound thioacetic acid S-{2-[4-(4-methoxy-benzenesulfonylamino)-phenyl]-2-oxo-ethyl}ester was synthesized according to the procedures described in the preparation of Example 1. $^1$H-NMR (DMSO): 10.86 (s, 1H), 7.90 (d, 2H), 7.79 (d, 2H), 7.23 (d, 2H), 7.11 (d, 2H), 4.42 (s, 2H), 3.83 (s, 3H), 2.37 (s, 3H); LC-MS (ES+): 380 [MH]$^+$ m/e.

Example 20

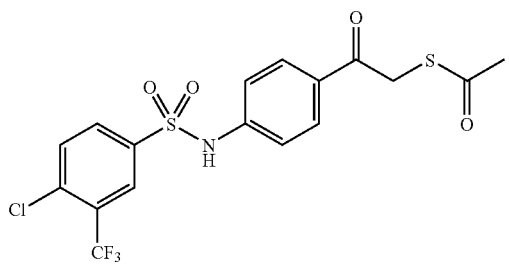

Thioacetic acid S-{2-[4-(4-chloro-3-trifluoromethyl-benzenesulfonylamino)-phenyl]-2-oxo-ethyl}ester The compound thioacetic acid S-{2-[4-(4-chloro-3-trifluoromethyl-benzenesulfonylamino)-phenyl]-2-oxo-ethyl}ester was synthesized according to the procedures described in the preparation of Example 1. $^1$H-NMR (DMSO): 11.16 (s, 1H), 8.20 (s, 1H), 8.12 (t, 1H), 7.98 (m, 3H), 7.27 (d, 2H), 4.44 (s, 2H), 2.37 (s, 3H); LC-MS (ES+): 452 [MH]$^+$ m/e.

Example 21

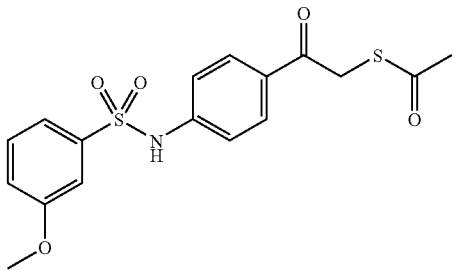

Thioacetic acid S-{2-[4-(3-methoxy-benzenesulfonylamino)-phenyl]-2-oxo-ethyl}ester The compound thioacetic acid S-{2-[4-(3-methoxy-benzenesulfonylamino)-phenyl]-2-oxo-ethyl}ester was synthesized according to the procedures described in the preparation of Example 1. $^1$H-NMR (DMSO): 10.95 (s, 1H), 7.92 (d, 2H), 7.49 (t, 1H), 7.41 (d, 1H), 7.34 (s, 1H), 7.24 (m, 3H), 4.43 (s, 2H), 3.80 (s, 3H), 2.37 (s, 3H); LC-MS (ES+): 380 [MH]$^+$ m/e.

Example 22

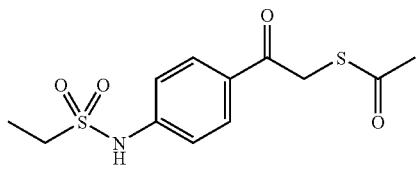

Thioacetic acid S-[2-(4-ethanesulfonylamino-phenyl)-2-oxo-ethyl]ester

The compound thioacetic acid S-[2-(4-ethanesulfonylamino-phenyl)-2-oxo-ethyl]ester was synthesized according to the procedures described in the preparation of Example 1. $^1$H-NMR (DMSO): 10.91 (s, 1H), 8.00 (d, 2H), 7.30 (d, 2H), 4.47 (d, 2H), 3.23 (q, 2H), 2.39 (s, 3H), 1.21 (t, 3H); LC-MS (ES+): 302 [MH]$^+$ m/e.

Example 23

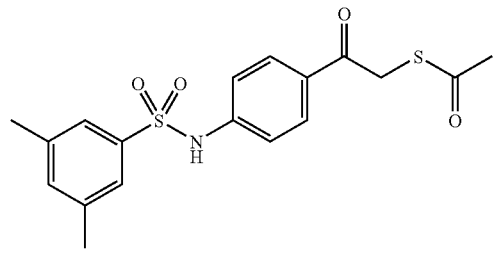

Thioacetic acid 2-[4-(3,5-dimethyl-benzenesulfonylamino)-phenyl]-2-oxo-ethyl ester The compound thioacetic acid 2-[4-(3,5-dimethyl-benzenesulfonylamino)-phenyl]-2-oxo-ethyl ester was synthesized according to the procedures described in the preparation of Example 1. ¹H-NMR (DMSO): 10.91 (s, 1H), 7.91 (d, 2H), 7.49 (s, 2H), 7.24 (d, 3H), 4.43 (s, 2H), 2.27 (s, 3H), 2.33 (s, 6H); LC-MS (ES+): 378 [MH]⁺ m/e.

Example 24

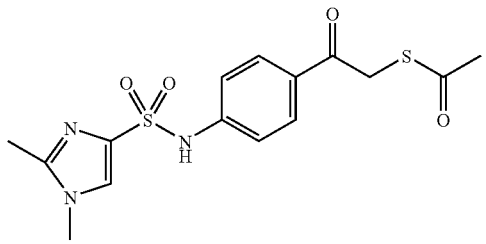

Thioacetic acid S-{2-[4-(1,2-dimethyl-1H-imidazole-4-sulfonylamino)-phenyl]-2-oxo-ethyl}ester The compound thioacetic acid S-{2-[4-(1,2-dimethyl-1H-imidazole-4-sulfonylamino)-phenyl]-2-oxo-ethyl}ester was synthesized according to the procedures described in the preparation of Example 1. ¹H-NMR (DMSO): 10.92 (s, 1H), 7.91 (d, 2H), 7.27 (d, 2H), 4.43 (s, 2H), 3.57 (s, 3H), 2.37 (s, 3H), 2.26, (s, 3H); LC-MS (ES+): 368 [MH]⁺ m/e.

Example 25

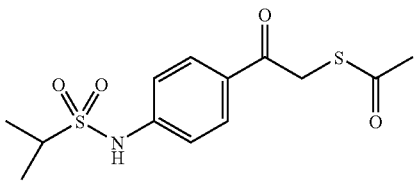

Thioacetic acid S-{2-oxo-2-[4-(propane-2-sulfonylamino)-phenyl]-ethyl}ester

The compound thioacetic acid S-{2-oxo-2-[4-(propane-2-sulfonylamino)-phenyl]-ethyl}ester was synthesized according to the procedures described in the preparation of Example 1. ¹H-NMR (DMSO): 10.38 (s, 1H), 8.00 (d, 2H), 7.36 (d, 2H), 4.47 (s, 2H), 2.39 (s, 3H), 1.25 (s, 7H), LC-MS (ES+): 316 [MH]⁺ m/e.

Example 26

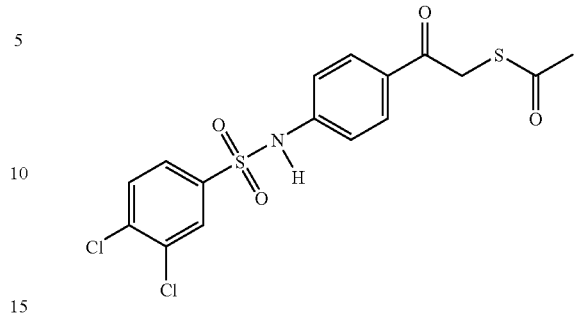

N-[4-(2-Mercapto-acetyl)-phenyl]-3,4-Dichlorobenzene-sulfonamide

The compound N-[4-(2-Mercapto-acetyl)-phenyl]-3,4-Dichlorobenzene-sulfonamide was synthesized according to the procedures described in the preparation of Example 1. ¹H-NMR: (CDCl₃) 7.99(s, 1H), 7.92(d, 2H), 7.68(d, 1H), 7.56(d, 1H), 4.34(s, 2H), 2.42(s, 3H); MS: (418.6)

Example 27

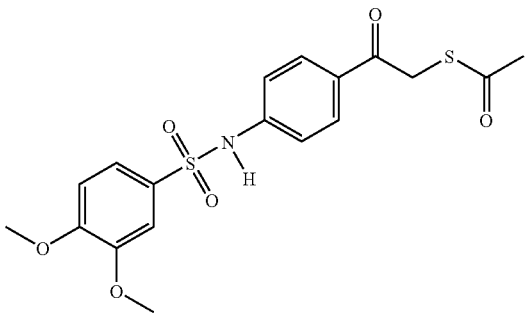

N-[4-(2-Mercapto-acetyl)-phenyl]-3,4-bis-trifluoromethoxy-benzenesulfonamide

The compound N-[4-(2-Mercapto-acetyl)-phenyl]-3,4-bis-trifluoromethoxy-benzenesulfonamide was synthesized according to the procedures described in the preparation of Example 1. ¹H-NMR: (CDCl₃) 7.92(d, 2H), 7.51(d, 1H), 7.31(s, 1H), 7.21(d, 2H), 6.91(d, 1H), 4.38(s, 2H), 2.42(s, 3H); MS: (409.8)

Example 28

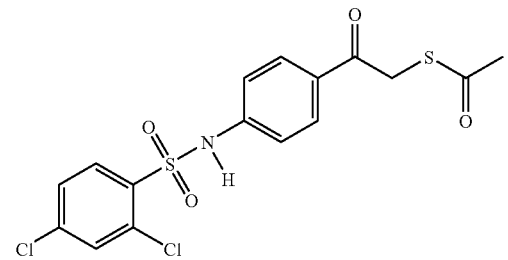

N-[4-(2-Mercapto-acetyl)-phenyl]-2,4-Dichlorobenzene-sulfonamide

The compound N-[4-(2-Mercapto-acetyl)-phenyl]-2,4-Dichlorobenzene-sulfonamide was synthesized according to the procedures described in the preparation of Example 1. $^1$H-NMR: (CDCl$_3$) 8.08(d, 1H), 7.91(d, 2H), 7.58(s, 1H), 7.41(d, 1H), 7.21(d, 2H), 4.32(s, 2H), 2.42(s, 3H); MS: (418.6)

Example 29

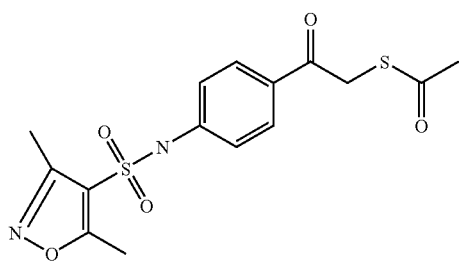

N-[4-(2-Mercapto-acetyl)-phenyl]-2-(3,5-Dimethyl-isoxazole)-sulfonamide

The compound N-[4-(2-Mercapto-acetyl)-phenyl]-2-(3,5-Dimethylisoxazole)-sulfonamide was synthesized according to the procedures described in the preparation of Example 1. $^1$H-NMR: (CDCl$_3$) 8.01(d, 2H), 7.21(d, 2H), 4.39(s, 2H), 2.63(s, 3H), 2.24(s, 3H), 2.20(s, 3H); MS: (368.4)

Example 30

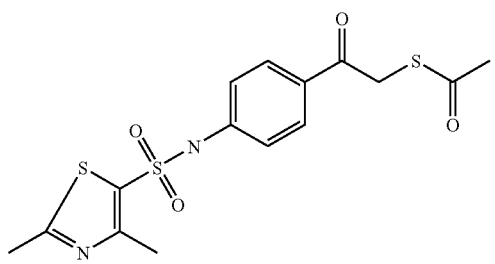

N-[4-(2-Mercapto-acetyl)-phenyl]-5-(2,4-Dimethyl-1,3-Thiazole)-sulfonamide

The compound N-[4-(2-Mercapto-acetyl)-phenyl]-5-(2,4-Dimethyl-1,3-Thiazole)-sulfonamide was synthesized according to the procedures described in the preparation of Example 1. $^1$H-NMR: (CDCl$_3$) 7.98(d, 2H), 7.24(d, 2H), 4.39(s, 2H), 2.68(s, 3H), 2.59(s, 3H), 2.42(s, 3H); MS: (384.4)

Example 31

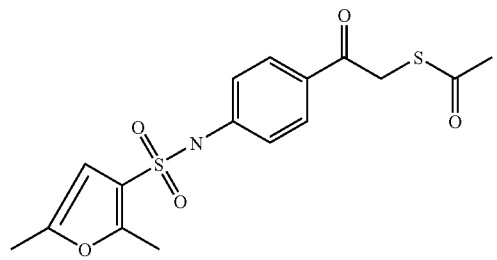

N-[4-(2-Mercapto-acetyl)-phenyl]-3-(2,5-Dimethyl-furan)-sulfonamide

The compound N-[4-(2-Mercapto-acetyl)-phenyl]-3-(2,5-Dimethylfuran)-sulfonamide was synthesized according to the procedures described in the preparation of Example 1. $^1$H-NMR: (CDCl$_3$) 7.98(d, 2H), 7.41(s, 1H), 7.21(d, 2H), 4.39(s, 2H), 2.52(s, 3H), 2.44(s, 3H), 2.21(s, 3H); MS: (386.6).

Example 32

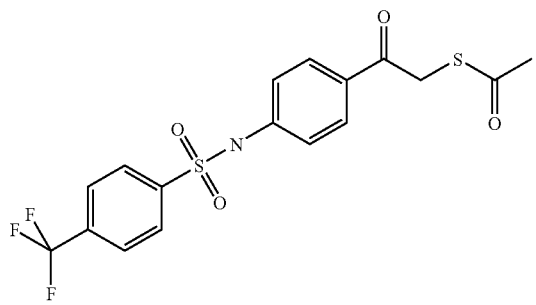

N-[4-(2-Mercapto-acetyl)-phenyl]-4-Trifluoromethylbenzene-sulfonamide

The compound N-[4-(2-Mercapto-acetyl)-phenyl]-4-Trifluoromethylbenzene-sulfonamide was synthesized according to the procedures described in the preparation of Example 1. $^1$H-NMR: (CDCl$_3$) 8.21(d, 2H), 7.98(d, 2H), 7.78(d, 2H), 7.22(d, 2H), 4.39(s, 2H), 2.44(s, 3H); MS: (418.5)

Example 33

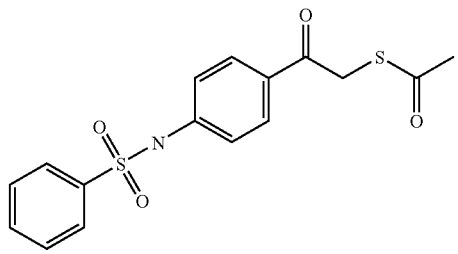

N-[4-(2-Mercapto-acetyl)-phenyl]-4-benzene-sulfonamide

The compound N-[4-(2-Mercapto-acetyl)-phenyl]-4-benzene-sulfonamide was synthesized according to the procedures described in the preparation of Example 1. ¹H-NMR: (CDCl₃) 7.88(d, 3H), 7.59(d, 2H), 7.47(d, 2H), 7.34(d, 2H), 4.29(s, 2H), 2.41(s, 3H); MS: (348.6)

Example 34

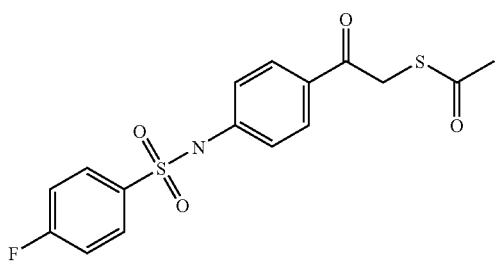

N-[4-(2-Mercapto-acetyl)-phenyl]-4-Fluorobenzene-sulfonamide

The compound N-[4-(2-Mercapto-acetyl)-phenyl]-4-Fluorobenzene-sulfonamide was synthesized according to the procedures described in the preparation of Example 1. ¹H-NMR: (CDCl₃) 7.91(d, 2H), 7.89(d, 2H), 7.22(d, 2H), 7.18(d, 2H), 4.38(s, (2H), 2.42(s, 3H); MS: (367.6)

Example 35

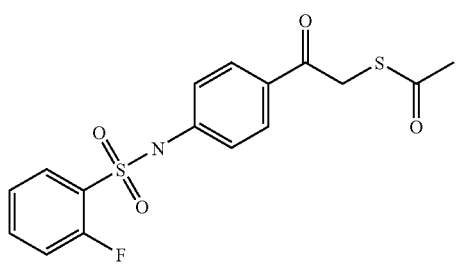

N-[4-(2-Mercapto-acetyl)-phenyl]-2-Fluorobenzene-sulfonamide

The compound N-[4-(2-Mercapto-acetyl)-phenyl]-2-Fluorobenzene-sulfonamide was synthesized according to the procedures described in the preparation of Example 1. ¹H-NMR: (CDCl₃) 7.98(d, 1H), 7.89(d, 2H), 7.61(t, 1H), 7.24(d, 2H), 7.22(d, 2H), 4.37(s, 2H), 2.41(s, 3H); MS: (367.6)

Example 36

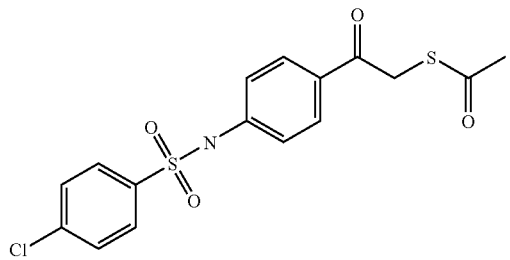

N-[4-(2-Mercapto-acetyl)-phenyl]-4-Chlorobenzene-sulfonamide

The compound N-[4-(2-Mercapto-acetyl)-phenyl]-4-Chlorobenzene-sulfonamide was synthesized according to the procedures described in the preparation of Example 1. ¹H-NMR: (CDCl₃) 7.85(d, 2H), 7.78(d, 2H), 7.60(d, 2H), 7.40(d, 2H), 4.28(s, 2H), 2.41(s, 3H); MS: (384.1)

Example 37

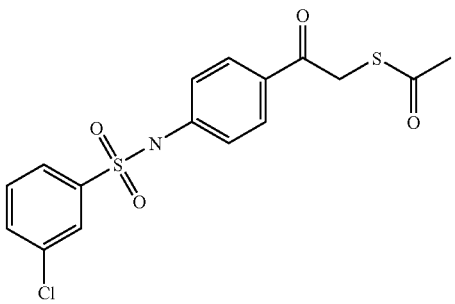

N-[4-(2-Mercapto-acetyl)-phenyl]-3-Chlorobenzene-sulfonamide

The compound N-[4-(2-Mercapto-acetyl)-phenyl]-3-Chlorobenzene-sulfonamide was synthesized according to the procedures described in the preparation of Example 1. ¹H-NMR: (CDCl₃) 7.98(d, 2H), 7.90(s, 1H), 7.78(d, 1H), 7.60(d, 1H), 7.46(t, 1H), 7.21(d, 2H), 4.38(s, 2H), 2.41(s, 3H); MS: (384.1)

Example 38

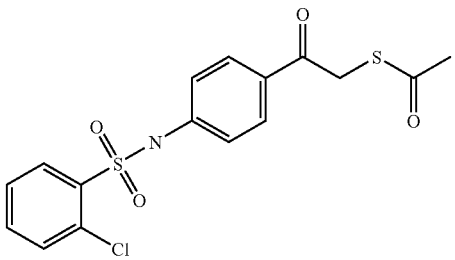

N-[4-(2-Mercapto-acetyl)-phenyl]-2-Chlorobenzene-sulfonamide

The compound N-[4-(2-Mercapto-acetyl)-phenyl]-2-Chlorobenzene-sulfonamide was synthesized according to the procedures described in the preparation of Example 1. $^1$H-NMR: (CDCl$_3$) 8.18(d, 1H), 7.90(d, 2H), 7.58(d, 2H), 7.43(d, 1H), 7.22(d, 2H), 4.38(s, 2H), 2.42(s, 3H); MS: (384.1)

Example 39

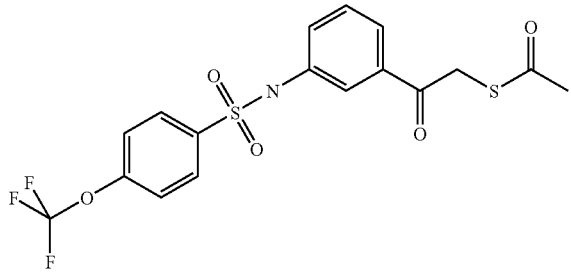

N-[3-(2-Mercapto-acetyl)-phenyl]-4-Trifluoromethoxybenzene-sulfonamide

The compound N-[3-(2-Mercapto-acetyl)-phenyl]-4-Trifluoromethoxybenzene-sulfonamide was synthesized according to the procedures described in the preparation of Example 1. $^1$H-NMR: (CDCl$_3$) 7.90(d, 2H), 7.82(d, 1H), 7.65(s, 1H), 7.44(d, 2H), 7.37(d, 1H), 7.24(d, 1H), 4.39(s, 2H), 2.43(s, 3H); MS: (433.2)

Example 40

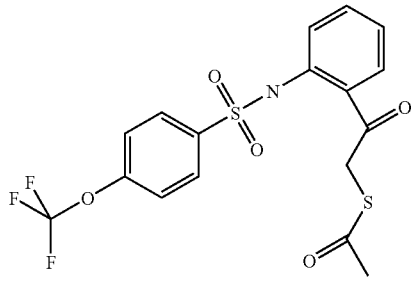

N-[2-(2-Mercapto-acetyl)-phenyl]-4-Trifluoromethoxybenzene-sulfonamide

The compound N-[2-(2-Mercapto-acetyl)-phenyl]-4-Trifluoromethoxybenzene-sulfonamide was synthesized according to the procedures described in the preparation of Example 1. $^1$H-NMR: (CDCl$_3$) 7.91(d, 2H), 7.82(d, 1H), 7.79(t, 1H), 7.58(dd, 1H), 7.24(d, 2H), 7.19(d, 1H), 4.39(s, 2H), 2.42(s, 3H); MS: (433.2)

Example 41

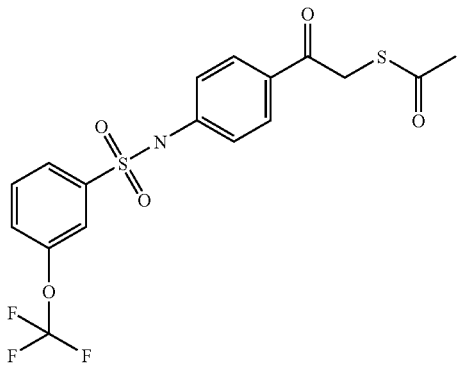

N-[4-(2-Mercpto-acetyl)-phenyl]-3-Trifluoromethoxybenzene-sulfonamide

The compound N-[4-(2-Mercpto-acetyl)-phenyl]-3-Trifluoromethoxybenzene-sulfonamide was synthesized according to the procedures described in the preparation of Example 1. $^1$H-NMR: (CDCl$_3$) 7.96(d, 2H), 7.81(d, 1H), 7.72(s, 1H), 7.59(dd, 1H), 7.43(d, 1H), 7.21(d, 2H), 4.38(s, 2H), 2.41(s, 3H); MS: (433.2)

Example 42

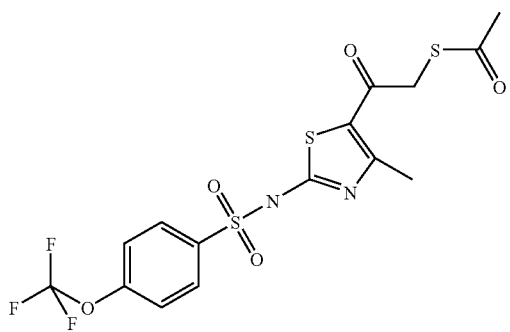

Thioacetic acid-S-{2-[2-(3,4-Di-Trifluoromethoxy-benzenesulfonylamino)-4-methyl-thiazol-5-yl]-2-oxo-ethyl}-ester The compound thioacetic acid-S-{2-[2-(3,4-Di-Trifluoromethoxy-benzenesulfonylamino)-4-methyl-thiazol-5-yl]-2-oxo-ethyl}-ester was synthesized according to the procedures described in the preparation of Example 1. $^1$H-NMR: (CDCl$_3$) 8.01(d, 2H), 7.25(d, 2H), 2.60(s, 3H), 2.41(s, 3H); MS: (454.8)

Example 43

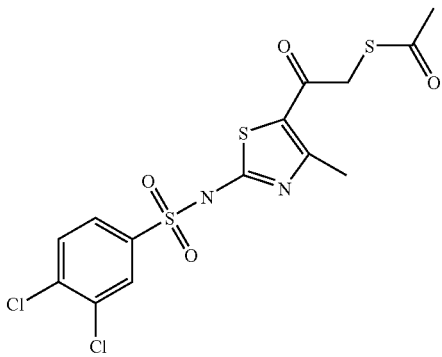

Thioacetic acid-S-{2-[2-(3,4-Dichlorobenzenesulfonylamino)-4-methyl-thiazol-5-yl]-2-oxo-ethyl}-ester The compound thioacetic acid-S-{2-[2-(3,4-Dichlorobenzenesulfonylamino)-4-methyl-thiazol-5-yl]-2-oxo-ethyl}-ester was synthesized according to the procedures described in the preparation of Example 1. $^1$H-NMR: (CDCl$_3$) 8.00(s, 1H), 7.79(d, 1H), 7.49(d, 1H), 4.02(s, 2H), 2.58(s, 3H), 2.41(s, 3H); MS: (439.6)

Example 45

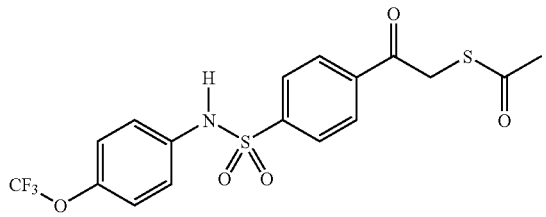

Thioacetic acid S-{2-oxo-2-[4-(4-trifluoromethoxy-phenylsulfamoyl)-phenyl]-ethyl}ester Step 1

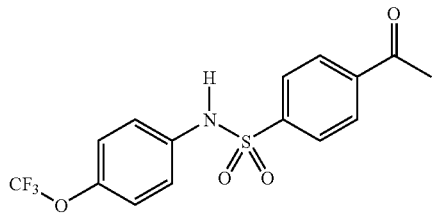

4-Acetyl-N-(4-trifluoromethoxy-phenyl)-benzenesulfonamide

4-Trifluoromethoxy aniline (3.4 g, 19.21 mmol) was dissolved in THF (25 ml) before pyridine (4.44 ml, 54.88 mmol) was added. 4-Acetyl-benzenesulfonyl chloride (4.0 g, 18.29 mmol) was then added as a solid, and the resulting dark solution was stirred for 10 minutes. The volatiles were then removed, and the resulting residue was suspended in THF. Excess Et$_3$N was then added, and the mixture was stirred for several minutes before the solids were filtered. The mother liquor was then evaporated to a solid which was purified by flash chromatography (EtOAc/hexanes) to yield the desired compound as a white solid. (5.5 g (15.31 mmol, 84%).

Step 2

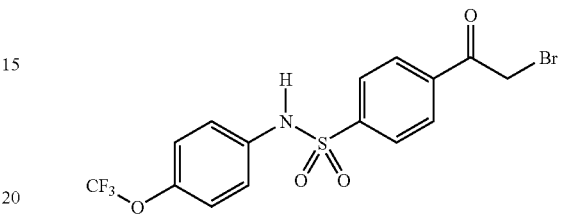

4-(2-Bromo-acetyl)-N-(4-trifluoromethoxy-phenyl)-benzenesulfonamide

The bromoketone intermediate was synthesized according to the procedures described in the preparation of Example 44 Step 2.

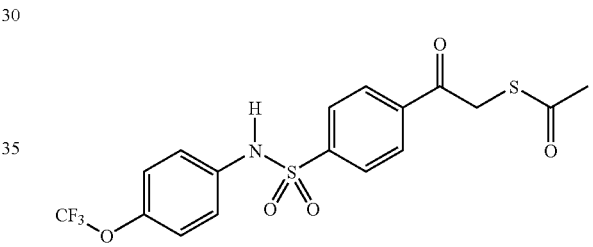

Thioacetic acid S-{2-oxo-2-[4-(4-trifluoromethoxy-phenylsulfamoyl)-phenyl]-ethyl}ester The desired compound was synthesized according to the procedures described in the preparation of Example 44 step 3. $^1$H NMR: (400 MHz, DMSO): 10.74 (s, 1H), 8.08 (d, 2H), 7.92 (d, 2H), 7.23 (d, 2H), 7.20 (d, 2H), 4.57 (s, 2H), 2.38 (s, 3H); LC-MS (ES+): 360 [MH]$^+$ m/e.

Example 46

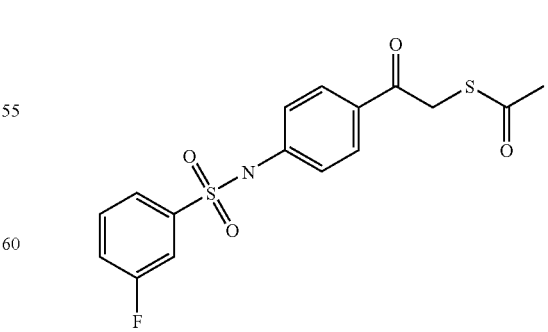

N-[4-(2-Mercapto-acetyl)-phenyl]-3-Fluorobenzenesulfonamide

The compound N-[4-(2-Mercapto-acetyl)-phenyl]-3-Fluorobenzene-sulfonamide was synthesized according to the procedures described in the preparation of Example 1. $^1$H-NMR: (CDCl$_3$) 7.98(d, 2H), 7.68(d, 1H), 7.60(d, 1H), 7.51(dd, 1H), 7.22 (d, 2H), 4.38(s, 2H), 2.41(s, 3H); LC-MS (ES+): 367.6 [MH]$^+$ m/e Example 47

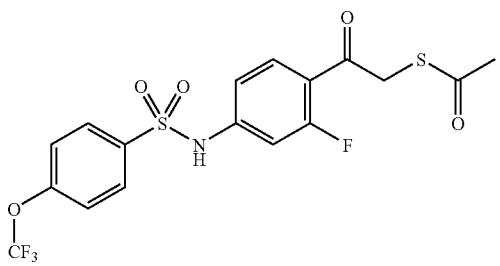

Thioacetic acid S-{2-[2-fluoro-4-(4-trifluoromethoxy-benzenesulfonylamino)-phenyl]-2-oxo-ethyl}ester The compound thioacetic acid S-{2-[2-fluoro-4-(4-trifluoromethyl-benzenesulfonylamino)-phenyl]-2-oxo-ethyl}ester was synthesized according to the procedures described in the preparation of Example 1. $^1$H-NMR (DMSO): 11.37 (bs, 1H), 8.02 (dd, 2H), 7.79 (t, 1H), 7.61 (d, 2H), 7.06 (m, 2H), 4.33 (d, 2H), 2.35 (s, 3H). LC-MS (ES+): 452 [MH]$^+$ m/e.

Example 48

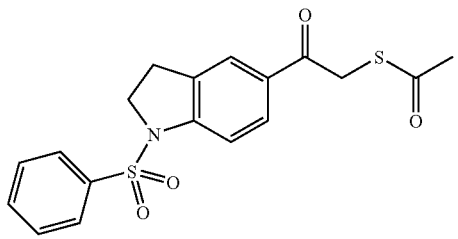

Thioacetic acid S-[2-(1-benzenesulfonyl-2,3-dihydro-1H-indol-5-yl)-2-oxo-ethyl]ester The compound thioacetic acid S-[2-(1-benzenesulfonyl-2,3-dihydro-1H-indol-5-yl)-2-oxo-ethyl]ester was synthesized according to Scheme IV.

Step 1

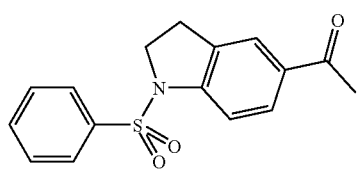

1-(1-Benzenesulfonyl-2,3-dihydro-1H-indol-5-yl)-ethanone 1-(2,3-Dihydro-1H-indol-5-yl)-ethanone (0.200 g, 1.24 mmol) was dissolved in THF (2 ml) before pyridine (0.303 ml, 3.75 mmol) was added, leaving a yellow solution. The benzenesulfonyl chloride (0.220 g, 1.24 mmol) was then added, as a solid, with stirring. The reaction mixture was stirred at 40 C for 5 h. The mixture was cooled and the THF and pyridine were removed in vacuo. The desired sulfonamide (0.310 g, 1.02 mmol, 82%) was recrystallized from ethyl acetate and hexanes. It had LC-MS (ES+): 302 [MH]$^+$ m/e Step 2

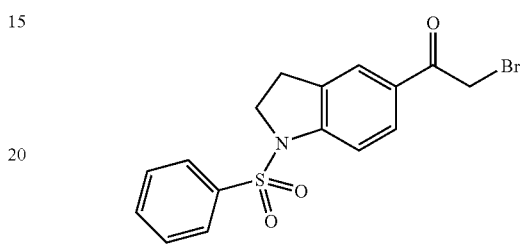

1-(1-Benzenesulfonyl-2,3-dihydro-1H-indol-5-yl)-2-bromo-ethanone

The ketone from step 1 (0.310 g, 1.02 mmol) was dissolved in THF (3 ml), and phenyltrimethylammonium tribromide (PTT) (0.386 g, 1.02 mmol) was added as a solid leaving an orange solution which began to deposit a white solid immediately. Stirring for 1.5 hours leaves a colorless mixture to which water (5 ml) was added. THF was then evaporated and the resulting aqueous mixture was extracted with ethyl acetate. Drying over Na$_2$SO$_4$ and evaporation leaves a white crystalline solid (85% desired mono-brominated material by LC-MS, 5% starting material, 10% dibrominated) suitable for the next step. LC-MS (ES+): 381, 379 m/e.

Step 3

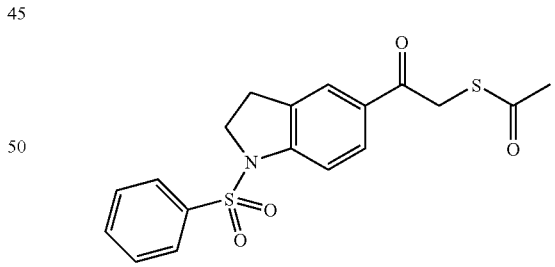

Thioacetic acid S-[2-(1-benzenesulfonyl-2,3-dihydro-1H-indol-5-yl)-2-oxo-ethyl]ester The mono-brominated sulfonamide from step 2 (0.194 g, 0.509 mmol) was dissolved in methanol (2 ml) before potassium thioacetate (0.0639 g, 0.560 mmol) was added as a solid. LC-MS of the resulting yellow solution shows the reaction is complete in minutes. Evaporation of the volatiles leaves a tan residue which was taken up into dichloromethane (4 ml), during which the disulfide of the thioacetic acid was deposited and filtered. The desired thioester could then be recrystallized from dichloromethane/hexanes (0.080 g, 0.214 mmol, 42%). LC-MS (ES+): 376 [MH]+ m/e. ¹H-NMR (DMSO): 7.87 (d, 3H), 7.78 (s, 1H), 7.7 (m, 1H), 7.57 (m, 3H), 4.41 (s, 2H), 3.99 (t, 2H), 3.06 (t, 2H), 2.34 (s, 3H)

Example 49

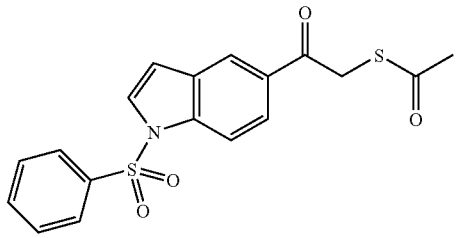

Thioacetic acid S-[2-(1-benzenesulfonyl-1H-indol-5-yl)-2-oxo-ethyl]ester

The compoundthioacetic acid S-[2-(1-benzenesulfonyl-1H-indol-5-yl)-2-oxo-ethyl]ester was synthesized according to the procedures described in the preparation of Example 48. ¹H-NMR (CDCl₃): 8.22 (d, 1H), 8.07 (m, 1H), 7.98 (m, 1H), 7.90 (m, 2H), 7.66 (d, 1H), 7.57 (m, 1H), 7.47 (m, 2H), 6.76 (m, 1H), 4.42 (s, 2H), 2.40 (s, 3H). LC-MS (ES+): 374 [MH]+ m/e Example 50

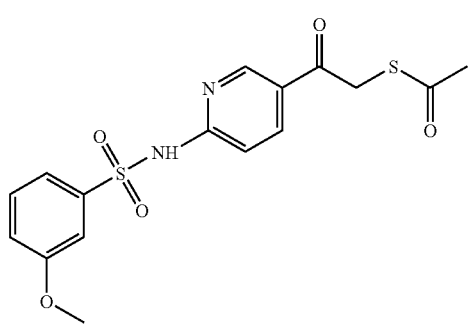

Thioacetic acid S-{2-[6-(3-methoxy-benzenesulfonylamino)-pyridin-3-yl]-2-oxo-ethyl}ester The compound thioacetic acid S-{2-[6-(3-methoxy-benzenesulfonylamino)-pyridin-3-yl]-2-oxo-ethyl}ester was synthesized according to the procedures described in the preparation of Example 1. ¹H-NMR: (CDCl₃) 8.91(s, 1H), 8.21(d, 1H), 7.51(d, 1H), 7.44(d, 1H), 7.42(d, 1H), 7.38(s, 1H), 7.09(d, 1H), 4.21(s, 2H), 3.82(s, 3H), 2.41(s, 3H) ppm. MS: (380.05)

Example 51

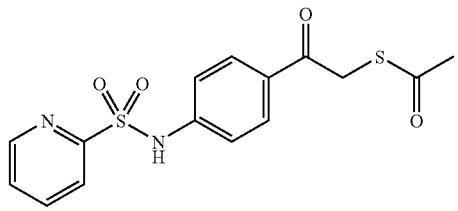

Thioacetic acid S-{2-oxo-2-[4-(pyridine-2-sulfonylamino)-phenyl]-ethyl}ester

The compound Thioacetic acid S-{2-oxo-2-[4-(pyridine-2-sulfonylamino)-phenyl]-ethyl}ester was synthesized according to the procedures described in the preparation of Example 1. ¹H-NMR (DMSO): 11.19 (bs, 1H), 8.71 (d, 1H), 8.10 (m, 2H), 7.89 (d, 2H), 7.67 (m, 1H), 7.28 (d, 2H), 4.41 (s, 2H), 2.36 (s, 3H). LC-MS (ES+): 351 [MH]+ m/e.

Example 52

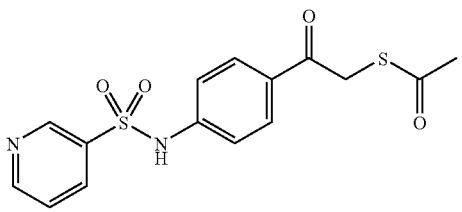

Thioacetic acid S-{2-oxo-2-[4-(pyridine-3-sulfonylamino)-phenyl]-ethyl}ester

The compound Thioacetic acid S-{2-oxo-2-[4-(pyridine-3-sulfonylamino)-phenyl]-ethyl}ester was synthesized according to the procedures described in the preparation of Example 1 ¹H-NMR (DMSO): 11.16 (bs, 1H), 8.99 (d, 1H), 8.81 (dd, 1H), 8.23 (m, 1H), 7.92 (d, 2H), 7.64 (dd, 1H), 7.26 (d, 2H), 4.42 (s, 2H), 2.36 (s, 3H). LC-MS (ES+): 351 [MH]+ m/e.

Example 53

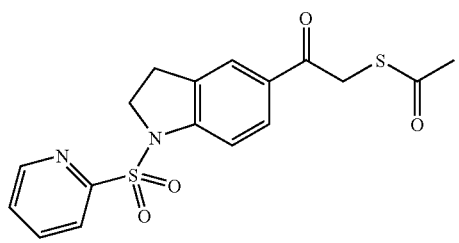

Thioacetic acid S-{2-oxo-2-[1-(pyridine-2-sulfonyl)-2,3-dihydro-1H-indol-5-yl]-ethyl}ester The compound thioacetic acid S-{2-oxo-2-[1-(pyridine-2-sulfonyl)-2,3-dihydro-1H-indol-5-yl]-ethyl} was synthesized according to the procedures described in the preparation of Example 48. ¹H-NMR (DMSO): 8.67 (m, 1H), 8.11 (m, 2H), 7.82 (m, 2H), 7.50 (m, 1H), 7.43 (d, 1H) (s, 2H), 4.23 (t, 2H), 3.15 (t, 2H), 2.36 (s, 3H). LC-MS (ES+): 377 [MH]⁺ m/e.

Example 54

Thiophosphoric acid S-{2-oxo-2-[4-(4-trifluoromethoxy-benzenesulfonylamino)-phenyl]-ethyl}ester The compound from Example 1, Step 2 (0.200 g, 0.461 mmol) was dissolved in methyl alcohol (3 mL). Na₃SPO₃ (0.091 g, 0.508 mmol) was added as a solid, forming a heterogeneous suspension. The suspension was stirred at room temperature. After 1.5 hours a white precipitate was present. This precipitate was filtered and found to be the undesired disulfide of the starting sulfonamide. The methyl alcohol was then removed and dichloromethane was added to the crude reaction mixture. A white solid precipitated out of the dichloromethane solution which was collected by filtration. The solid was further purified by mass triggered HPLC to give the desired compound (0.050 g, 0.106 mmol, 23%). ¹H-NMR (DMSO): 11.06 (s, 1H), 7.98 (m, 2H), 7.88 (m, 2H), 7.59 (d, 2H), 7.23 (m, 2H), 4.16 (d, 2H). LC-MS (ES+): 471 [MH]⁺ m/e.

The following compounds can be made using the methods as described above and when made should have similar activity as those made above.

wherein $G_1$ is selected from the following:

[isoxazole, thiazole, furan, imidazole, oxadiazole, oxazole, pyrazole, thiophene, pyridine, pyrazine, pyrimidine, oxadiazole, triazine, and triazine];

$G_2$ is selected from the following:

[amide, reverse amide, sulfonamide with $R_3$, and sulfonamide with $R_4$];

$G_3$ is selected from the following:

[isoxazole, thiazole, furan, imidazole, oxadiazole, oxazole, pyrazole, thiophene, pyridine, pyrazine, pyrimidine, oxadiazole, triazine, and triazine];

and $G_4$ is selected from the following:

[acetyl, pivaloyl, pentanoyl, methyl ester, and benzoyl];

-continued
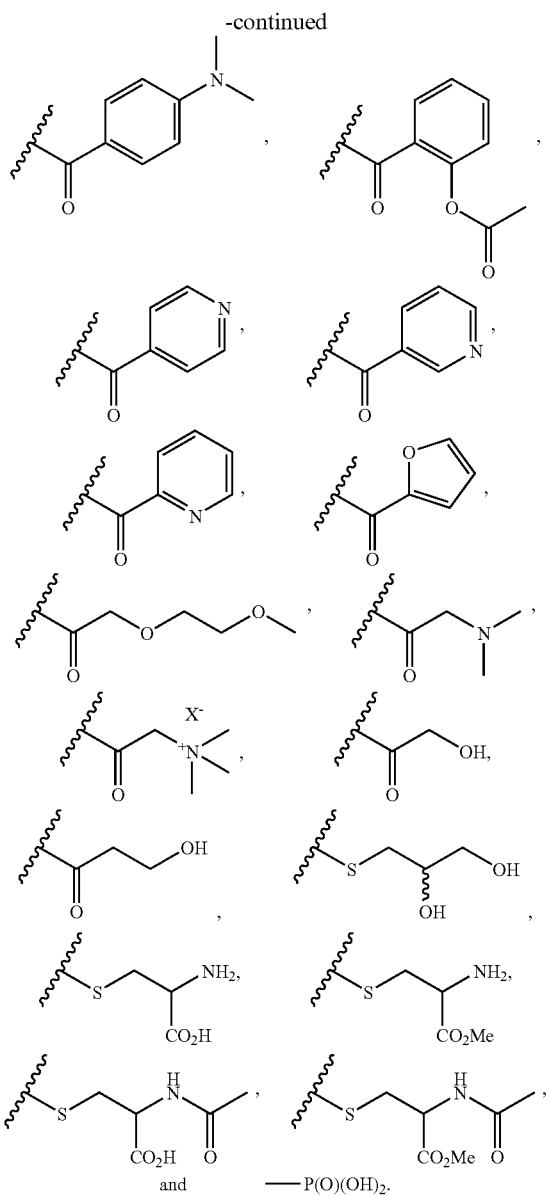
Additionally, the following compounds can be made using the methods as described above.
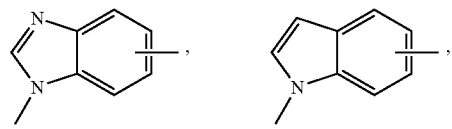
wherein $G_1$ is selected from the following:
-continued
$G_2$ is selected from the following:
$G_3$ is selected from the following:
and $G_4$ is selected from the following:

-continued

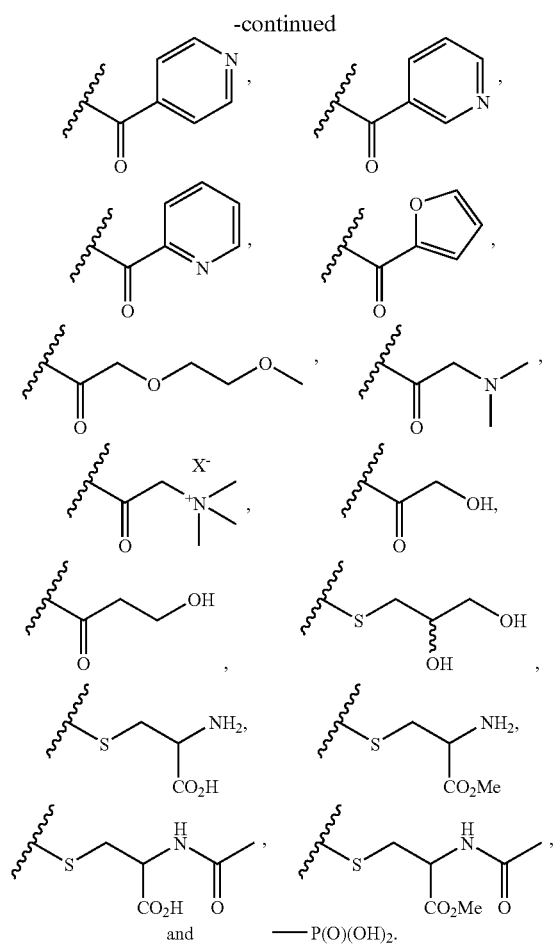

and —P(O)(OH)$_2$.

The prophetic examples disclosed herein may optionally be substituted as described above.

The activity of the above mentioned compounds as HDAC inhibitors has generally been shown by the following assays. The other compounds listed above, which may not yet been made or tested, are predicted to generally have activity in these assays as well.

Inhibition Assays:

In vitro HDAC-Inhibition Assay:

This assay measures a compound's ability to inhibit acetyl-lysine deacetylation in vitro and was used as both a primary screening method as well as for IC$_{50}$ determinations of confirmed inhibitors. The assay is performed in vitro using an HDAC enzyme source (e.g. partially purified nuclear extract or immunopurified HDAC complexes) and a proprietary fluorescent substrate/developer system (HDAC Quantizyme Fluor de Lys Fluorescent Activity Assay, BIO-MOL). The assay is run in 1,536-well Greiner white-bottom plates using the following volumes and order of addition:

Step 1: Enzyme (2.5 ul) source added to plate (from refrigerated container)

Step 2: Compounds (50 nl) added with pin transfer device

Step 3: Fluor de Lys (2.5 ul) substrate added, incubate at RT, 30 minutes

Step 4: Developer (5 ul) solution is added (containing TSA), to stop reaction

Step 5: Plate Reader—data collection

The deacetylated fluorophore is excited with 360 nm light and the emitted light (460 nm) is detected on an automated fluorometric plate reader (Aquest, Molecular Devices).

Cellular Histone Hyperacetylation Assays:

These two secondary assays evaluates a compound's ability to inhibit HDAC in cells by measuring cellular histone acetylation levels. The cytoblot facilitates quantitative EC$_{50}$ information for cellular HDAC inhibition. Transformed cell lines (e.g. HeLa, A549, MCF-7) are cultured under standard media and culture conditions prior to plating.

For Cytoblot:

Cells (approx. 2,500/well) are allowed to adhere 10-24 hours to wells of a 384-well Greiner PS assay plate in media containing 1-5% serum. Cells are treated with appropriate compound and specific concentrations for 0 to 24 hours. Cells are washed once with PBS (60 ul) and then fixed (95% ethanol, 5% acetic acid or 2% PFA) for 1 minute at RT (30 ul). Cells are blocked with 1% BSA for 1 hour and washed and stained with antibody (e.g. anti-Acetylated Histone H3, Upstate Biotechnology), followed by washing and incubation with an appropriate secondary antibody conjugated to HRP or fluorophore. For luminescence assays, signal is generated using Luminol substrate (Santa Cruz Biotechnology) and detected using an Aquest plate reader (Molecular Devices).

For Immunoblot:

Cells (4×10$^5$/well) are plated into Corning 6-well dish and allowed to adhere overnight. Cells are treated with compound at appropriate concentration for 12-18 hours at 37 degrees. Cells are washed with PBS on ice. Cells are dislodged with rubber policeman and lysed in buffer containing 25 mM Tris, pH 7.6; 150 mM NaCl, 25 mM MgCl$_2$, 1% Tween-20, and nuclei collected by centriguation (7500 g). Nuclei are washed once in 25 mM Tris, pH 7.6; 10 mM EDTA, collected by centrifugation (7500 g). Supernatant is removed and histones are extracted using 0.4 M HCl. Samples are centrifuged at 14000 g and supernatants are precipitated in 1 ml cold acetone. The histone pellet is dissolved in water and histones are separated and analyzed by SDS-PAGE Coomassie and immunobloting (anti-acetylated histone antibodies, Upstate Biotechnology) using standard techniques.

Differential Cytotoxicity Assay:

HDAC inhibitors display differential cytotoxicity toward certain transformed cell lines. Cells are cultured according to standard ATCC recommended conditions that are appropriate to each cell type. Compounds were tested for their ability to kill different cell types (normal and transformed) using the ATPlite luminescence ATP detection assay system (Perkin Elmer). Assays are run in either 384-well or 1536-well Greiner PS plates. Cells (30 ul or 5 ul, respectively) are dispensed using either multichannel pipette for 384-well plates, or proprietary Kalypsys bulk liquid dispenser for 1536-well plates. Compounds added using proprietary pin-transfer device (500 nL or 5 nL) and incubated 5 to 30 hours prior to analysis. Luminescence is measured using Aquest plate reader (Molecular Devices).

The activity of some of the compounds of the invention are shown in Table 1, below. Synthesis of each compound is described in the Example listed in the left column.

TABLE 1
| Example No. | COMPOUND | In vitro IC$_{50}$ (μM) | Cellular IC$_{50}$ (μM) |
|---|---|---|---|
| 02 | 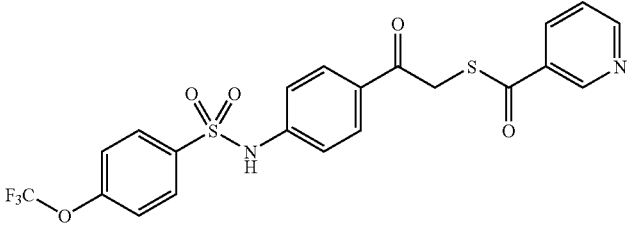 | <1 | <10 |
| 04 | 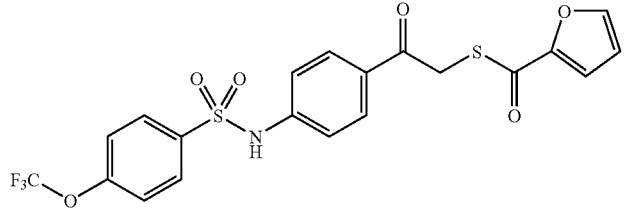 | <1 | |
| 06 | 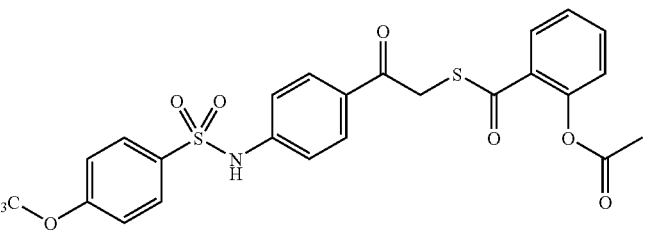 | <1 | <1 |
| 07 | 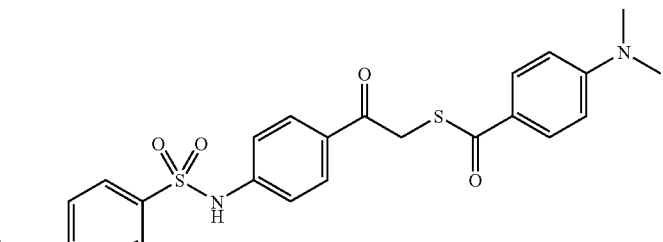 | <1 | <10 |
| 08 | 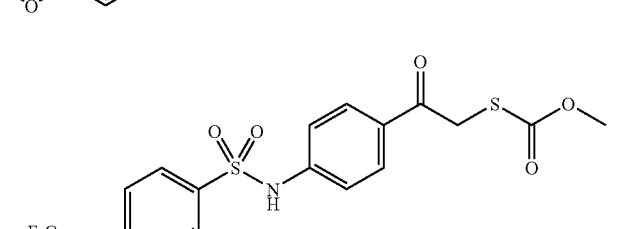 | <10 | <1 |
| 09 | 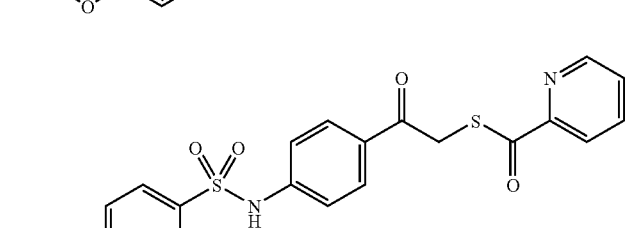 | <1 | <1 |

TABLE 1-continued

| Example No. | COMPOUND | In vitro IC$_{50}$ (μM) | Cellular IC$_{50}$ (μM) |
|---|---|---|---|
| 10 | | <1 | |
| 11 | | <1 | |
| 12 | | <1 | <10 |
| 13 | | <10 | |
| 14 | | <1 | <50 |
| 15 | | <1 | |

TABLE 1-continued
| Example No. | COMPOUND | In vitro IC$_{50}$ (μM) | Cellular IC$_{50}$ (μM) |
|---|---|---|---|
| 16 | 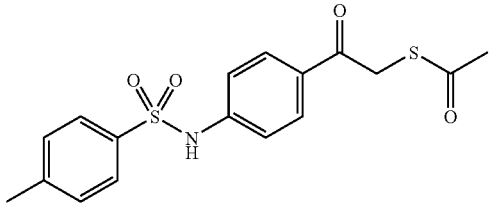 | <1 | <1 |
| 17 | 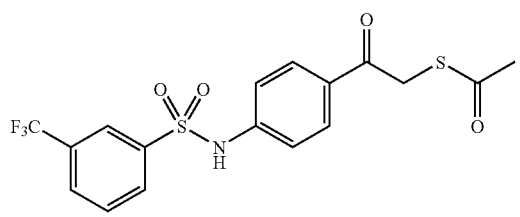 | <1 | <10 |
| 18 | 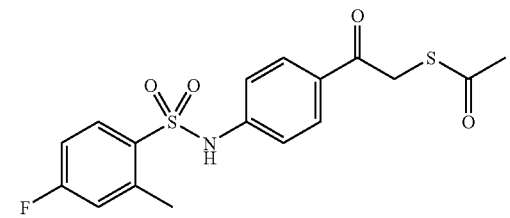 | <1 | <1 |
| 20 | 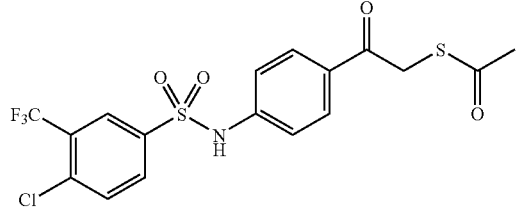 | <1 | <1 |
| 21 | 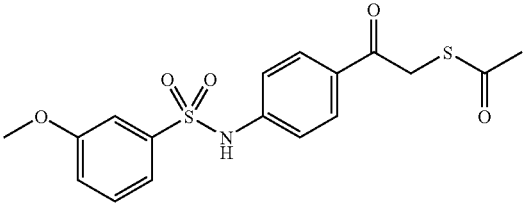 | <1 | <1 |
| 22 | 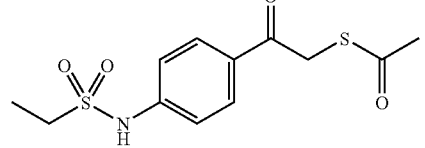 | <1 | <10 |
| 23 | 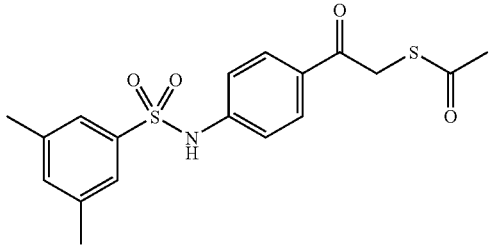 | <1 | <10 |

TABLE 1-continued

| Example No. | COMPOUND | In vitro IC$_{50}$ (μM) | Cellular IC$_{50}$ (μM) |
| --- | --- | --- | --- |
| 24 | | <1 | <10 |
| 25 | | <1 | |
| 27 | | <1 | <1 |
| 28 | | <1 | <1 |
| 29 | | <1 | <10 |
| 30 | | <1 | <1 |

TABLE 1-continued

| Example No. | COMPOUND | In vitro IC$_{50}$ (μM) | Cellular IC$_{50}$ (μM) |
|---|---|---|---|
| 31 | | <1 | <10 |
| 33 | | <1 | <10 |
| 34 | | <1 | <1 |
| 35 | | <1 | <1 |
| 36 | | <1 | <1 |
| 37 | | <1 | <1 |

TABLE 1-continued

| Example No. | COMPOUND | In vitro IC$_{50}$ (μM) | Cellular IC$_{50}$ (μM) |
|---|---|---|---|
| 38 | | <1 | <1 |
| 39 | | <1 | <1 |
| 40 | | <10 | >50 |
| 41 | | <1 | <1 |
| 42 | | <50 | |
| 43 | | <50 | |
| 45 | | <1 | <10 |

TABLE 1-continued

| Example No. | COMPOUND | In vitro IC$_{50}$ (μM) | Cellular IC$_{50}$ (μM) |
| --- | --- | --- | --- |
| 46 | 3-fluorophenyl sulfonamide linked to 4-(2-(acetylthio)acetyl)phenyl | <1 | <1 |
| 47 | 4-(trifluoromethoxy)phenyl sulfonamide linked to 3-fluoro-4-(2-(acetylthio)acetyl)phenyl | <1 | <1 |
| 48 | 1-(phenylsulfonyl)indoline-5-yl 2-(acetylthio)ethan-1-one | <1 | <10 |
| 49 | 1-(phenylsulfonyl)indol-5-yl 2-(acetylthio)ethan-1-one | <1 | <1 |
| 50 | 3-methoxyphenyl sulfonamide linked to 5-(2-(acetylthio)acetyl)pyridin-2-yl | <1 | <1 |
| 51 | pyridin-2-yl sulfonamide linked to 4-(2-(acetylthio)acetyl)phenyl | <1 | <1 |

TABLE 1-continued

| Example No. | COMPOUND | In vitro IC$_{50}$ (μM) | Cellular IC$_{50}$ (μM) |
|---|---|---|---|
| 52 | | <1 | <10 |
| 53 | | <1 | <1 |
| 54 | | | |

A blank cell indicates that the value was not determined.

All references cited above are incorporated herein by reference in their entirety.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having structural formula (I),

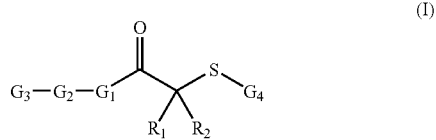

(I)

or a pharmaceutically acceptable salt, amide, ester, or prodrug thereof, wherein:

$G_1$ is optionally substituted phenyl;

$G_2$ is selected from the group consisting of an N-sulfonamide having structure (II), an S-sulfonamide having structure (III), an amide of the form —NR$_3$C(O)—, and an amide of the form —C(O)NR$_3$—:

(II)

(III)

$G_3$ is selected from the group consisting of optionally substituted phenyl and optionally substituted alkyl;

$R_1$ and $R_2$ are each independently selected from the group consisting of hydrogen, lower alkyl, halogen and perhaloalkyl, or $R_1$ and $R_2$ taken together form optionally substituted cycloalkyl;

$R_3$ and $R_4$ are each independently selected from the group consisting of hydrogen, optionally substituted lower alkyl, optionally substituted aryl, and optionally substituted alkaryl and a structural element known to confer aqueous solubility;

$G_4$ is selected from the group consisting of optionally substituted acyl, optionally substituted alkyl thiol, and —P(O)(OR$_5$)$_2$ or —P(O)(OH)$_2$; and each $R_5$ is independently selected from the group consisting of hydrogen, alkyl, aryl, and arylalkyl.

2. The compounds of claim 1 having a structure selected from the group consisting of formula (IV) and formula (V):

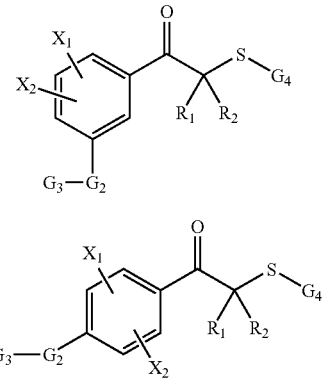

(IV)

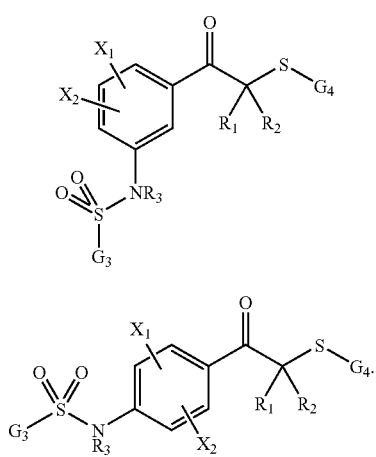

(V)

wherein $X_1$ and $X_2$ are each independently selected from the group consisting of hydrogen, halogen, hydroxyl, optionally substituted lower alkyl, and optionally substituted lower alkoxy.

3. The compound of claim 2, having a structure selected from the group consisting of formula (VI) and formula (VII)

(VI)

(VII)

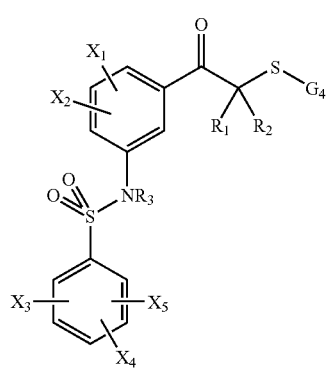

4. The compound of claim 3, having a structure selected from the group consisting of formula (VIII) and formula (IX)

(VIII)

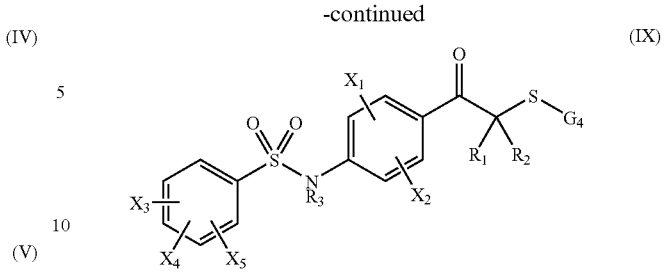

(IX)

wherein $X_3$, $X_4$ and $X_5$ are each independently selected from the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsuiphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, and aminothiocarbonylaminoalkyl.

5. The compound of claim 4 wherein $G_4$ is an optionally substituted acyl having structural formula —C(O)$R_E$, wherein $R_E$ is selected from the group consisting of any pharmaceutically acceptable acid, —P(O)(OH)$_2$, and —P(O)(OR$_5$)$_2$; $R_1$ and $R_2$ are each independently selected from the group consisting of hydrogen and lower alkyl, or $R_1$ and $R_2$ it taken together form optionally substituted cycloalkyl; and $X_1$ and $X_2$ are each independently selected from the group consisting of hydrogen, halogen, hydroxyl, lower alkyl, lower perhaloalkyl, lower alkoxy and lower perhaloalkoxy.

6. The compound of claim 5 wherein $R_3$ is selected from the group consisting of hydrogen, optionally substituted lower alkyl, and a structural element known to confer aqueous solubility.

7. The compound of claim 6 wherein the compound has a structure selected from the group consisting of:

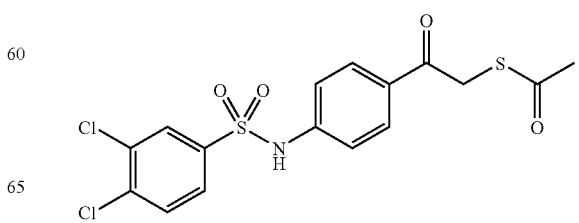

-continued
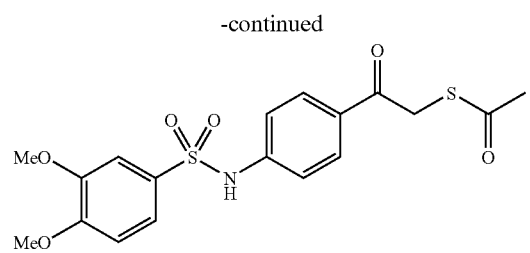
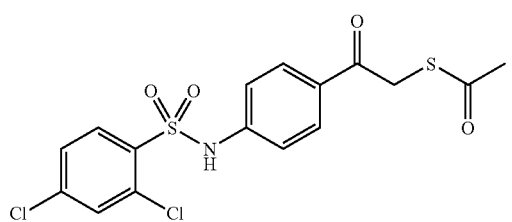
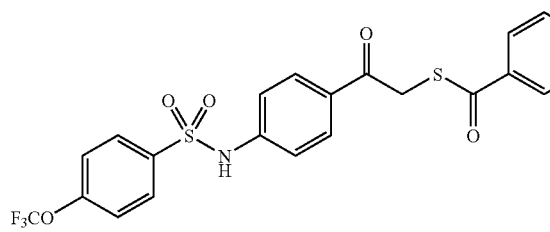
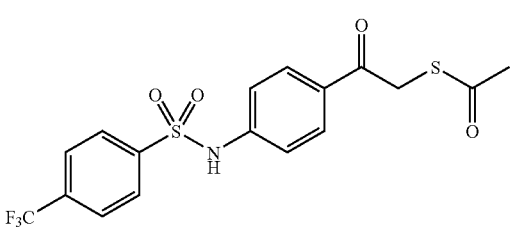
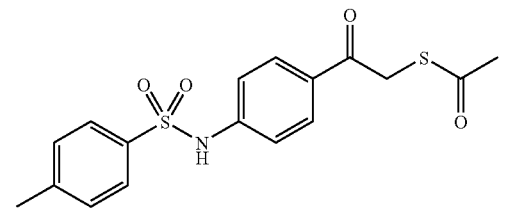
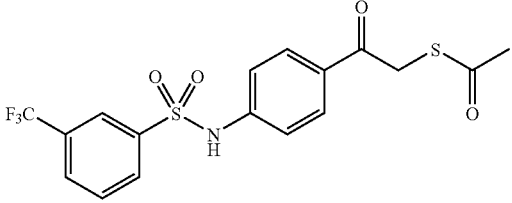
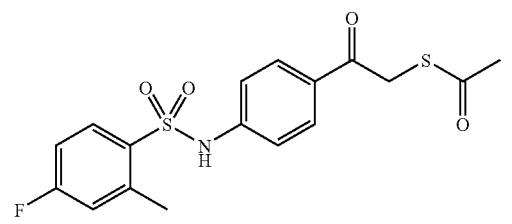
-continued
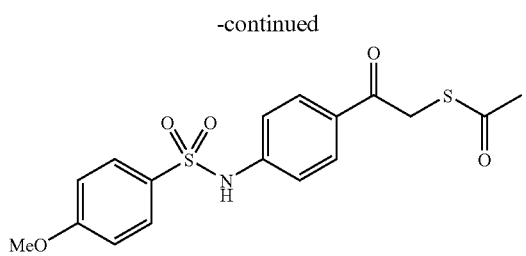
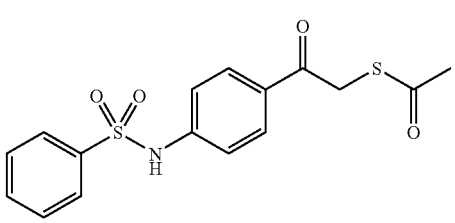
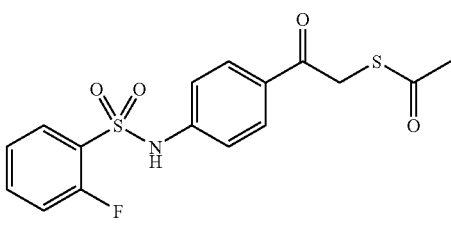
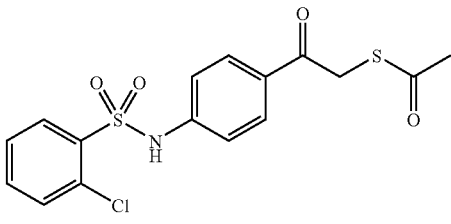
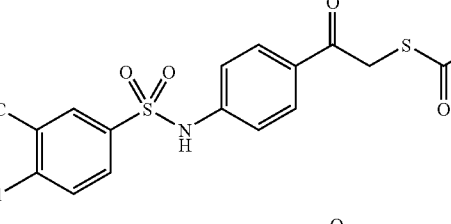
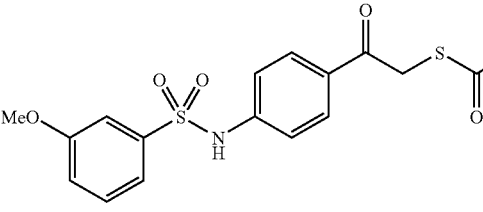
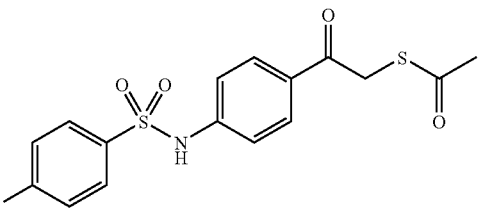

-continued
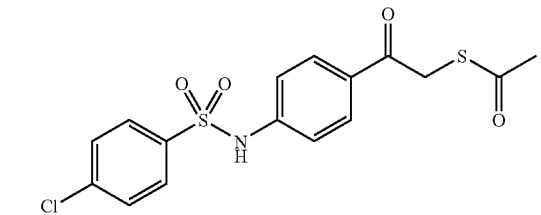
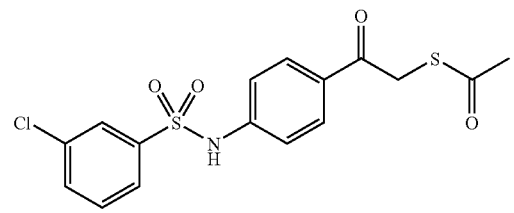
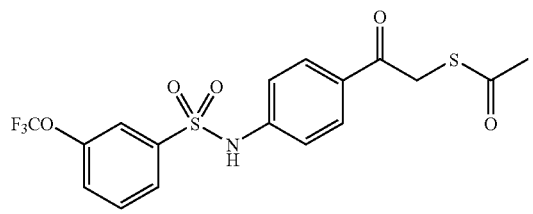
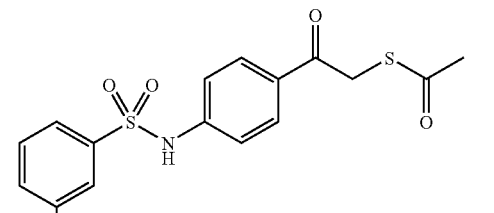
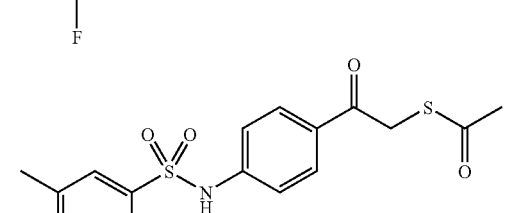
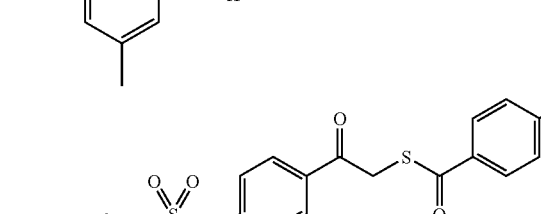
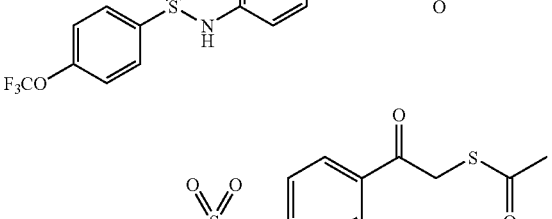
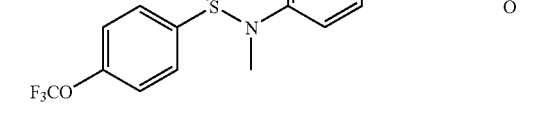
-continued
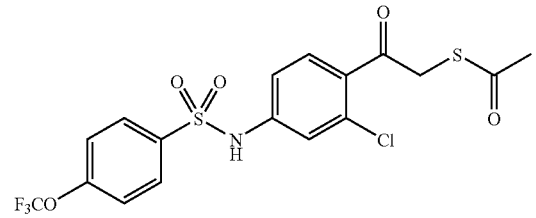
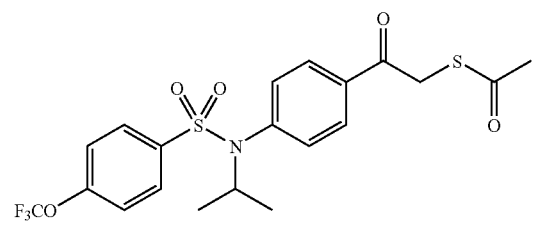
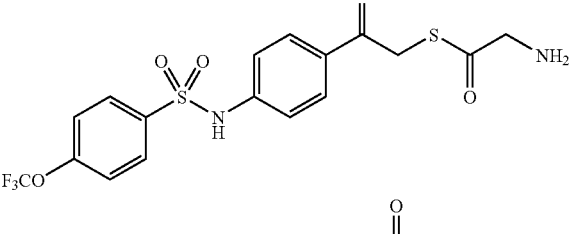
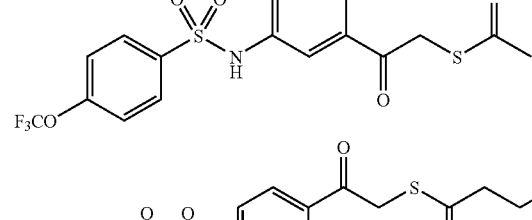
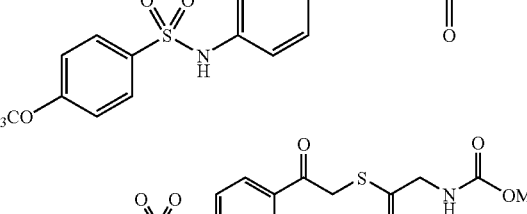
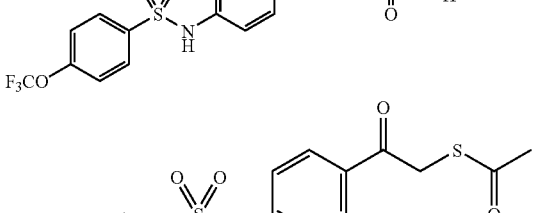
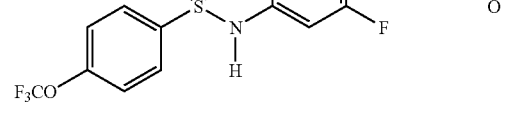

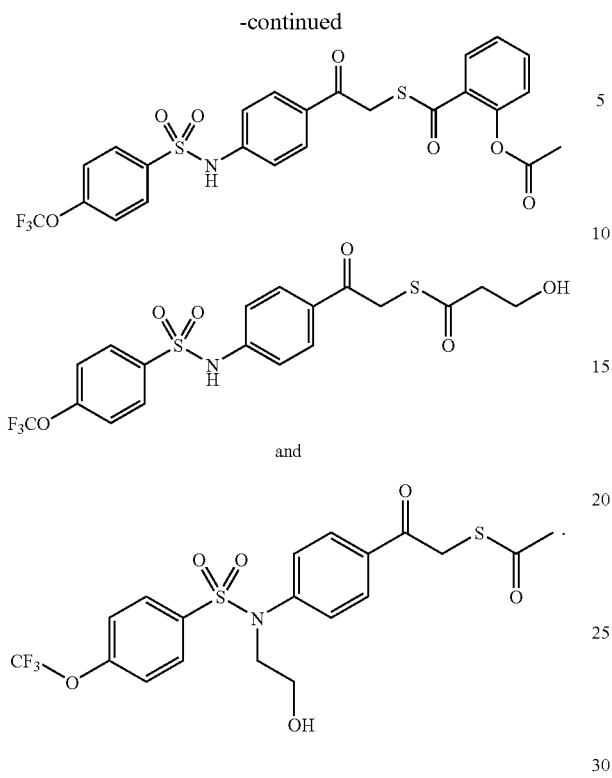

8. The compound of claim 3 wherein $G_3$ comprises an optionally substituted alkyl.

9. The compound of claim 8 wherein $G_4$ is an optionally substituted acyl having structural formula —C(O)$R_E$, wherein $R_E$ is selected from the group consisting of any pharmaceutically acceptable acid, —P(O)(OH)$_2$, and —P(O)(OR$_5$)$_2$; $R_1$ and $R_2$ are each independently selected from the group consisting of hydrogen and lower alkyl, or $R_1$ and $R_2$ taken together form optionally substituted cycloalkyl; and $X_1$ and $X_2$ are each independently selected from the group consisting of hydrogen, halogen, hydroxyl, lower alkyl, lower perhaloalkyl, lower alkoxy and lower perhaloalkoxy.

10. The compound of claim 1 wherein $R_3$ is selected from the group consisting of hydrogen, optionally substituted lower alkyl, and a structural element known to confer aqueous solubility.

11. The compound of claim 10 wherein the compound has a structure selected from the group consisting of:

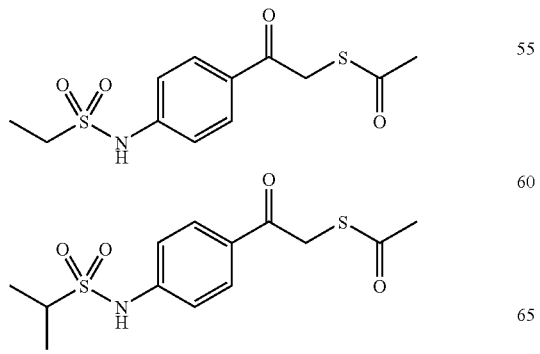

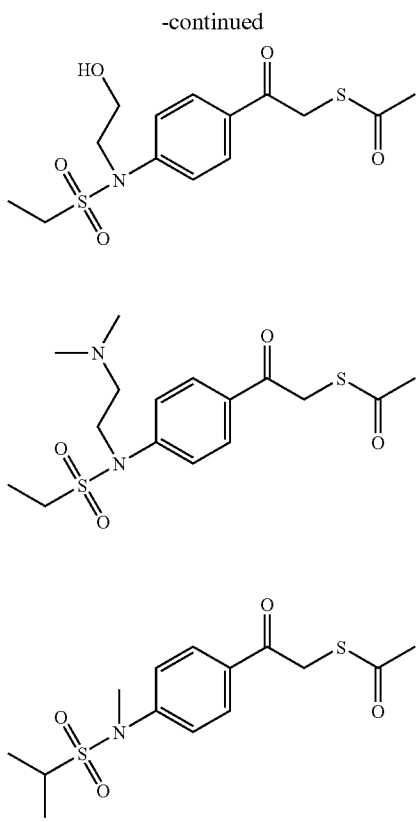

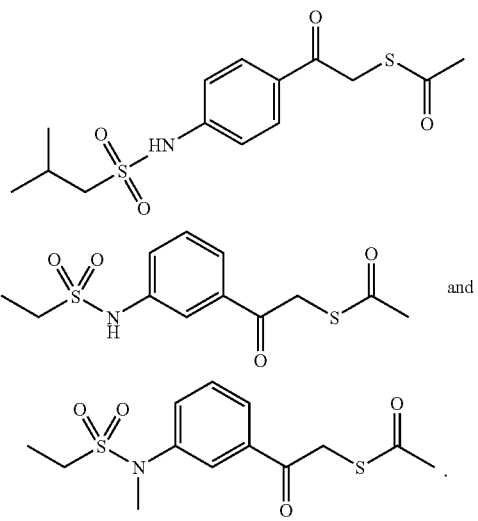

12. The compound of claim 2, having a structure selected from the group consisting of formula (X) and formula (XI);

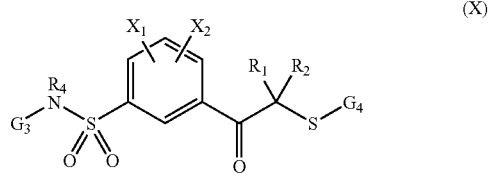

(X)

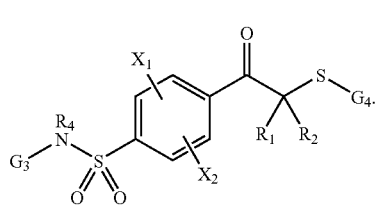
(XI)

13. The compound of claim 12 having a structure selected from the group consisting of formula (XII) and formula (XIII)

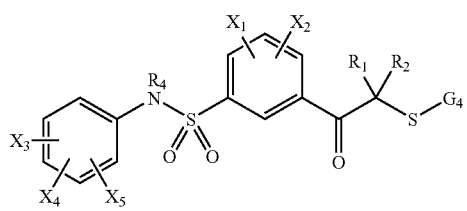
(XII)

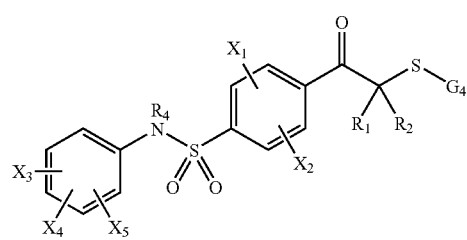
XIII wherein $X_3$, $X_4$, and $X_5$ are each independently selected froma the group consisting of hydrogen, perhaloaryloxy, alkanoylalkyl, N-aryl-N-alkylamino, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamide, N-arylcarboxamidoalkoxy, cycloalkylcarbonyl, cyanoalkoxy, carboxy, cycloalkylamino, acylalkyl, acylalkoxy, aroylalkoxy, aralkylaryl, aralkyl, aralkenyl, aralkynyl, haloalkylthio, alkanoyloxy, alkoxy, alkoxyalkyl, cycloalkoxy, cycloalkylalkoxy, hydroxyl, amino, thio, nitro, alkylamino, alkylthio, arylamino, aralkylamino, arylthio, arylthioalkyl, alkylsulfonyl, arylsuiphonyl, alkanoyl, alkenoyl, aroyl, aralkanoyl, haloalkanoyl, alkyl, alkenyl, alkynyl, alkenyloxy, alkylenedioxy, haloalkylenedioxy, cycloalkyl, cycloalkylalkanoyl, halo, haloalkyl, haloalkoxy, hydroxyhaloalkyl, hydroxyhaloalkoxy, hydroxyalkyl, aryl, aryloxy, aralkoxy, arylalkenyl, carboalkoxy, alkoxycarboxamido, alkylamidocarboylamido, arylamidocarboylamido, carboalkoxyalkyl, carboalkoxyalkenyl, carboamido, carboxamidoalkyl, cyanocycloalkylalkyl, cycloalkenyl, alkoxycarbonyl, aralkylthio, alkylthio, alkylsulfinyl, arylsulfinyl, dialkylamino, aminoalkyl, dialkylaminoalkyl, aminoaryl, alkylaminoaryl, acylamino, aminocarbonylalkoxy, aminocarbonylamino, aminothiocarbonylamino, and aminothiocarbonylaminoalkyl.

14. The compound of claim 13 wherein $G_4$ is an optionally substituted acyl having structural formula —C(O)$R_E$, wherein $R_E$ is selected from the group consisting of any pharmaceutically acceptable acid, —P(O)(OH)$_2$, and —P(O)(OR$_5$)$_2$; $R_1$ and $R_2$ are each independently selected from the group consisting of hydrogen and lower alkyl, or $R_1$ and $R_2$ taken together form optionally substituted cycloalkyl; and $X_1$ and $X_2$ are each independently selected from the group consisting of hydrogen, halogen, hydroxyl, lower alkyl, lower perhaloalkyl, lower alkoxy and lower perhaloalkoxy.

15. The compound of claim 14 wherein $R_3$ is selected from the group consisting of hydrogen, optionally substituted lower alkyl, and a structural element known to confer aqueous solubility.

16. The compound of claim 15 wherein the compound has a structure selected from the group consisting of:

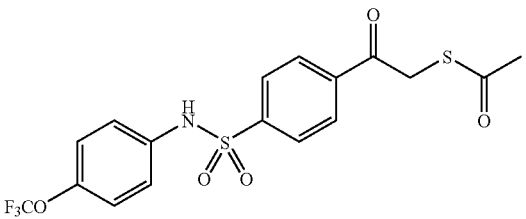

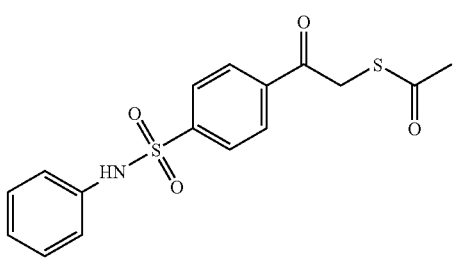

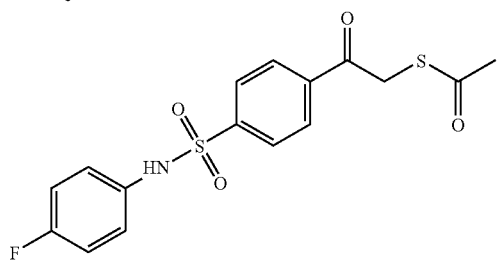

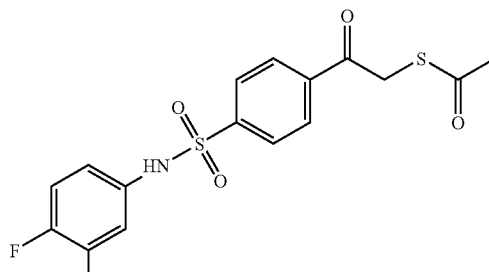

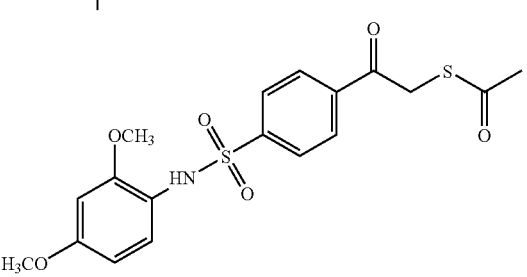

121
-continued
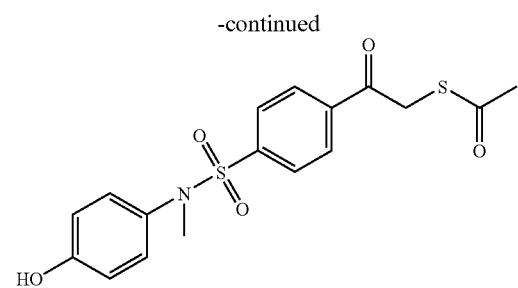
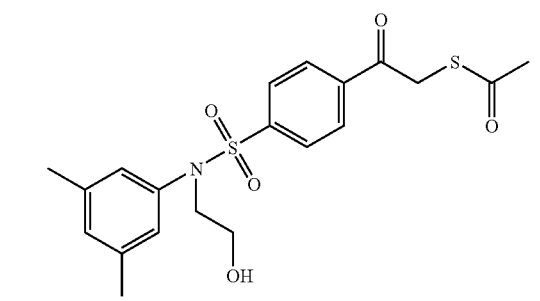
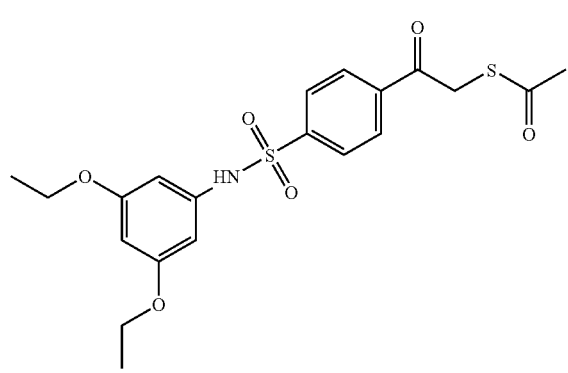
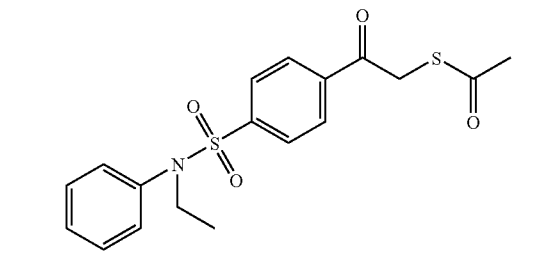
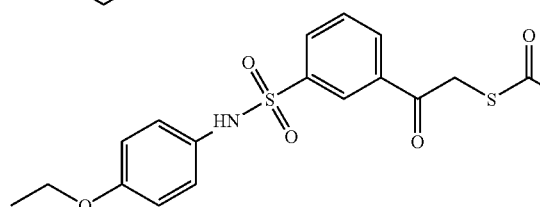
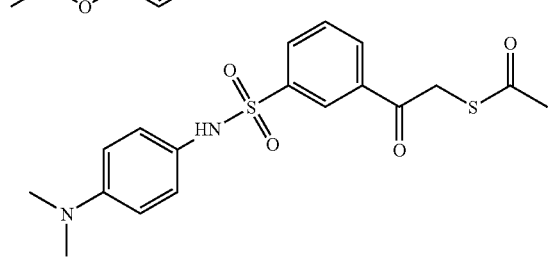
122
-continued
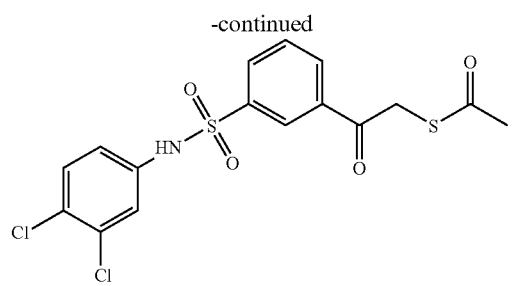
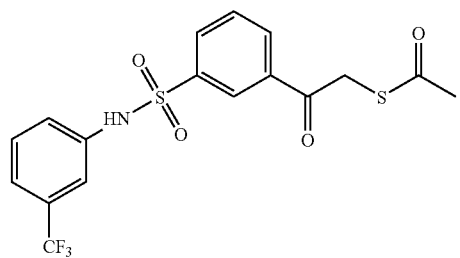
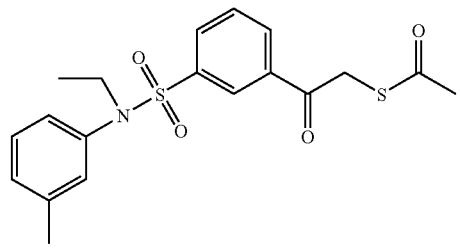
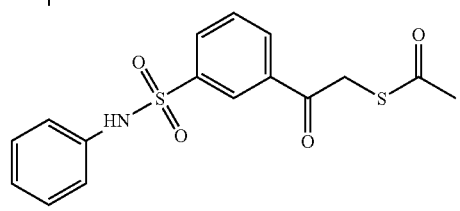
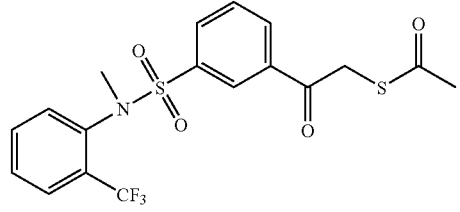
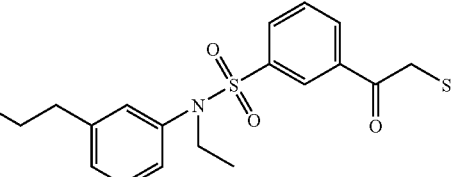
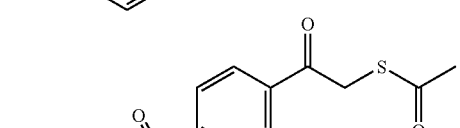
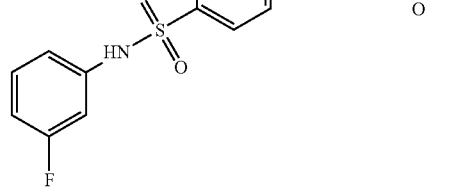

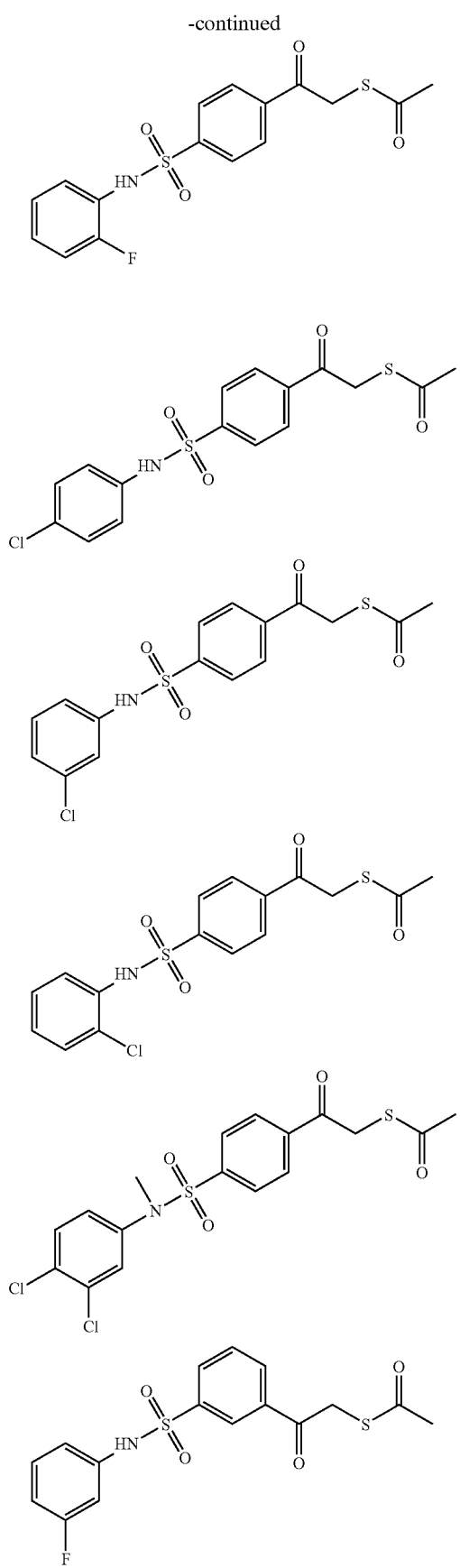

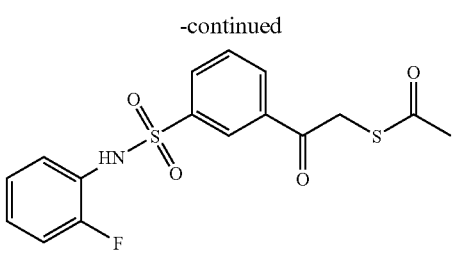

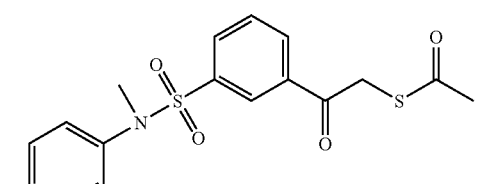

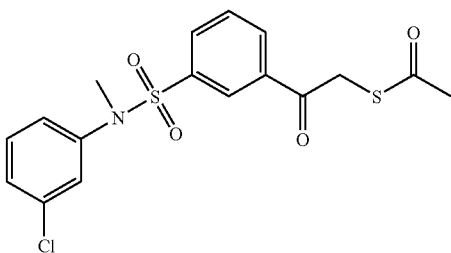

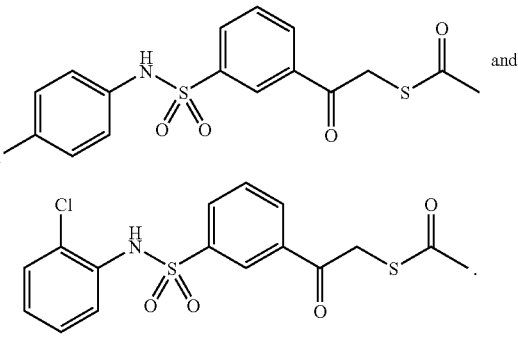

17. The compound of claim 12 wherein $G_3$ comprises an optionally substituted alkyl.

18. The compound of claim 17 wherein $G_4$ is an optionally substituted acyl having structural formula $-C(O)R_E$, wherein $R_E$ is selected from the group consisting of any pharmaceutically acceptable acid, $-P(O)(OH)_2$, and $-P(O)(OR_5)_2$; $R_1$ and $R_2$ are each independently selected from the group consisting of hydrogen and lower alkyl, or $R_1$ and $R_2$ taken together form optionally substituted cycloalkyl; and $X_1$ and $X_2$ are each independently selected from the group consisting of hydrogen, halogen, hydroxyl, lower alkyl, lower perhaloalkyl, lower alkoxy and lower perhaloalkoxy.

19. The compound of claim 18 wherein $R_3$ is selected from the group consisting of hydrogen, optionally substituted lower alkyl, and a structural element known to confer aqueous solubility.

20. The compound of claim 19 wherein the compound has a structure selected from the group consisting of:

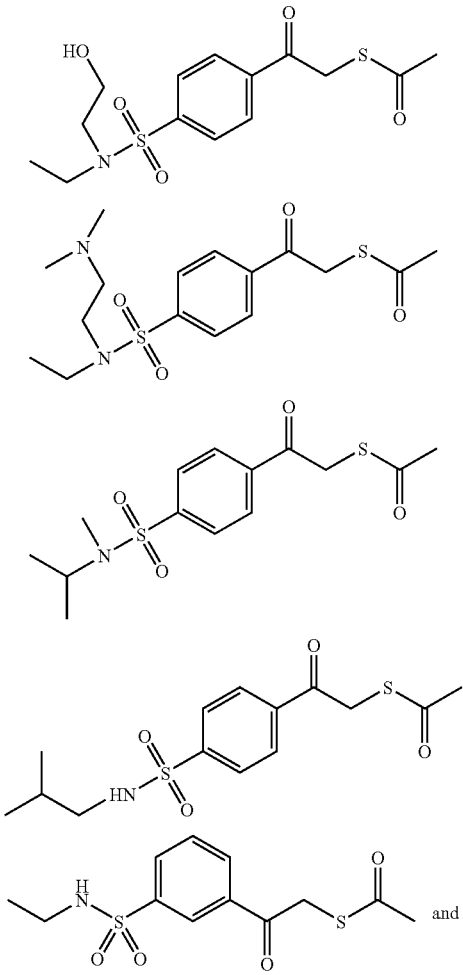

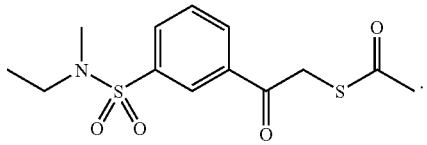

21. The compound of claim 1 wherein the compound has the structure consisting of:

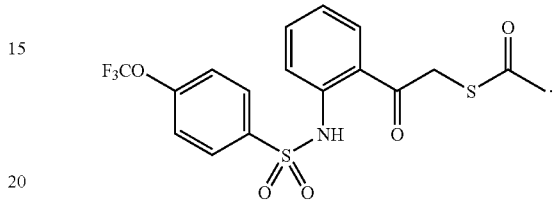

22. The compound of claim 1, wherein $R_3$ is a structural element known to confer aqueous solubility.

23. The compound of claim 22, wherein $R_3$ is N-piperazinylethyl.

24. The compound of claim 22, wherein $R_3$ is N-morpholinylethyl.

25. The compound of claim 22, wherein $R_3$ is 1,3-dihydroxy-2N-propanoyl.

26. The compound of claim 1, wherein $R_4$ is a structural element known to confer aqueous solubility.

27. The compound of claim 26, wherein $R_4$ is N-piperazinylethyl.

28. The compound of claim 26, wherein $R_4$ is N-morpholinylethyl.

29. The compound of claim 26, wherein $R_4$ is 1,3-dihydroxy-2N-propanoyl.

30. A pharmaceutical composition comprising a compound as recited in claim 1 together with a pharmaceutically acceptable carrier.

* * * * *